(12) United States Patent
Flynn et al.

(10) Patent No.: US 12,060,547 B2
(45) Date of Patent: *Aug. 13, 2024

(54) PHOTOSYNTHETIC BIOREACTOR FOR THE CONVERSION OF ELECTRICITY AND FERTILIZER INTO BIOMASS

(71) Applicant: ForeLight, Inc., Cambridge, MA (US)

(72) Inventors: Adam Flynn, Cambridge, MA (US); Julie Moffitt, Cambridge, MA (US)

(73) Assignee: ForeLight, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/096,851

(22) Filed: Jan. 13, 2023

(65) Prior Publication Data
US 2023/0279320 A1 Sep. 7, 2023

Related U.S. Application Data

(63) Continuation of application No. 16/641,918, filed as application No. PCT/US2018/045842 on Aug. 8, 2018, now Pat. No. 11,555,170.

(60) Provisional application No. 62/542,544, filed on Aug. 8, 2017.

(51) Int. Cl.
  *C12M 1/00* (2006.01)
  *C12M 1/34* (2006.01)
  *C12M 3/00* (2006.01)
  *C12N 1/12* (2006.01)
  *C12N 1/20* (2006.01)

(52) U.S. Cl.
  CPC ............ *C12M 21/02* (2013.01); *C12M 23/02* (2013.01); *C12M 23/20* (2013.01); *C12M 23/44* (2013.01); *C12M 31/10* (2013.01); *C12M 41/12* (2013.01); *C12N 1/12* (2013.01); *C12N 1/20* (2013.01)

(58) Field of Classification Search
None
See application file for complete search history.

(56) References Cited

U.S. PATENT DOCUMENTS

| | | | |
|---|---|---|---|
| 11,555,170 B2 * | 1/2023 | Flynn | ............... C12M 31/10 |
| 2009/0130704 A1 | 5/2009 | Gyure | |
| 2010/0279395 A1 | 11/2010 | Haley, III | |
| 2010/0311156 A1 | 12/2010 | Beliaev et al. | |

(Continued)

FOREIGN PATENT DOCUMENTS

| | | |
|---|---|---|
| CN | 102352304 | 2/2012 |
| CN | 103261395 A | 8/2013 |

(Continued)

OTHER PUBLICATIONS

International Search Report and Written Opinion dated Oct. 10, 2018, 2018 for International Application No. PCT/US2018/045842.

*Primary Examiner* — William H. Beisner
(74) *Attorney, Agent, or Firm* — Perkins Coie LLP

(57) ABSTRACT

A photobioreactor for cultivation and/or propagation of a photosynthetic organism and associated systems/methods are disclosed herewith. The photobioreactor includes (1) a substantially spherical vessel having a wall defining an interior vessel volume; (2) a water-submersible system for converting electrical energy into electromagnetic radiation; (3) a temperature management system for circulating heat dispersal fluid into and out of the water-submersible system; and (4) a photobioreactor control system comprising a processor and a controller.

14 Claims, 34 Drawing Sheets

(56) References Cited

U.S. PATENT DOCUMENTS

| | | |
|---|---|---|
| 2012/0268936 A1 | 10/2012 | Pickard |
| 2013/0114279 A1 | 5/2013 | Marley |
| 2013/0260450 A1 | 10/2013 | Fey et al. |
| 2014/0011245 A1 | 1/2014 | Flynn et al. |
| 2014/0030695 A1 | 1/2014 | Smith |
| 2015/0275240 A1 | 10/2015 | Flynn et al. |
| 2016/0282338 A1 | 9/2016 | Miklas et al. |

FOREIGN PATENT DOCUMENTS

| | | | |
|---|---|---|---|
| JP | AS55034089 | 3/1980 | |
| JP | AH07000176 | 1/1995 | |
| JP | H07031466 | 2/1995 | |
| JP | 2007522801 | 8/2007 | |
| JP | 2009513140 | 4/2009 | |
| JP | 2012183002 A | 9/2012 | |
| JP | 2014014365 | 1/2014 | |
| JP | 2015-510768 | 4/2015 | |
| WO | WO 2009/002772 | 12/2008 | |
| WO | WO 2009/039317 | 3/2009 | |
| WO | WO 2011/022594 | 2/2011 | |
| WO | WO-2013079948 A1 * | 6/2013 | ............ C12M 21/02 |
| WO | WO 2013/103306 | 7/2013 | |

* cited by examiner

1901

A  B  C

PHOTOSYNTHETIC BIOREACTOR FOR THE CONVERSION OF ELECTRICITY AND FERTILIZER INTO BIOMASS

CROSS-REFERENCE TO RELATED APPLICATIONS

This application is a continuation of U.S. patent application Ser. No. 16/641,918 filed Feb. 25, 2020, which is a 371 U.S. National Stage of International Application No. PCT/US2018/045842 filed Aug. 8, 2018, which claims priority to U.S. Provisional Application No. 62/542,544 filed Aug. 8, 2017, the entire contents of which are hereby incorporated by reference herein.

BACKGROUND

Photobioreactors have been described for the use of cultivating alga and generally employ shallow lagoons or ponds that are agitated with one or more paddle wheels and use substantially or exclusively natural light sources, or substantially enclosed units using artificial light sources. Algal ponds are plagued with problems including poor production of algae due to seasonal and daily climatic changes and contamination. Given that such bioreactors are generally constructed to receive the sun's daylight light, productivity is limited by intensity of the sun which depends on the photoperiod and the season, among other factors. Artificial light bioreactors overcome some of these challenges but are further challenged by an inability to scale effectively. Therefore, it is advantageous to have an improved system and method that can cultivate and/or propagate photosynthetic organism more effectively and efficiently

SUMMARY OF THE INVENTION

The present disclosure provides systems and methods for the cultivation and/or propagation of a photosynthetic or photosensitive organism, such as cyanobacteria or microalgae, using a photobioreactor. More particularly, the disclosure provides a photobioreactor for cultivation and/or propagation of a photosynthetic or photosensitive organism. The photobioreactor includes, inter alia, (1) a substantially spherical vessel having a wall defining an interior vessel volume; (2) a water-submersible system for converting electrical energy into electromagnetic radiation; (3) a temperature management system for circulating heat dispersal fluid into and out of the water-submersible system; and (4) a photobioreactor control system comprising a processor and a controller. The interior vessel volume of the substantially spherical vessel (or external vessel) is configured to contain working fluid where photosynthetic organisms are cultivated, also referred to herein as a productive culture. The water-submersible system can include an inner vessel (which has an inner wall defining an inner space). The water-submersible system includes a light source positioned in the inner space and configured to convert electrical energy into electromagnetic radiation (which can help grow the photosynthetic organisms). The water-submersible system is coupled to and controlled by the photobioreactor control system. The temperature management system can circulate heat dispersal fluid into and out of the inner space such that the temperature of the light source can be adjusted and/or controlled. By this arrangement, the photobioreactor can effectively cultivate or propagate the photosynthetic organisms by controlling the environmental conditions in the substantially spherical vessel.

BRIEF DESCRIPTION OF THE DRAWINGS

The foregoing summary, as well as the following detailed description of the disclosure, will be better understood when read in conjunction with the appended figures. It should be understood that the disclosure is not limited to the precise arrangements, examples and instrumentalities shown.

DETAILED DESCRIPTION OF THE INVENTION

Figure 1:
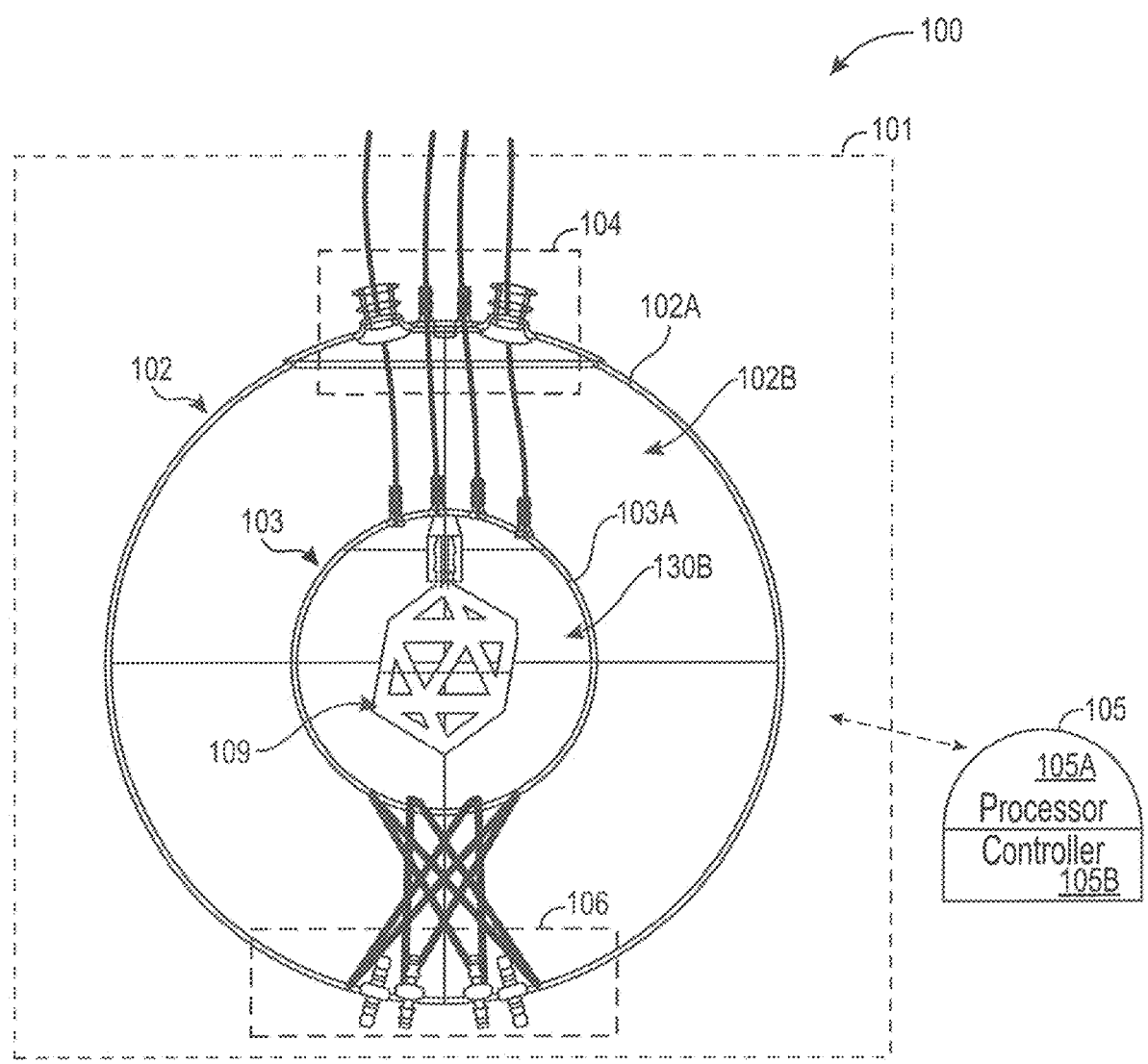
FIG. 1 shows a spherical-shaped photobioreactor in accordance with embodiments of the present disclosure.

The following detailed description of the disclosure will be better understood when read in conjunction with the appended figures. It should be understood that the disclosure is not limited to the precise arrangements, examples and instrumentalities shown. It should also be understood that the word "exemplary" is used herein to mean "serving as an example, instance, or illustration." Any embodiment described herein as "exemplary" is not necessarily to be construed as preferred or advantageous over other embodiments.

The present disclosure provides methods and materials for the cultivation and/or propagation of a photosynthetic or photosensitive organism, such as cyanobacteria or microalgae, using a photobioreactor. In various embodiments, the photobioreactor of the invention is suitable for the culture of any kind of photosynthetic organism, such as algae and cyanobacteria, multicellular organisms such as seaweed, plant cells, or other naturally occurring and/or unmodified organisms, including such organisms as have substantially adapted to a given environment through guided natural selection. As used herein, the term "photosynthetic organism" also includes organisms genetically modified or genetically edited by techniques well known to one skilled in the respective art. As used herein, the term "photosynthetic organism" further includes organisms that were synthetically assembled using techniques well known to one skilled in the art. The photosynthetic organisms described herein include, among others, those known to produce compounds or biomolecules such as fatty acids, phycobiliproteins, biofuels and other petrol substitutes, and the like. As used herein, the term "photosynthetic organism" further includes photosensitive organisms that respond to light stimulation in ways other than or in addition to photosynthesis, such as certain types of bacteria and plant cells, thereby enabling the use of light stimulation as an additional method of control.

In one embodiment, the photobioreactor described herein comprises a substantially spherical vessel having a wall defining an interior vessel volume (also referred to as an "outer vessel wall" or "external wall"), a water-submersible system for converting electrical energy into electromagnetic radiation (e.g., in some embodiments, by a "light source" therein), a temperature management system for regulating temperature of the interior vessel volume, and a circulation system for circulating fluid, gas, waste and/or nutrients into and/or out of the interior vessel volume. In some embodiments, the water-submersible system for converting electrical energy into electromagnetic radiation comprises a substantially spherical wall (also referred to herein as an "inner vessel wall" or "inner wall") defining an inner vessel interior volume or an inner space. In some embodiments, the photobioreactor described herein comprises a housing, an internal structure, an external structure, or a combination of the above, and is referred to herein in aggregate as the reactor housing and/or structure.

FIG. 1 shows a photobioreactor 100 in accordance with embodiments of the present disclosure. As shown, the photobioreactor 100 includes a substantially spherical or spherical vessel 102, a water-submersible system 103, a temperature or heat management system 104, a photobioreactor control system 105, and a circulation system 106. The photobioreactor control system 105 includes (1) a processor 105A configured to process instructions regarding other components of the photobioreactor 100 and (2) a controller 105B configured to communicate with or control other components of the photobioreactor 100. In some embodiments, the photobioreactor control system 105 can communicate with other components via a wired or wireless connection.

The spherical vessel 102 includes a wall (or an external wall) 102A, defining an interior vessel volume 102B. The water-submersible system 103 includes an inner vessel wall 103A defining an inner space 103B. As shown, a light source 109 is positioned in the inner space 103B. In the illustrated embodiments in FIG. 1, the light source 109 is sized smaller than the inner wall 103A. In other embodiments, however, the light source 109 can have different sizes and shapes. For example, the light source 109 can be a surface light source, a line light source, and/or a point light source. The vessel walls (e.g., elements 102A, 103A) may be constructed from a variety of materials that are resistant to leaching, are heat and corrosion resistant, and can withstand moderate pressurization. Appropriate materials include, but are not limited to, plastics (e.g., high-density polyethylene, low-density polyethylene, polypropylene), stainless steel, glass, carbon fiber, silica composites, borosilicate, ceramics and/or bioplastics. In some embodiments, the vessel walls can have a double-layer or dual-layer design (see, e.g., FIGS. 13 and 32). For example, the wall 102A can include (1) an exterior layer facing outwardly toward the housing 101 and (2) an interior layer facing inwardly toward the inner wall 103A. The exterior/interior layer can have different characteristics/coatings/surfaces-treatments suitable for their design purposes. For example, the interior layer can have a water-resistant coating (to prevent the wall 102 from erosion by working fluid positioned in the interior vessel volume 102B or to prevent agglomeration of the working fluid (e.g., culture) on the wall 102), whereas the exterior layer can have a stronger rigidity to prevent damages from accidental, physical impacts from the outside. In some embodiments, the inner wall 103A can also have a double-layer design like the wall 102A.

As shown in FIG. 1, the water-submersible system 103 can be supported by multiple support structures or struts. The support structures couple the water-submersible system 103 to the vessel 102. In some embodiments, the water-submersible system 103 and the vessel 102 can be coupled by other suitable means. In some embodiments, the water-submersible system 103 can float in the interior vessel volume 102B. In some embodiments, the water-submersible system 103 for converting electrical energy into electromagnetic radiation can be surrounded by a substantially spherical barrier, such as a spheroid or toroid barrier, such that the barrier separates the interior water-submersible system 103 from the working fluid (e.g., culture) positioned in the interior vessel volume 102B. The barrier may be constructed from a variety of inert transparent or semi-transparent materials, and/or materials that are tolerant to extreme temperatures. Appropriate materials include, but are not limited to, plastic and glass. The barrier may also be comprised of materials or meta-materials that allow for the manipulation of photons (e.g., photon-sensitive or photon-responsive materials). For example, photons may be manipulated using lensing, variations in attenuation, shifts in wavelength, and the like. In some embodiments, multiple water-submersible systems 103 for converting electrical energy into electromagnetic radiation may be positioned in the interior vessel volume.

The temperature management system 104 is configured to circulate heat dispersal fluid or refrigerant into and out of the water-submersible system 103. By this arrangement, the temperature management system 104 can adjust or manage the temperature of the light source 109 as well as the temperature of the working fluid in the interior vessel volume 102B. In some embodiments, the temperature management system 104 is controlled by the photobioreactor control system 105. In some embodiments, the temperature management system 104 can adjust the temperature in the water-submersible system 103 based on environmental conditions such as an environmental temperature, humidity, presence or degree of external or ambient light, and the like. The temperature management system 104 can include one or more inlets and one or more outlets configured to deliver and receive heat dispersal fluid. In some embodiments, the temperature management system 104 includes one or more motors, pumps, valves, propellers, and/or fans. These components can be electronically-controlled or thermodynamic (heat/temperature-controlled). In some embodiments, these motors, pumps, valves, propellers, and/or fans can be integrated into a vessel wall (e.g., 102A), a housing or other structural component of the photobioreactor 100. In some embodiments, these motors, pumps, valves, propellers, and/or fans can be integrated into the inner wall 103A or the wall 102A.

The circulation system 106 is configured to manipulate, extract, or circulate fluid, waste or nutrients into and out of the spherical vessel 102. The circulation system 106 is in operable communication with the photobioreactor control system 105. In some embodiments, the circulation system 106 includes one or more motors, pumps, valves, propellers, and/or fans. These components can be electronically-controlled or thermodynamic (heat/temperature-controlled). In some embodiments, these motors, pumps, valves, propellers, and/or fans can be integrated into a structural component of the photobioreactor 100. For example, in some embodiments, these motors, pumps, valves, propellers, and/or fans can be integrated into the wall 102A or the water-submersible system 103. In some embodiments, the circulation system 106 can include a spigot configured to control a flow in the circulation system. The circulation system 106 can include one or more inlets and one or more outlets configured to deliver and receive working fluid in the interior vessel volume 102B.

Figure 2:
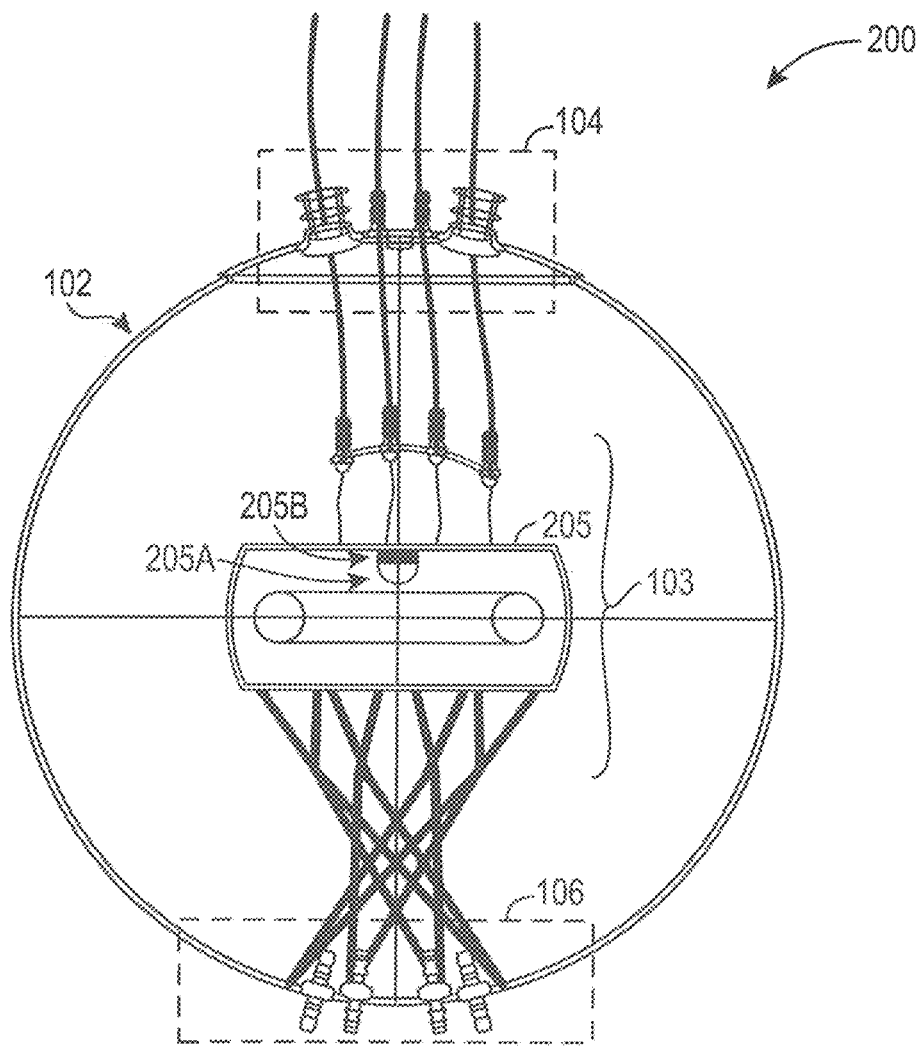
FIG. 2 shows a spherical-shaped photobioreactor in accordance with embodiments of the present disclosure.

FIG. 2 shows another photobioreactor 200 in accordance with embodiments of the present disclosure. The photobioreactor 200 has a structure similar to the photobioreactor 100 (e.g., components with the same reference numbers have the same or similar structural feature and functions). The photobioreactor 200 includes a water-submersible system 103 having a toroid shape with a hydrophobic surface (e.g., coated by hydrophobic or water-proof materials). As shown, the photobioreactor 200 has a control system 205 positioned inside the water-submersible system 103. In the illustrated embodiments, the control system 205 can control and communicate with other components of the photobioreactor 200. By this arrangement, the photobioreactor 200 can operate based on the instructions stored in the control system 205, without requiring instructions from the outside. In some embodiments, this control system 205 may comprise a microprocessor 205A and a microcontroller 205B In some embodiments, one or more components of the photobioreactor (e.g., photobioreactor 100 or 200) may be produced using additive manufacturing processes including, for example, stereolithography (SLA), fused filament fabrication (FFF), fused deposition modeling (FDM), selective laser sintering, direct metal laser sintering, binder jetting, directed energy deposition, material extrusion, material jetting, powder bed fusion, sheet lamination, vat photopolymerization, or a combination of one or more processes or techniques well known to one skilled in the respective art. The materials used for additive manufacturing may comprise porous or semipermeable materials, glass, plastics, bioplastics, recycled plastics, conductive materials, or other materials generally available for use in additive manufacturing processes. The materials used for additive manufacturing may also comprise organic or biological materials, such as cellulose, tree resin or the biogenic remains of an organism. For example, the materials may comprise a polymer feedstock with a relatively low melting point that acts as a carrier for silica nanoparticles or micro-particles or the biogenic silica remains of a microorganism. In this example, when the additively manufactured component is exposed to a temperature greater than 1400 degrees Celsius for a sufficient time, the polymer feedstock burns off and silica nanoparticles fuse to form a substantially glass fused structure. The materials used for additive manufacturing may also comprise two or more materials that fuse during the manufacturing process to form a water-impermeable or substantially water-impermeable barrier.

In some embodiments, one or more surfaces of the photobioreactor may have hydrophobic, superhydrophobic, hydrophilic, or oleophobic properties that will, for example, reduce the coefficient of friction and increase the ease of fluid flow throughout the system, along with ancillary benefits, for example, preventing biomass from adhering to the vessel, light source or other photobioreactor components. These hydrophobic, superhydrophobic, hydrophilic or oleophobic properties may be achieved through one or more methods well known to one skilled in the art, including, for example, the addition of surface coatings, mechanical or thermal etching, treatment through electrochemical processes, high-resolution additive manufacturing or the use of inherently hydrophobic, superhydrophobic, hydrophilic or oleophobic materials.

In various embodiments, a photobioreactor of this invention may comprise one or more stand-alone components that function independently, two or more interconnected components, or a combination of interconnected and stand-alone components. In some embodiments, for example, the light source(s) may be connected to external pumps and/or power supplies, while in other embodiments, the light source(s) may be a stand-alone functional component.

In some embodiments, one or more photobioreactor components may be integrated into the outer vessel wall, the inner vessel wall, the light source or another photobioreactor structure. For example, conductive materials may be embedded into the outer vessel wall or the inner vessel wall to supply power, relay electronic control signals, and/or to return sensor data. In some embodiments, the embedded conductive materials may be interconnected in such a way as to provide for massively parallel redundancies in power supply.

In some embodiments, one or more components may be positioned in the void between the interior vessel and the exterior vessel wall. In further embodiments, one or more components may be positioned outside the exterior vessel of the photobioreactor. In some embodiments, for example, one or more power supplies may be positioned outside of the photobioreactor vessel, while in some embodiments one or more power supplies may be positioned inside the internal vessel volume. In further embodiments, external power supplies may provide wireless power transfer to one or more internal components, or one or more components may be powered through direct introduction of power into the culture or the heat dispersal fluid or medium.

In some embodiments, a photobioreactor as described may function independently as a stand-alone biomass production system. One or more photobioreactors may also be combined to operate as a high-density photobioreactor array comprised of multiple individual photobioreactors that are commonly controlled and/or arranged in close proximity. For example, two or more vessels may be assembled using an external rigid rack or scaffolding, or using infrastructure built or additively manufactured into the vessels themselves. In one embodiment of the high-density configuration, two or more of the individual vessels are of uniform volume and/or dimensions. In another embodiment, two or more of the vessels are of varying volume and/or dimensions. A high-density configuration may be assembled into a geometrical configuration that utilizes the maximum available space in a given area.

Figure 3:
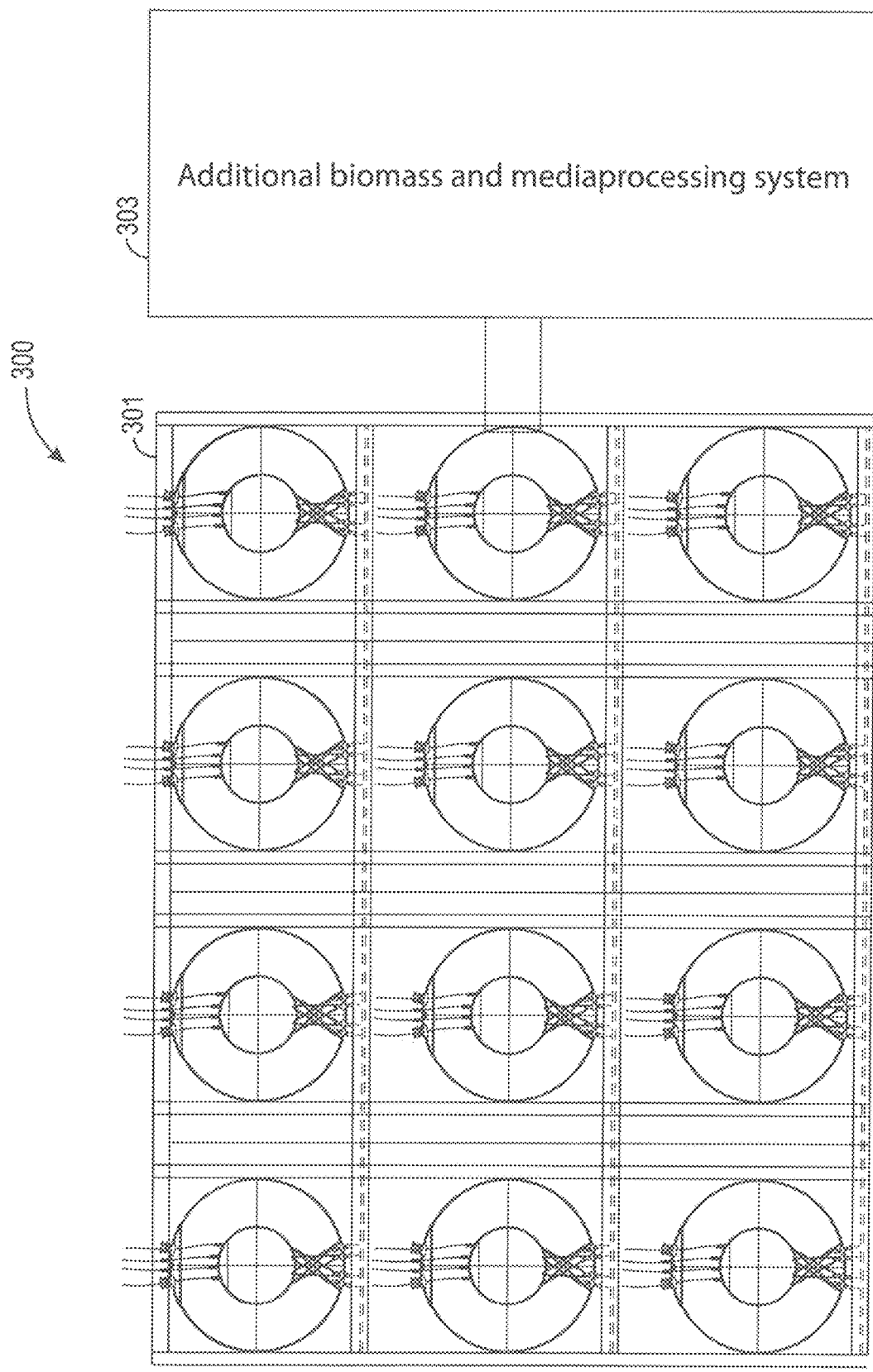
FIG. 3 shows a system having multiple spherical-shaped photobioreactors in accordance with embodiments of the present disclosure.
Figure 4:
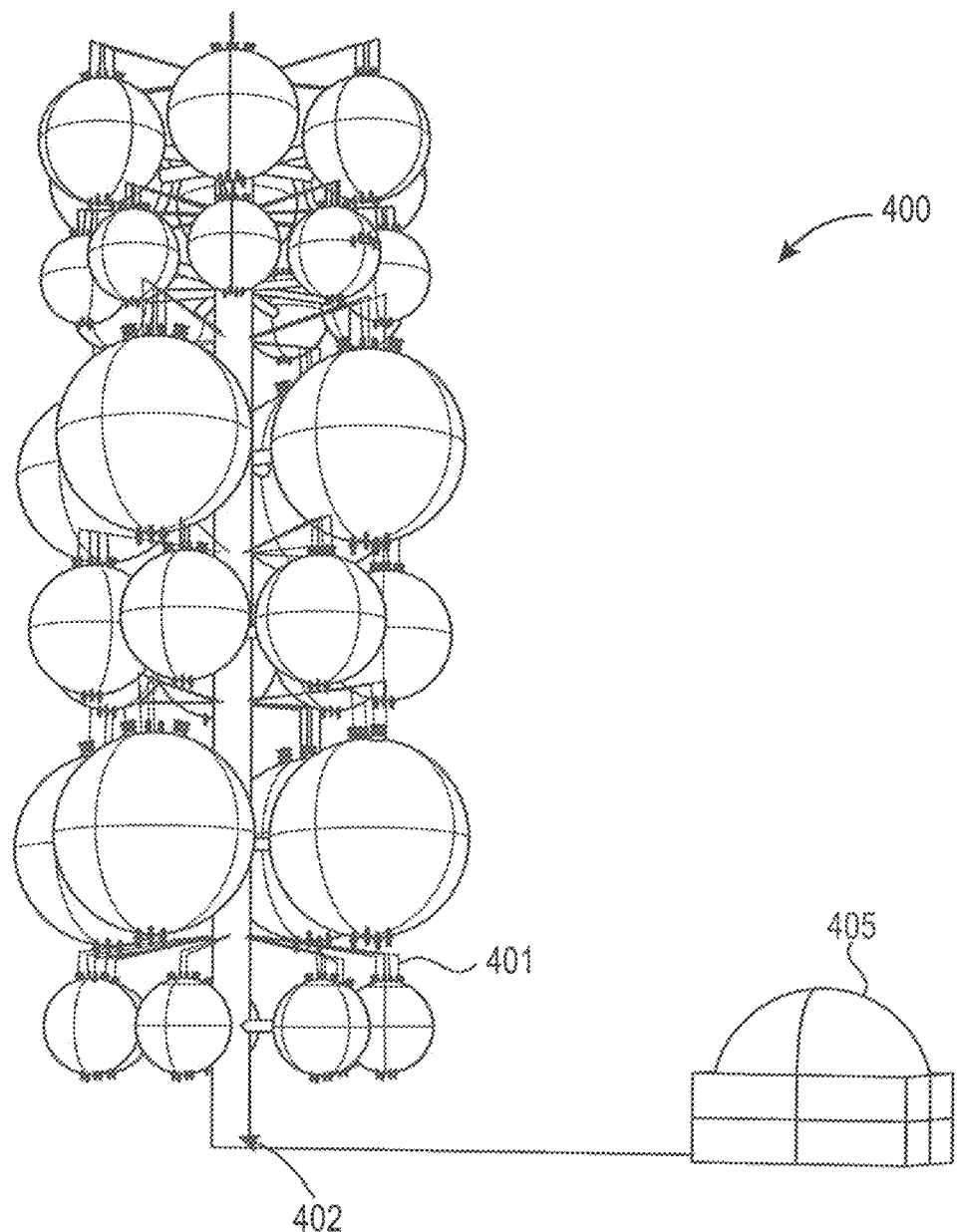
FIG. 4 shows a configuration of a system having multiple spherical-shaped photobioreactors in accordance with embodiments of the present disclosure.

FIG. 3 shows a system 300 having multiple spherical-shaped photobioreactors in accordance with embodiments of the present disclosure. As shown, the system 300 includes multiple photobioreactors 301 coupled to one another. For example, the working fluid in one of these photobioreactors 301 can flow to an adjacent photobioreactors. These photobioreactors 301 are further coupled to (e.g., in fluid communication with) a biomass or media processing system 303. The biomass or media processing system 303 is configured to provide raw materials to, and receive produced biomass from, the multiple photobioreactors 301. The system 300 is suitable for mass-production of biomass by using the multiple photobioreactors 301. In some embodiments, the multiple photobioreactors 301 do not need to be physically located close to one another, and can be coupled by pipes, channels, etc. for fluid communication FIG. 4 shows a configuration of a system 400 having multiple spherical-shaped photobioreactors in accordance with embodiments of the present disclosure. In the illustrated embodiments, the system 400 can have multiple photobioreactors positioned at multiple (vertical) levels. The multiple photobioreactors can have different sizes, shapes, or volumes. In some embodiments, these multiple photobioreactors can be controlled by a central control system 405. In some embodiments, these photobioreactors can be controlled by individual controllers/processors positioned therein.

In a high-density configuration, space may be provided between individual photobioreactor vessels, or between groups of vessels (photobioreactor modules), to provide for connectivity of one vessel to another. In some embodiments, for example, one vessel may be interconnected with one or more adjacent vessels so as to share media, gasses and/or a common control system. In further embodiments, a set or series of valves 401 may direct the flow of fluids, solids and/or gases between and among one or more photobioreactors in a substantially predetermined manner. In other embodiments, space may be provided between multiple photobioreactors for one or more central columns 402 to provide for light distribution and/or electrical connectivity between multiple photobioreactors.

In some embodiments of the high-density photobioreactor configuration, two or more vessels may be assembled in such a way as to occupy an existing structure such as, for example, a silo. In other embodiments, two or more vessels may be assembled to occupy a dedicated structure built for the purpose of housing the vessels, or to house the vessels as well as additional biomass and media processing systems or other related equipment or operations. In further embodiments, two or more vessels may be substantially manufactured in place using additive manufacturing processes.

Figure 5:
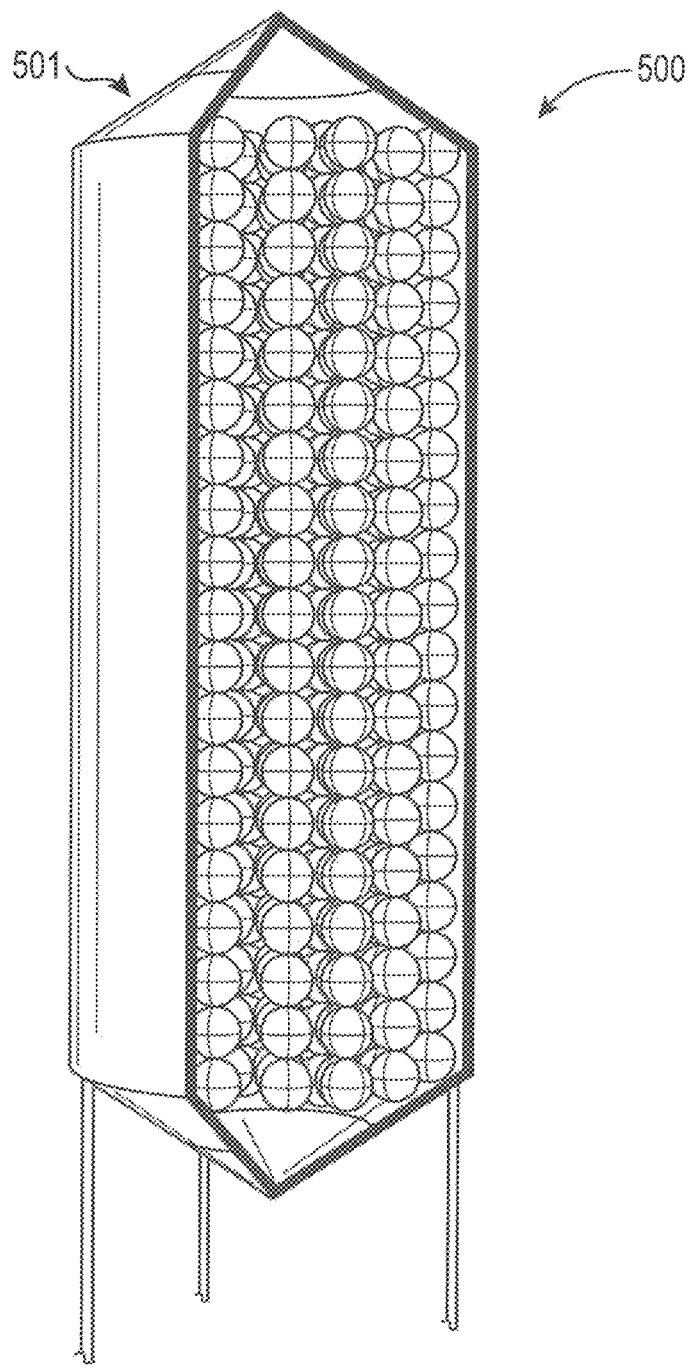
FIG. 5 shows a configuration of a system having multiple spherical-shaped photobioreactors in accordance with embodiments of the present disclosure.

FIG. 5 shows a configuration of a system 500 having multiple spherical-shaped photobioreactors in accordance with embodiments of the present disclosure. As shown, the system 500 includes a housing structure 501 to accommodate multiple photobioreactors. By this arrangement, the system 500 has a high-density configuration which enables the system 500 to be implemented in urban areas. For example, the system 500 can be implemented in a crawl space of a house, or other suitable spaces in a high-rise building.

Figure 6:
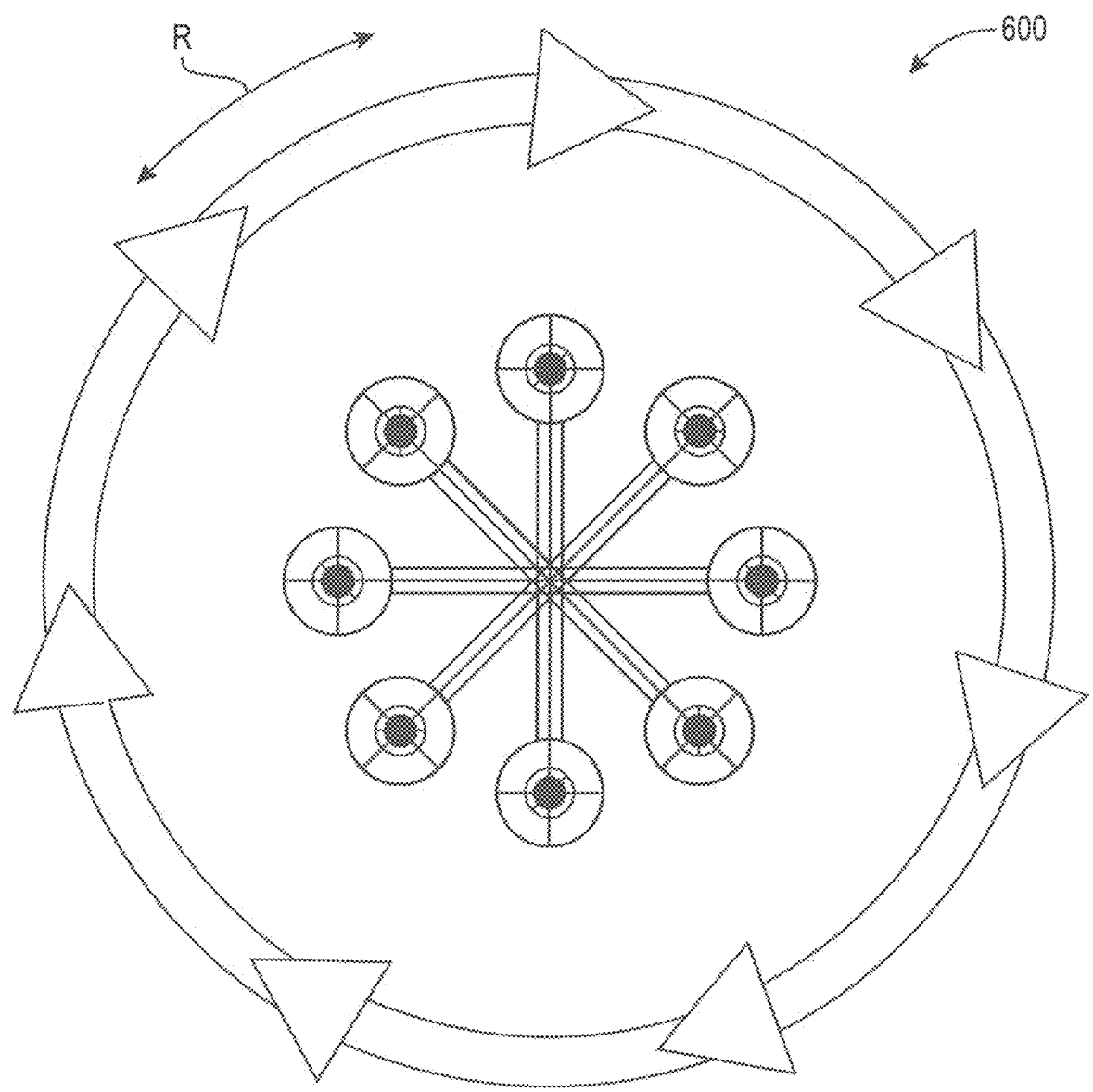
FIG. 6 shows a configuration of a system having multiple spherical-shaped photobioreactors in accordance with embodiments of the present disclosure.

FIG. 6 is a top schematic view showing a system 600 having multiple spherical-shaped photobioreactors in accordance with embodiments of the present disclosure. The multiple photobioreactors in the system 600 are circumferentially positioned and can be rotated in direction R, as indicated. For example, when an environmental condition changes, the system 600 can rotate the photobioreactors to achieve a goal, such as to have all photobioreactors receive substantially equal amounts of external sun or ambient light.

In another embodiment of the high-density configuration, a multitude of individual photobioreactors or of high-density photobioreactor systems may be arranged in a ring around a central axis. In a further embodiment, the ring of photobioreactors may be rotated around the central axis with a sufficient rate of rotation to generate centrifugal force. The centrifugal force generated may, for example, simulate gravitational pull within the reactor vessel at levels sufficient for a given organism's life cycle.

In some embodiments, a photobioreactor according to the present disclosure may comprise one or more control systems that perform initiation, operation, monitoring, data management, maintenance and other executive or interpretational functions. In some embodiments, such functions may be optimized for one or more parameters including, for example, optimal environment for the organism(s) being cultivated, target end product(s), production efficiency, bioremediation (uptake of, for example, $CO_2$), system integrity, or system longevity. Two or more photobioreactor control systems may be interconnected to form a substantially distributed network of photobioreactors, allowing for control of individual photobioreactors, photobioreactor modules and/or full high-density arrays of photobioreactors. For example, in some embodiments, a control system can control multiple photobioreactors in a group (e.g., an array of photobioreactors). The control system can be an external control system (e.g., element 405 or 700) or an internal control system (element 205) positioned in one of the multiple photobioreactors.

Figure 7:
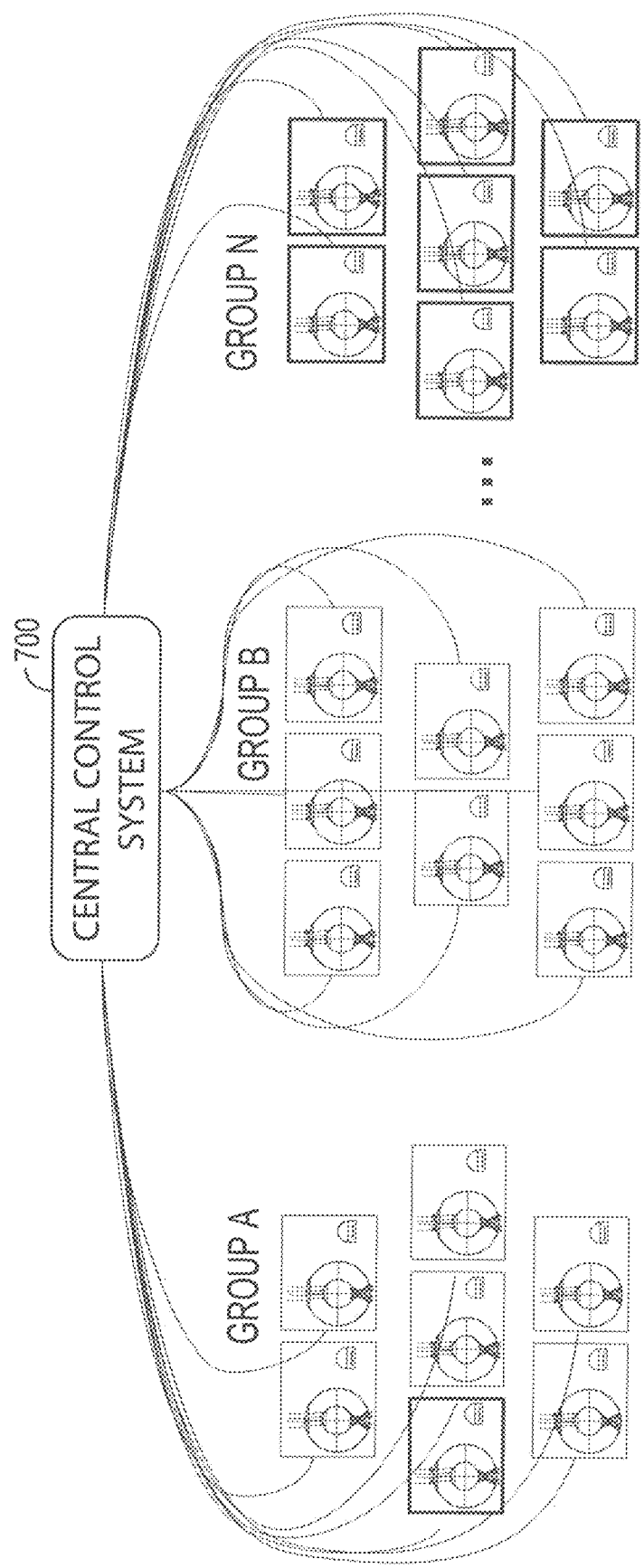
FIG. 7 is a schematic diagram showing a central control system for managing multiple photobioreactors in accordance with embodiments of the present disclosure.

FIG. 7 is a schematic diagram showing a central control system 700 for managing multiple photobioreactors in accordance with embodiments of the present disclosure. As shown, the central control system 700 can control a plurality of groups of photobioreactors located in various locations (e.g., Groups A-N). In some embodiments, the photobioreactors in the same group can be operated by the same (or substantively similar) set of instructions.

In an embodiment, one or more systems of control may be substantially designed as an artificial intelligence (AI) characterized by the use of a machine learning approach or technique well known to one skilled in the respective art. For example, a top-down AI may utilize either individual photobioreactors or modules as a system through which multiple optimization scenarios can be run until a solution, process or path is identified that optimizes for the desired parameter (e.g., growth rate, product expression, overall reactor performance). In some embodiments, the AI uses the information obtained through the optimization scenarios to control a massively distributed network of interconnected reactors. In other embodiments, the AI has the ability to make queries of third-party systems in order to analyze problems, such as, for example, a quantum computer or internet-based resource(s).

Figure 8:
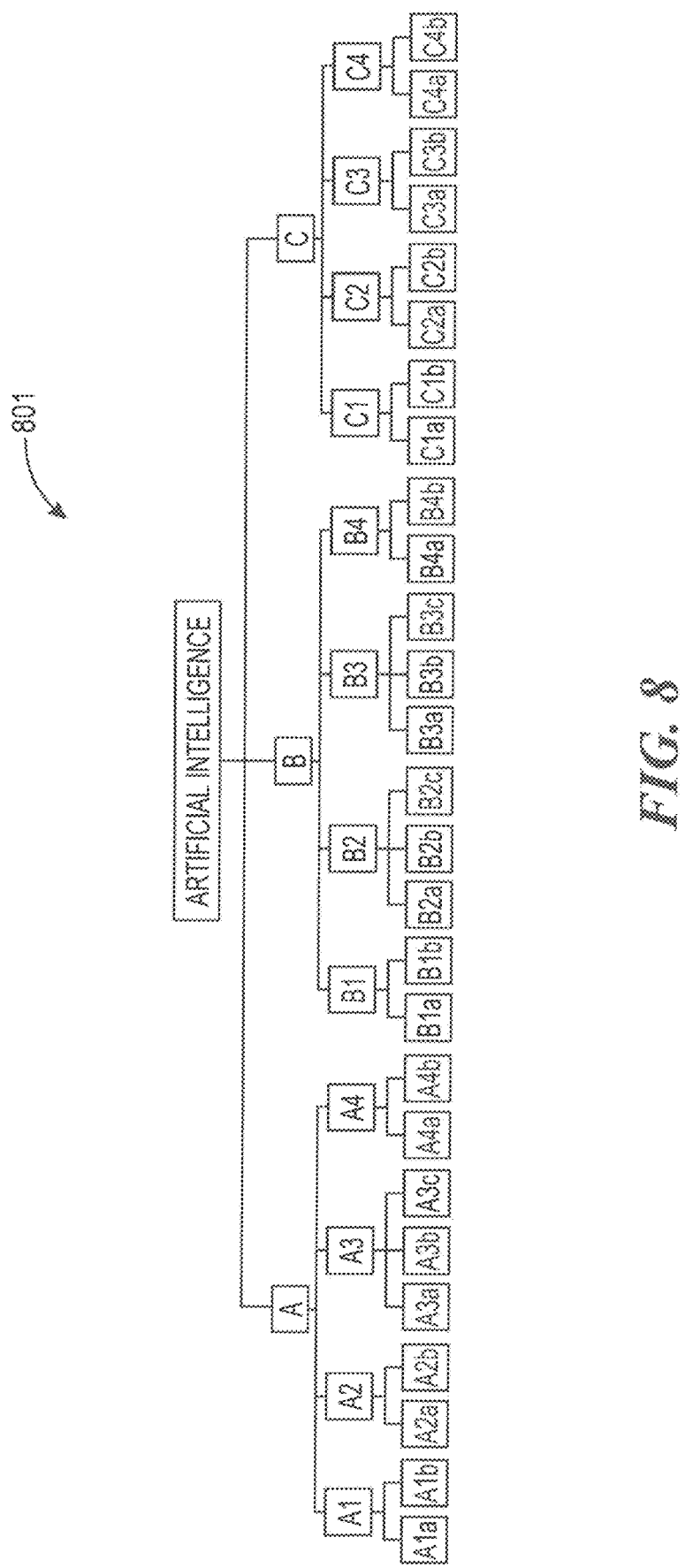
FIG. 8 is a schematic diagram showing a control system for using an artificial intelligence (AI) method (e.g., a "top-down" approach) to manage multiple photobioreactors in accordance with embodiments of the present disclosure.

For example, FIG. 8 is a schematic diagram showing a control system 801 using an artificial intelligence (AI) method (e.g., a "Top-Down" approach) to manage multiple photobioreactors (e.g., A1a-A4b, B1a-B4b, and C1a-C4b). The control system 801 divides the multiple photobioreactors into groups (e.g., A, B, or C) or subgroups (A1, A2, or A3) and then determines how to operate the photobioreactors in each group or subgroup so as to achieve an object (e.g., to maximize production in a time period, to produce a certain amount of biomass in a limited time, to produce biomass at a certain quality/density, to achieve the lowest external energy consumption, to produce biomass at a certain rate, etc.). The control system 801 can utilize AI or machine learning approaches to determine how to operate each of the multiple photobioreactors. In some embodiments, the multiple photobioreactors can be operated based on hierarchy (e.g., reactor A1b follows instructions for Group "A," Sub-group "1," and Sub-group "b").

In another embodiment of the distributed photobioreactor network, one or more control systems may be substantially designed using a swarm control method characterized by, for example, the deployment of small low-power computers to each photobioreactor that compare sensor input between individual photobioreactors. In some embodiments, the small low-power computers are able to make immediate decisions about how to respond to sensor input through a fixed number of possible reactions to sensor stimuli or data.

The swarm control system may feed the information obtained through sensors back to a central photobioreactor control system, or it may enable limited interconnectivity between adjacent photobioreactors, or it may allow for a combination of adjacent interconnectivity and a central photobioreactor control system. In some embodiments, the small low-power computers may be capable of making decisions based on what adjacent photobioreactor control systems decide and the outcomes of those behaviors. For example, using a swarm methodology driven by and optimized off of a flocking algorithm, each system makes decisions solely based on data from its adjacent neighbors and itself.

Figure 9A:
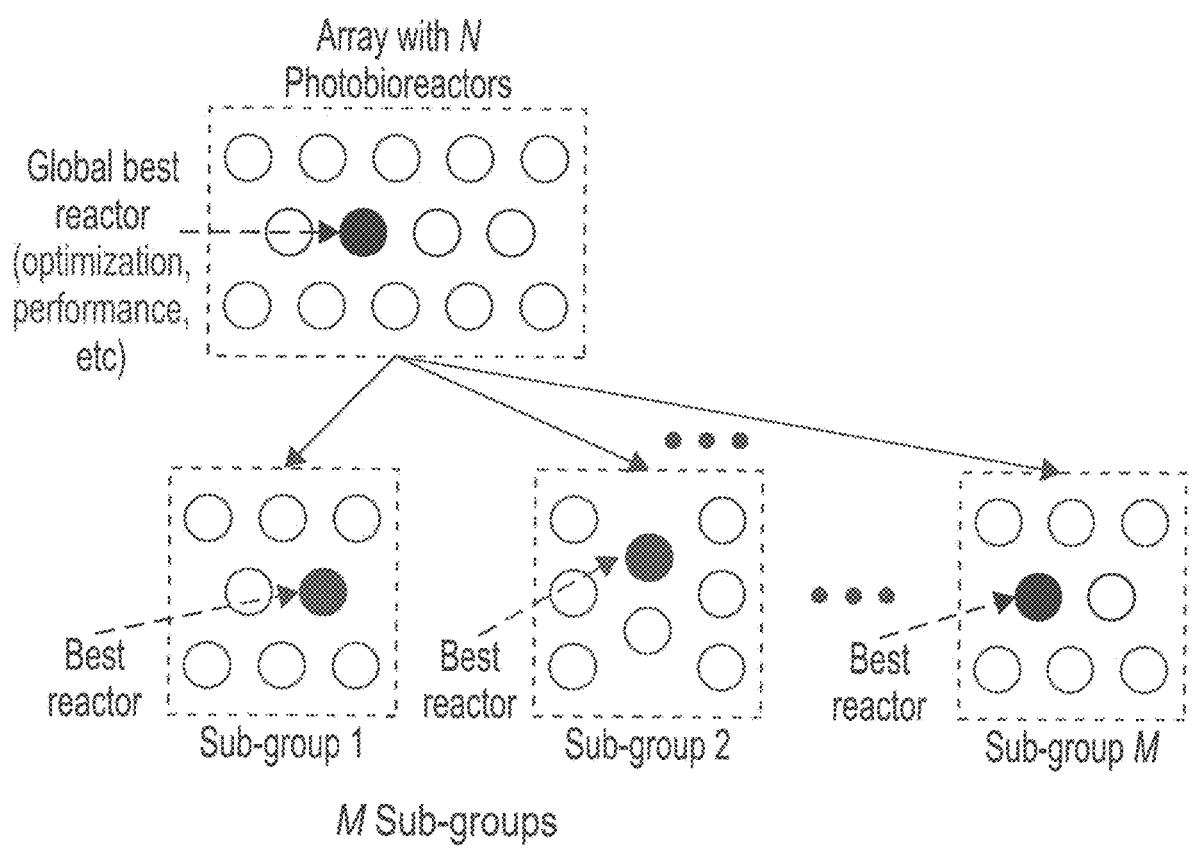
FIGS. 9A and 9B are schematic diagrams showing an optimization process based on an "internal feedback" concept performed by a control system having multiple photobioreactors in accordance with embodiments of the present disclosure.
Figure 9B:
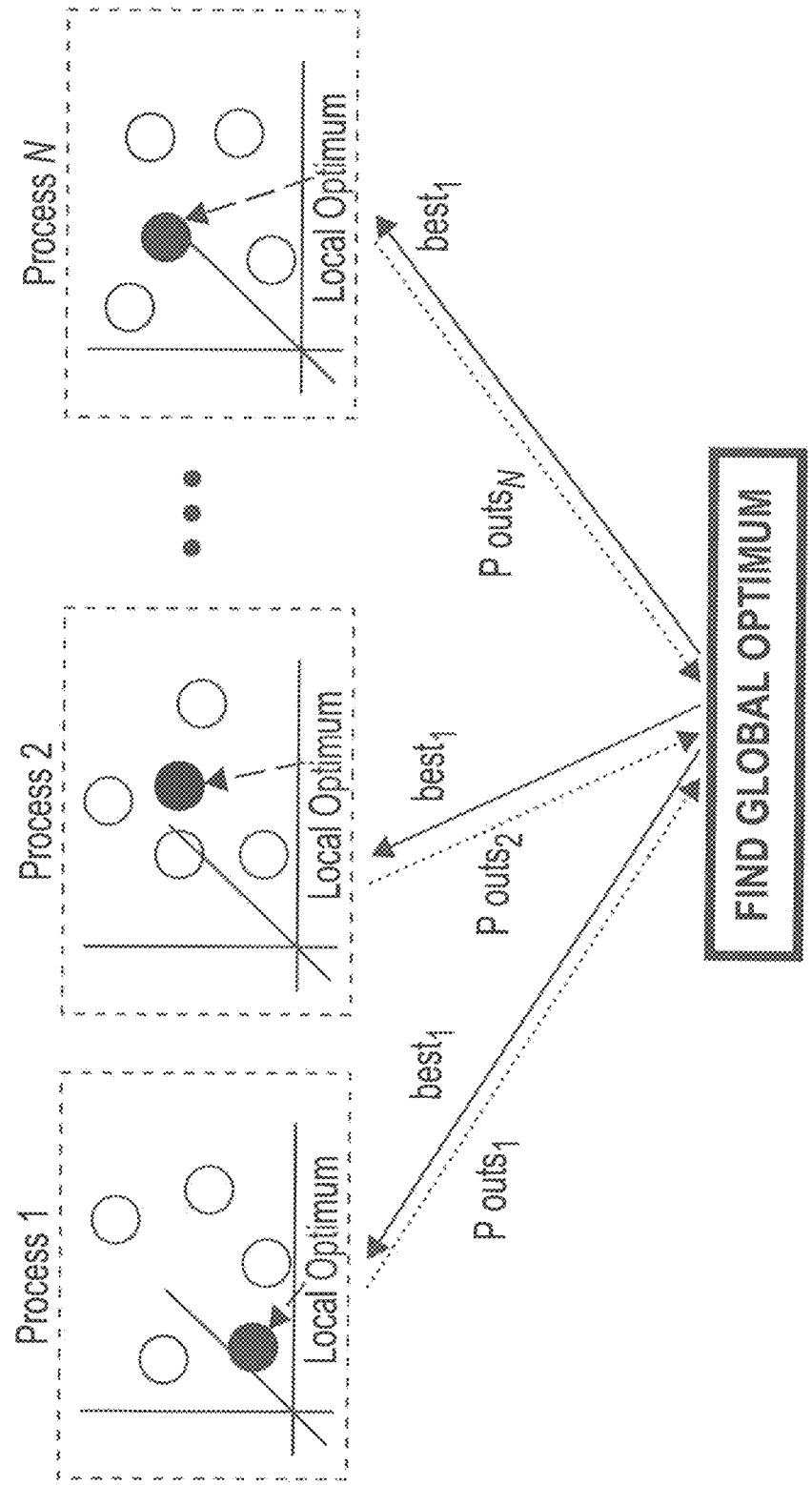

For example, FIGS. 9a and 9b are schematic diagrams showing an optimization process based on an "internal feedback" concept performed by a control system having multiple photobioreactors in accordance with embodiments of the present disclosure. As shown in FIG. 9b, the system can determine a local optimum (e.g., maximize production in a certain period of time) for each sub-group, and then provide the result to a higher level (e.g., global level shown in FIG. 9). The system can then determine a global optimum. By this arrangement, the system can operate the multiple photobioreactors to achieve various goals or objects at various group levels (e.g., achieve a global object of maximum production, and a local optimum of lowest energy consumption for a sub-group).

Some embodiments of the photobioreactor system may be comprised of a combination of top-down AI and swarm control. In such embodiments, the low-power swarm control may make decisions about individual photobioreactor behaviors to maintain normal operations, while the top-down AI may make broader decisions in order to optimize for particular circumstances or goals, or to react to more widespread stimuli.

Figure 10:
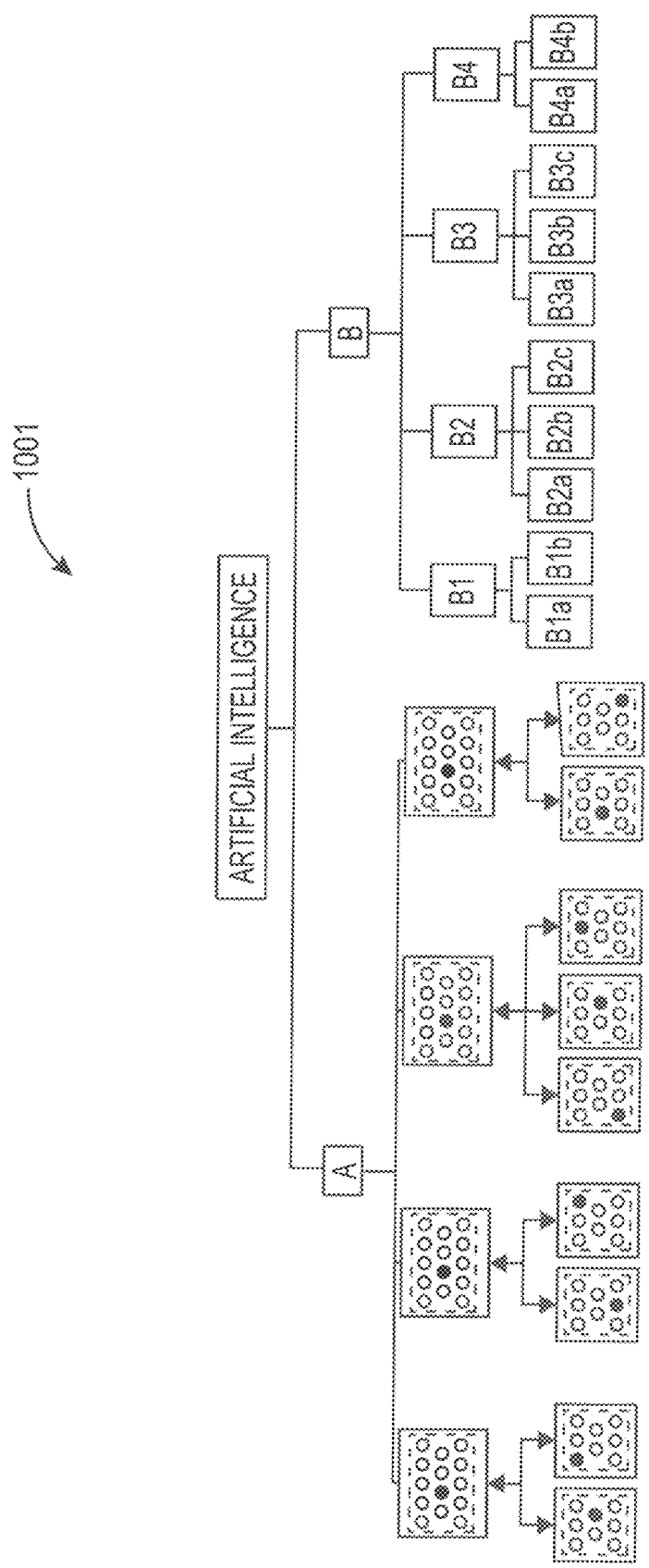
FIG. 10 is a schematic diagram showing a control system for multiple photobioreactors using both an "internal feedback" optimization process and a "top-down" AI approach.

For example, FIG. 10 is a schematic diagram showing a control system 1001 for multiple photobioreactors using both an optimization process and a "top-down" AI approach. As shown, the control system 1001 can perform local optimization within group A, and then apply the top-down approach in a higher level (e.g., for both Groups A and B). by this arrangement, the system provides an operator flexibility to manage the multiple photobioreactors to achieve various goals or objects.

In an embodiment of the distributed photobioreactor network, one or more data processing and/or management systems may be interconnected to form a substantially distributed network of photobioreactors from which data can be aggregated individually, in groups or from the full platform. Data transfer in such a system may occur between one or more photobioreactors or photobioreactor modules, between one or more downstream control systems, or between both photobioreactors and control systems, and may use substantially hard-wired connections, substantially wireless connections, or a combination of hard-wired and wireless connections.

In some embodiments, one or more processing units may provide the ability to combine incoming data, to manage outgoing data, and/or to transmit data to later-stage control systems. The processing units may be further characterized by the capability for autonomous analysis and/or autonomous decision-making regarding photobioreactor performance. In some embodiments, the processing units may be incorporated into the structure of the light source or the interior vessel, which may provide additional temperature remediation capabilities.

In one embodiment, the photobioreactor control systems may comprise one or more sensors. In some embodiments, the sensors may be integrated into the reactor housing or structure. For example, sensors may be integrated into the reactor housing using additive manufacturing, such as the selective deposition of conductive printing feedstock.

Figure 11:
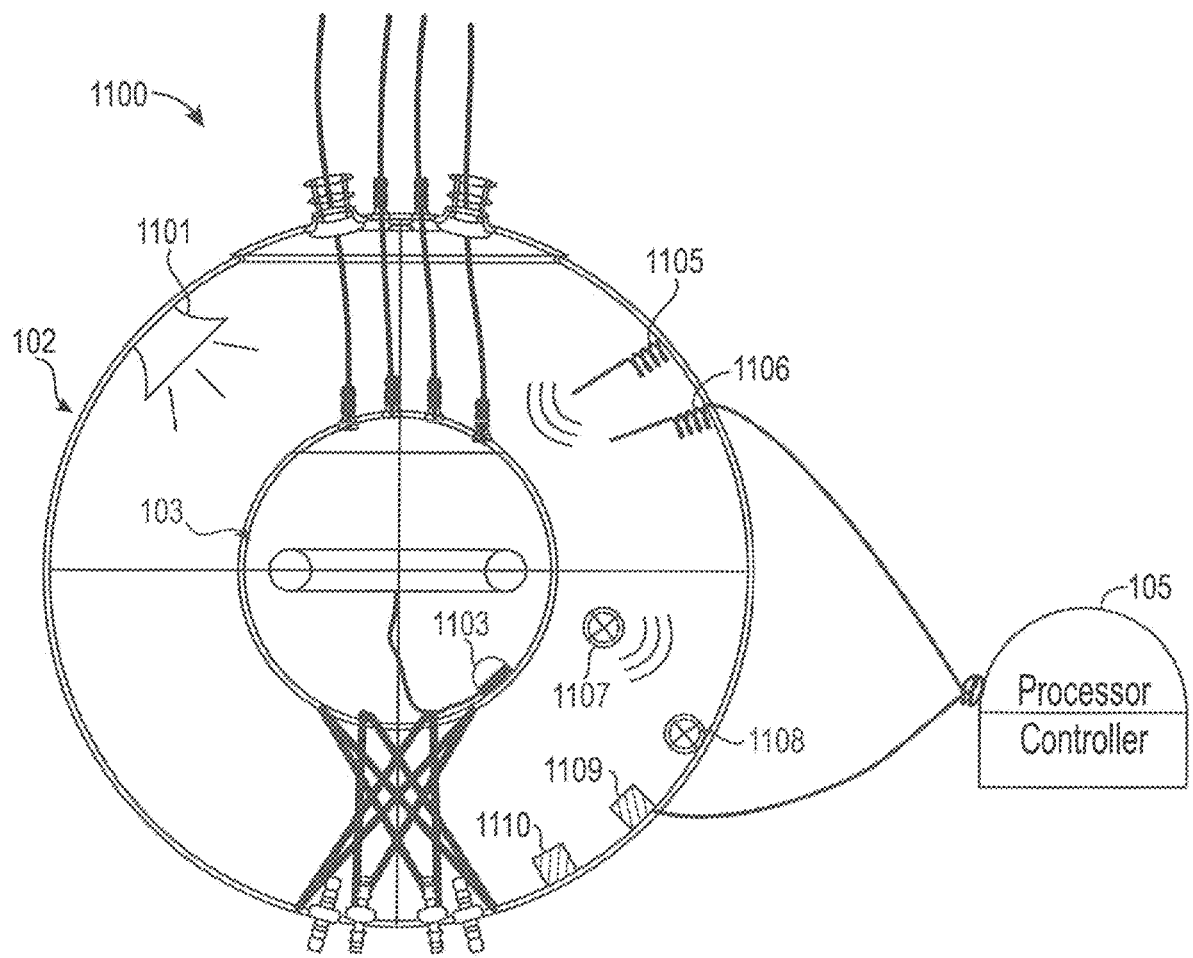
FIG. 11 shows a spherical-shaped photobioreactor in accordance with embodiments of the present disclosure.

For example, FIG. 11 shows a spherical-shaped photobioreactor 1100 in accordance with embodiments of the present disclosure. In the illustrated embodiments, the photobioreactor 1100 includes an outer vessel 102, an inner water-submersible system 103, and a control system 105. The photobioreactor 1100 includes a light source 1101 positioned on an interior surface of the outer vessel. A photometer sensor 1109 can be positioned on the interior surface of the outer vessel opposite the light source 1101 (such that the photometer sensor 1109 can measure the light passing through the outer vessel such that a status of the working fluid therein can be determined or measured; the status can then be transmitted to the control system 105 via a wired connection). In some embodiments, a photometer sensor 1110 can be integrated into the outer vessel. As also shown, an antenna 1105 can be attached to the interior surface of the outer vessel. In some embodiments, an antenna 1106 can be embedded in (a wall of) the outer vessel (and communicate with the control system 105 via a wired connection). An acoustic sensor 1108 can be positioned on the interior surface of the outer vessel and configured to measure a status of the working fluid in the outer vessel (the status can be transmitted to the control system 105 via a wired/wireless connection). An ultrasonic sensor can float in the working fluid in the outer vessel and be configured to measure a status of the working fluid in the outer vessel (the status can be transmitted to the control system 105 via a wireless connection). As shown in FIG. 11, a microprocessor 1103 can be attached to or positioned in the inner water-submersible system and configured to control the bioreactor 1100.

In some embodiments, data collected from the sensors may be used to determine the type, quantity and/or density of components in the culture or the culture media itself. For example, one or more sensors may be positioned on one side of the vessel, with a controlled light source on the opposite side of the vessel, such that the light source may send a fixed number of photons in the direction of the sensors from one side of the vessel across the culture to the other side of the vessel. In a further embodiment, one or more sensors may detect the number of photons that cross the culture from one side of the vessel to the other. In another embodiment, one or more sensors may be able to detect the fluorescent response of the organism(s) suspended in the culture. In another embodiment, one or more sensors may be able to differentiate reactive protein from total protein.

In some embodiments, the data collected from the sensors may be used by one or more systems, for example the photobioreactor control system, with the ability to detect harmful algal blooms (HABs) such as, for example, toxin screening, liquid chromatography, mass spectrometry, in vivo or in vitro bioassays, real-time quantitative polymerase chain reaction (qPCR) and other molecular probing techniques, or similar chemical or biological sensors. In some embodiments, data collected from the sensors may be used to infer the growth and health of the culture, the presence of photosynthetic invaders, and/or the presence of cell lysis. In further embodiments, data collected from the sensors may be used to infer a measurement of light performance.

In one embodiment, a photobioreactor disclosed herein may comprise an integrated photometer, characterized by the ability to detect the actual quantity of photons emitted compared to their expected performance over time. In some embodiments, the integrated photometer comprises two or more points of detection, such that the differential between the two or more points can be used to infer measurements of reactor performance. For example, the differential between measurements of physical airflow at two or more points may be used to infer energy added to the system for mixing and natural convection; the differential between measurements of $CO_2$ uptake at two or more points may be used to infer organism growth rate; or the differential between measurements of $O_2$ output at two or more points may be used to infer organism growth rate.

In one embodiment, a photobioreactor disclosed herein may comprise radar sensing and/or magnetic field detection technology, characterized by the use of one or more antennae. In some embodiments, the radar system may also comprise one or more transmitters. In some embodiments, the antenna(e) may be embedded in the wall of the reactor housing. In some embodiments, data collected by the antenna(e) may be used to infer, for example, cellular growth, protein content, carbohydrate content, presence of an infection or contaminant, total dissolved solids, fluid flow, or system integrity. In another embodiment, the method for sensing or detection may be characterized by the use of specific transmission frequencies. In another embodiment, the method for sensing or detection may be characterized by the deformation of wave forms at two or more frequencies. In another embodiment, the method for sensing or detection may be characterized by the use of signal deflection between transmission and reception points on the X, Y and Z poles of the reactor.

One or more photobioreactor control systems may comprise one or more sensors for collecting data from the water-submersible system for converting electrical energy into electromagnetic radiation or the interior volume of the interior vessel. In some embodiments, one or more microprocessors and other corresponding electronics may be located in or connected to the interior vessel volume. In an embodiment, one or more microprocessors and corresponding electronics may provide for individual control of one or more light sources. In another embodiment, one or more microprocessors may provide for system monitoring.

One or more photobioreactor control systems may perform the function of culture monitoring characterized by, for example, the use of probes (e.g., chemical or gas), sensors (e.g. temperature, light, pressure, flow rate, sound, etc.), conductivity testing or embedded spectrophotometry to measure Nitrogen content, Phosphorous content, Potassium content, gas composition (e.g., dissolved $O_2$, dissolved $CO_2$), presence of sugars, or presence of waste products. For example, the culture control system or systems may monitor culture temperature, interior vessel volume temperature, gas flow rates, liquid flow rates, and/or liquid levels. In some embodiments, the culture control system(s) may comprise acoustic and/or ultrasonic sensing components.

In various embodiments, the photobioreactor disclosed herein may comprise one or more culture extraction and/or manipulation systems. In one embodiment, the photobioreactor comprises a system for concentration of and initial de-watering of a culture prior to harvest. In some embodiments, the culture extraction and/or manipulation system(s) may allow for steady-state continuous production, for example by enabling depleted media and culture to be taken away without impacting culture density, and/or allowing for media additions without impacting culture density.

The culture extraction and/or manipulation system(s) may comprise one or more electric or electronic motors, pumps, conduit and valves. In some embodiments, the culture extraction and/or manipulation system(s) may be characterized by the use of electronically controlled valves. In other embodiments, one or more of the valves may be connected to a collection spigot comprising an inlet and an outlet, such that the valves may be used to facilitate the removal of mature culture and/or nutrient-depleted media.

Figure 12:
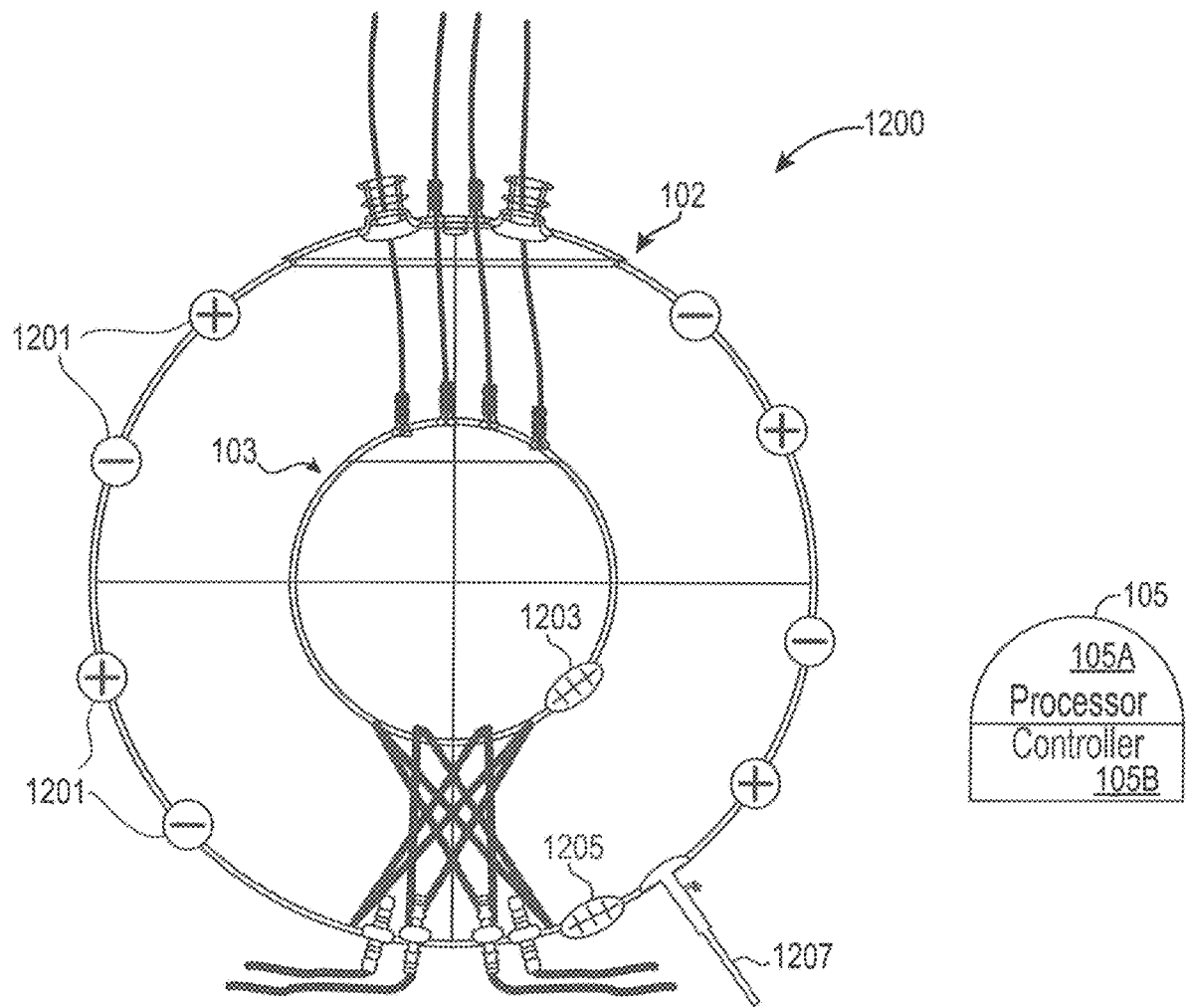
FIG. 12 shows a spherical-shaped photobioreactor in accordance with embodiments of the present disclosure.

For example, FIG. 12 shows a spherical-shaped photobioreactor 1200 in accordance with embodiments of the present disclosure. As shown in FIG. 12, the photobioreactor 1200 includes an outer vessel 102, an inner water-submersible light source 103, and a control system 105. The photobioreactor 1100 includes multiple distributed positive/negative conductors 1201 positioned in various locations of the outer vessel 102. The conductors 1201 are configured to receive different electrical charges such that an operator can manipulate the working fluid in the outer vessel 102. For example, the operator can generate/change a flow of the working fluid by applying electrical charges at one or more of the conductors 1201. As also shown, a pump 1203 can be integrated into the water-submersible light source 103. Another pump 1205 can be integrated into or embedded in the outer vessel 102. A collection spigot 1207 can be integrated into or embedded in the outer vessel 102 and configured to enable an operator to collect the working fluid in the outer vessel 102. In addition, the photobioreactor 1200 can include multiple inlets and outlets configured to deliver the working fluid.

Figure 13:
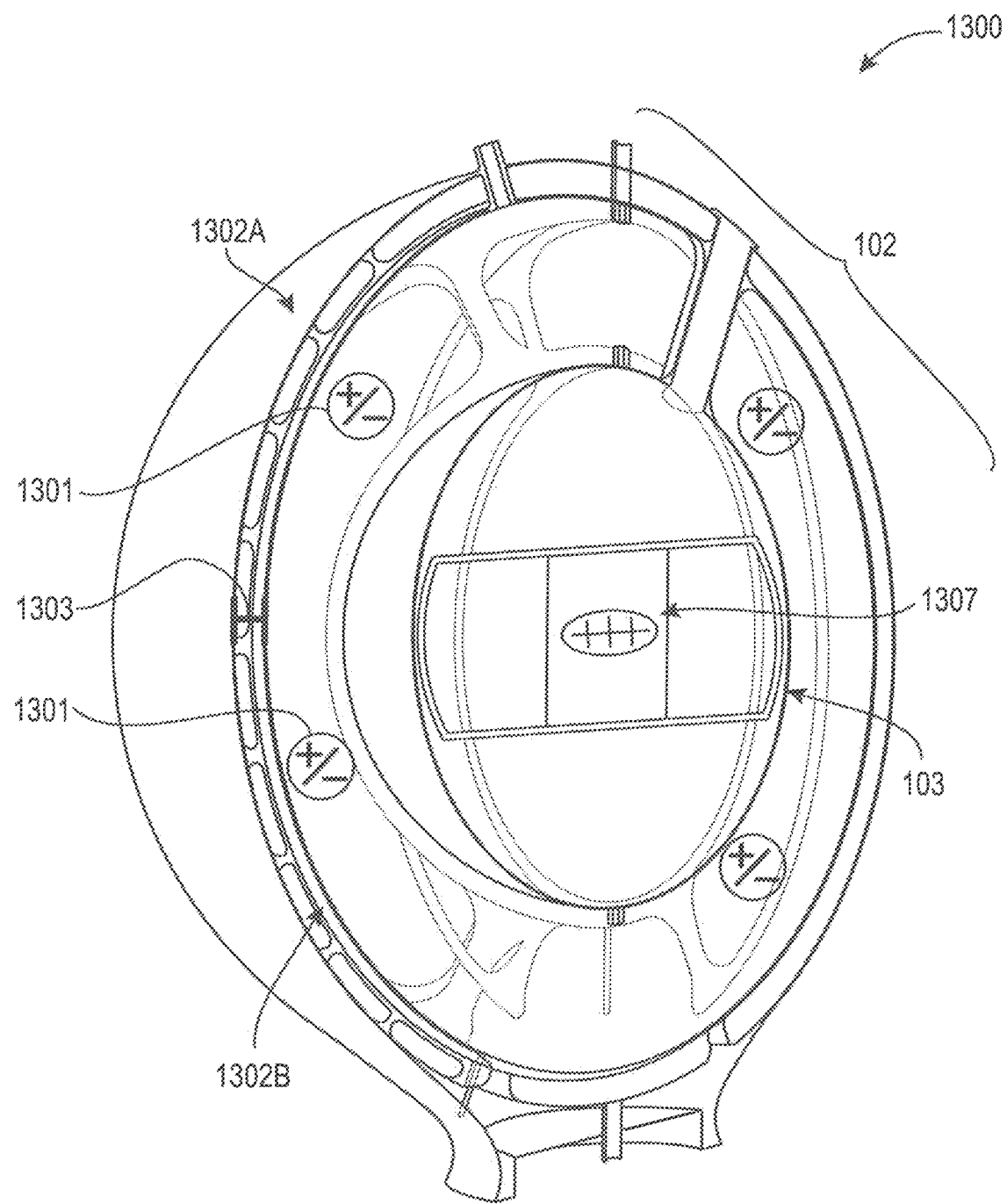
FIG. 13 shows a photobioreactor with a dual-wall design in accordance with embodiments of the present disclosure.

In some embodiments, the substantially spherical vessel wall may comprise an inner wall and an outer wall having a double-walled configuration. In one such embodiment, that outer wall may comprise a watertight or water-impermeable wall, while the inner wall may be a porous or semi-permeable wall. In one embodiment, a void exists between the exterior and interior walls. The interior wall may be constructed with additive manufacturing processes using porous or semi-permeable materials. For example, FIG. 13 shows a photobioreactor 1300 with a dual-wall design in accordance with embodiments of the present disclosure. The photobioreactor 1300 includes an outer vessel 102, and an inner water-submersible toroid light source 103. The photobioreactor 1300 includes multiple distributed electro-magnets 1301 positioned in various locations of the outer vessel 102. The electro-magnets 1301 are configured to manipulate the working fluid in the outer vessel 102. As also shown, a pump 1307 can be integrated into the water-submersible toroid light source 103. The outer vessel 102 includes an outer wall 1302A and an inner wall 1302B. Between the outer and inner walls is a void 1303 configured to provide insulation for the outer vessel 102. In some embodiments, the outer wall can be a watertight structure/layer, and the inner wall can be a semi-permeable structure/layer.

In some embodiments, the culture manipulation/extraction systems(s) may allow introduction of electricity into the culture. For example, electricity may be introduced substantially using a system of distributed positive and negative conductors (anode/cathode), using a system of distributed electromagnets or using a wireless power transfer system.

In some embodiments, the culture manipulation/extraction system(s) may comprise a mixing system. In one embodiment, such a mixing system provides culture mixing or agitation independently of gas introduction. In some embodiments, the culture mixing system(s) comprises a wide distribution of inlets and/or a wide distribution of outlets. In some embodiments, the culture mixing system(s) may comprise one or more pumps, wherein the one or more pumps are embedded into the vessel wall. In one embodiment, one or more pumps may be integrated into the light source. In another embodiment one or more pumps may be thermodynamic. In some embodiments, one or more pumps may be integrated into the inner ring of a toroid light source.

The photobioreactors described herein may comprise one or more systems for media and chemical addition or removal, or for the addition of individual components to the culture. In some embodiments, media and/or chemical additions may occur at a single point of introduction. In other embodiments, two or more points of introduction may be used, which may be further characterized by the formation of a network of micro-channels. In a further embodiment, the network of micro-channels may be embedded into the vessel wall and/or into the support structure for the light source. In some embodiments, the method of media or chemical addition or distribution may be achieved by the use of electronically controlled valves. The system(s) may use data provided by one or more sensing or monitoring systems to infer the quality and/or nutrient value of incoming media.

Figure 14:
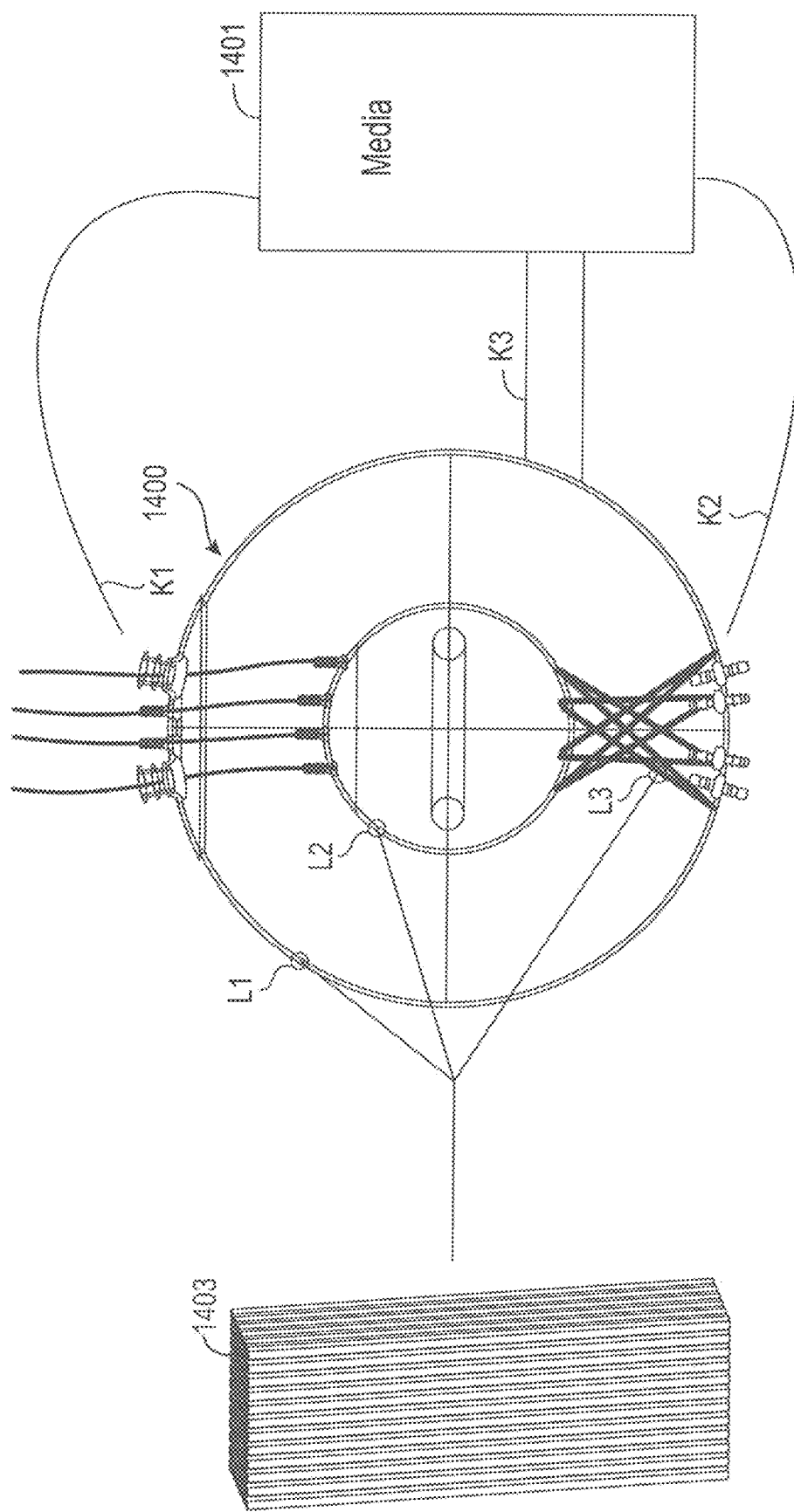
FIG. 14 shows a photobioreactor and a media/chemical system in accordance with embodiments of the present disclosure.

FIG. 14 shows a photobioreactor 1400 and a media/chemical system 1401 in accordance with embodiments of the present disclosure. The media system 1401 is configured to supply materials for producing biomass to the photobioreactor 1400. As shown, the media system 1401 can be in fluid connection with the photobioreactor 1400 at various locations (e.g., K1, K2 and/or K3). The photobioreactor 1400 can include a micro-channels component 1403 configured to function as an "entry point" for adding media or chemicals in the photobioreactor 1400. In some embodiments, the micro-channels may also allow for mixing or aeration of media or chemicals. As shown, the micro-channels component 1403 can be positioned at various locations of the photobioreactor 1400 (e.g., embedded in a vessel wall indicated as L1, embedded in the inner vessel wall indicated as L2 and/or embedded in a supporting structure indicated as L3).

The photobioreactors described herein may further comprise one or more systems to facilitate media sterilization. For example, in some embodiments media sterilization may be accomplished by the use of in-line irradiation using ultraviolet or near-ultraviolet radiation, microwave radiation, and/or thermal sterilization methods. In other embodiments, media sterilization may be accomplished by the use of membrane or porous filtration methods, through the use of biological filtration methods such as diatomic (diatomaceous) earth, or through the use of chemical sterilization media.

The photobioreactors described herein may also comprise a cleaning system for removing (cleaning) the cultivated and/or propagated photosynthetic organisms from the vessel, from the light source, or from other photobioreactor components. In some embodiments, the cleaning system may comprise one or more cleaning units that may be mounted within the interior vessel volume or on the outside surface of the water-submersible system for converting electrical energy into electromagnetic radiation. In some embodiments the cleaning system comprises a device with a suction component, a filtration component and an expulsion component to take in media from the interior vessel volume, filter the media, and expel the cleaned media back into the interior vessel volume. In some embodiments, the cleaning unit or units may comprise a robot with the capability for both suction and expulsion such as, for example, to recirculate culture through the robot body. In further embodiments, one or more cleaning robots may have non-rigid bodies and/or may be gas operated. In another embodiment, the cleaning system may comprise one or more cleaning unit actuators.

Figure 15:
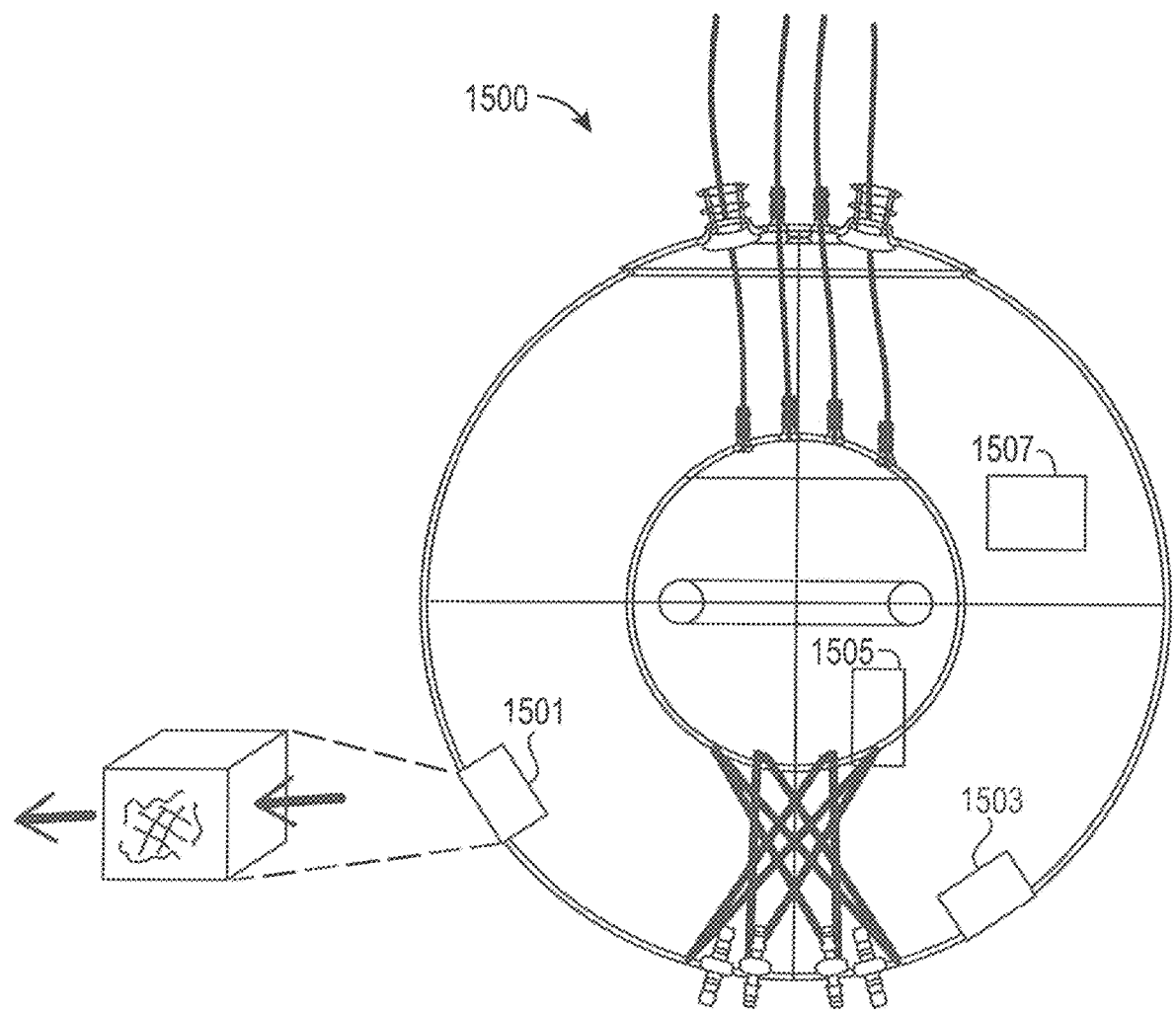
FIG. 15 shows a photobioreactor and one or more cleaning units in accordance with embodiments of the present disclosure.

For example, FIG. 15. shows a photobioreactor 1500 and one or more cleaning units in accordance with embodiments of the present disclosure. In some embodiments, the cleaning unit 1501 can be attached to or embedded in a vessel wall of the photobioreactor 1500. In some embodiments, the cleaning unit comprises a cleaning actuator 1503, which may be attached to or embedded in the vessel wall of the photobioreactor 1500. In some embodiments, the cleaning unit 1505 can be attached to or embedded in an inner wall of the photobioreactor 1500. In some embodiments, the cleaning unit can be a floating cleaning unit 1507 floating in the working fluid in the photobioreactor 1500.

The present disclosure comprises a method of converting electrical energy into electromagnetic radiation (light source), wherein the water-submersible system for converting electrical energy into electromagnetic radiation may be substantially spherical, such that electromagnetic radiation may be directed to substantially any location in the substantially spherical vessel, and the water-submersible system for converting electrical energy into electromagnetic radiation may be capable of functioning reliably when submerged in liquid such as, for example, the culture in which the photosynthetic organisms are cultivated and/or propagated. In some embodiments, the water-submersible system for converting electrical energy into electromagnetic radiation comprises a barrier having a substantially toroidal shape.

Figure 16:
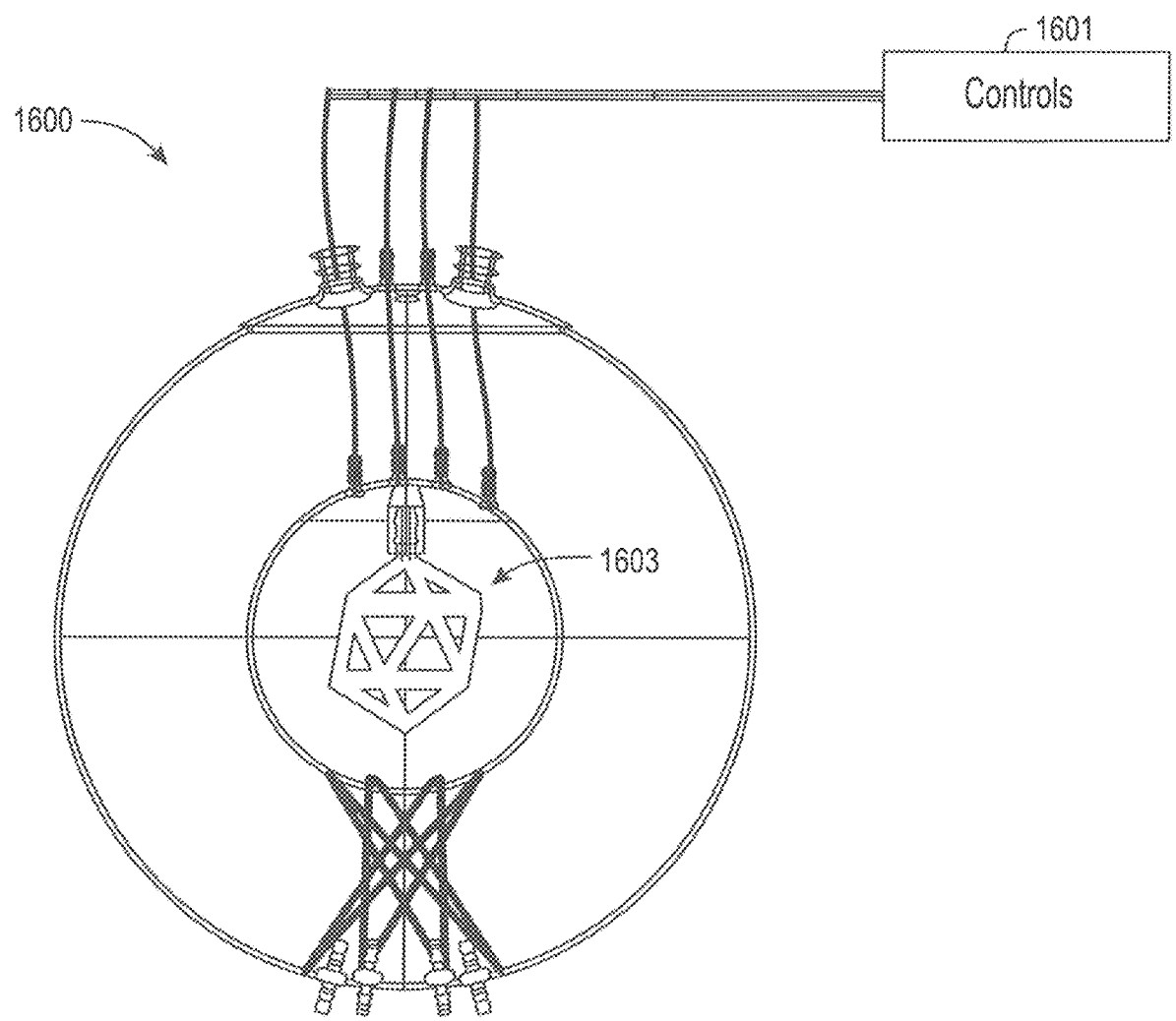
FIG. 16 shows a photobioreactor with a spherical light source in accordance with embodiments of the present disclosure.

FIG. 16 shows a photobioreactor 1600 with a spherical light source 1603 in accordance with embodiments of the present disclosure. A power supply or control 1601 provides electricity to the spherical light source 1603 and then the spherical light source 1603 can emit light toward any locations inside photobioreactor 1600. The spherical light source 1603 includes a rigid scaffolding structure which defines an internal volume and which enhances the durability of the spherical light source 1603.

In some embodiments, the light source described herein may comprise a plurality of circuit boards, each comprising at least three edges, arranged in a substantially spherical or toroidal shape defining an interior light source volume, wherein the plurality of the circuit boards comprise a first surface in contact with the interior light source volume and an opposing second surface comprising light emitting diodes (LEDs). In some embodiments, the circuit boards may be flexible, such that one of more flexible circuit boards may be bent, curved and/or assembled to form the substantially spherical light source. In some embodiments, one or more circuit boards may be assembled using a rigid, semi-rigid or flexible scaffolding, such as, for example, a plastic scaffolding. In further embodiments, this scaffolding may be substantially produced using additive manufacturing processes. The light source described herein may also comprise one or more organic light emitting diodes (OLEDs), carbon nanotubes, diatoms, or a combination of components capable of converting electrical energy into electromagnetic radiation.

The light source described herein may be used to convert electrical energy into electromagnetic radiation within the visible spectrum, such as, for example, photosynthetically active radiation (PAR). The light source described herein may also be used to convert electrical energy into electromagnetic radiation outside the visible spectrum, such as, for example, ultraviolet (UV) or infra-red (IR) light. In some embodiments using UV or IR light sources, the UV or IR radiation may be used for the purposes of growing organisms designed to photosynthesize outside the normal PAR spectrum. In other embodiments using UV or IR light sources, the UV or IR radiation may be used for sterilization purposes, such as to sterilize the liquid media or internal components in the vessel, or to heat the liquid media in the vessel.

In some embodiments, the radiation may be optimized to increase the likelihood of photon absorption by the organism or organisms. For example, radiation manipulation may be characterized by the use of pulse-width modulation (PWM). In another example, radiation manipulation may be characterized by the incorporation of materials or meta-materials with the capability to manipulate light at a macroscopic, particle and/or quantum level into the external surface of the light source barrier. In another example, radiation manipulation may be characterized by the use of optical structures with the ability to twist light, such as through the incorporation of one or more lenses or reflectors, or through the use of additive manufacturing materials and processes.

In some embodiments, radiation manipulation may be characterized by the incorporation of materials or meta-materials with the capability to bounce photons into the culture, such as, for example, reflective or refractive surface coatings, inherently reflective materials, or embedded particulates such as aluminum nanoparticles or quantum dots. Such materials or meta-materials may be incorporated into one or more bioreactor components or applied to one or more culture-facing surfaces, for example through additive manufacturing processes. In various embodiments, the materials or meta-materials may have the ability to direct photons into the culture at oblique angles to the direct angle of light source emission, and/or they may be capable of discrete manipulation of the photons.

Figure 17:
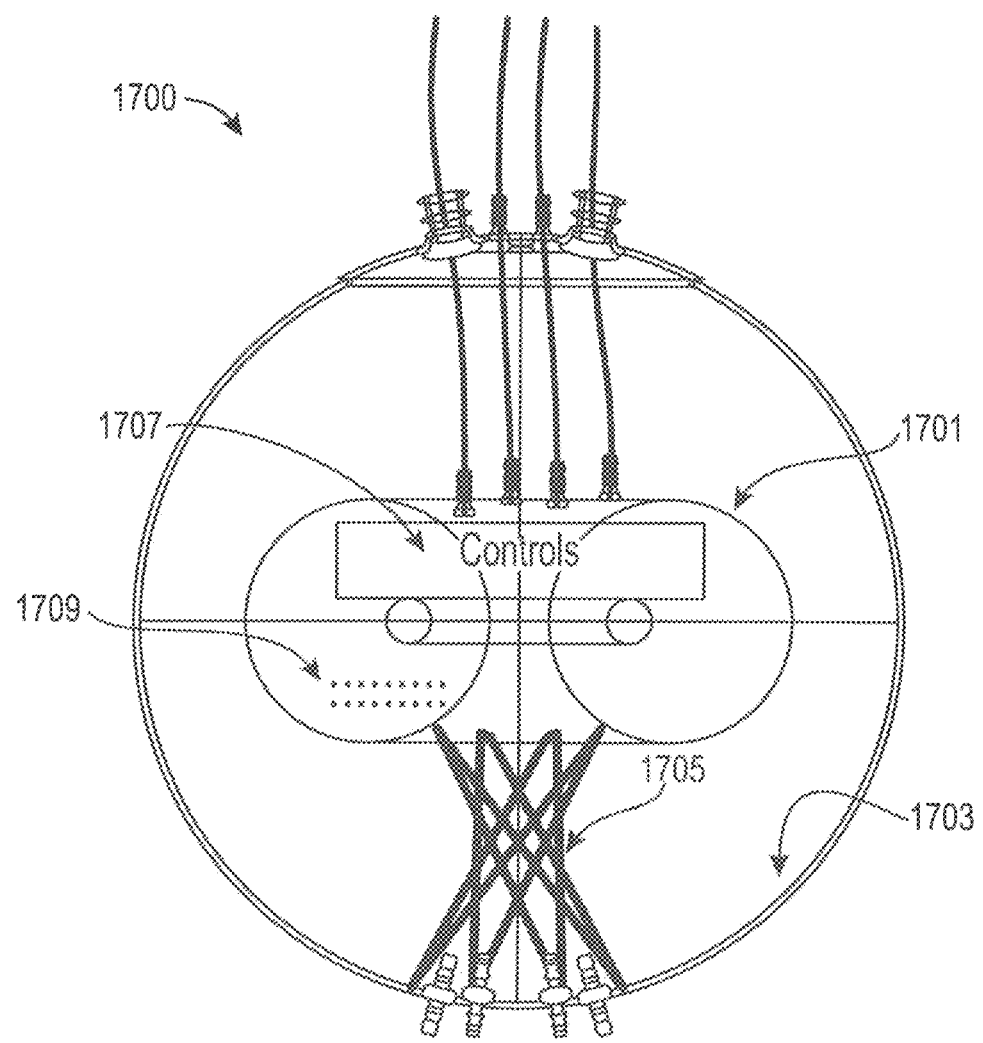
FIG. 17 shows a photobioreactor in accordance with embodiments of the present disclosure.

FIG. 17 shows a photobioreactor 1700 with a toroid light source 1701 and a reflective surface coating 1703 in accordance with embodiments of the present disclosure. The toroid light source 1701 is configured to emit light rays or photons outwardly toward the working fluid. After the light rays pass through the working fluid, these rays or photons can be reflected/directed back to the working fluid by the reflective surface coating 1703. The photobioreactor 1700 also includes reflective material 1705 coated on a support structure and particles 1709 embedded in the toroid light source 1701. The particles 1709 and the reflective material 1705 can also reflect/direct light rays. By this arrangement, the photobioreactor 1700 can fully utilize the light rays or photons by keeping them in the photobioreactor 1700 as long as possible, and can also maximize the number of organisms in the working fluid that come in contact with each light ray or photon The light source described herein may comprise a connection to one or more digital controls. In some embodiments, the digital controls may be incorporated into the core vessel volume.

The photobioreactor described herein may comprise one or more systems for gas addition and/or dispersion, wherein the gas or gases may include $O_2$, $CO_2$, methane, biogas, syngas, human or animal exhalant, and the like. The source of these gases may comprise ambient atmosphere, ratio-adjusted air, or a combination of sources. For example, ratio-adjusted air may comprise an increase or decrease of $CO_2$, or an increase or decrease of $O_2$. In some embodiments, the gas addition system may be characterized by the introduction of gas directly into the culture.

The gas addition and/or dispersion system(s) described herein may comprise one or more air manifolds for the purpose of providing a method for gas exchange, such as, for example, allowing $O_2$ to exit the culture while allowing $CO_2$ to enter the culture. The manifolds may be independent from the reactor vessel wall or walls, or they may be integrated into the reactor wall or walls, for example, through additive manufacturing or through some other manufacturing or assembly process.

Figure 18:
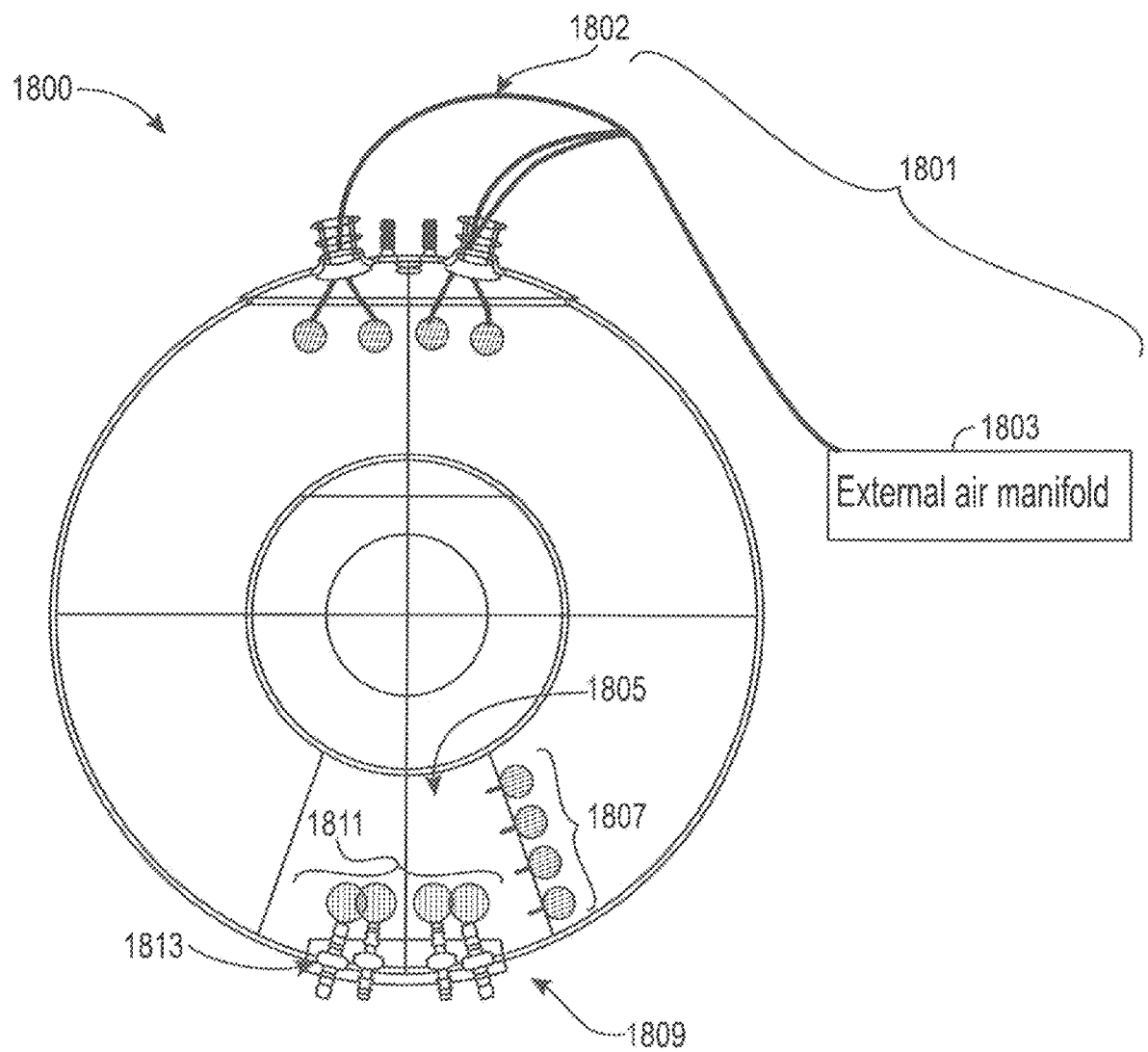
FIG. 18 shows a photobioreactor with a gas diffusion device/system in accordance with embodiments of the present disclosure.

FIG. 18 shows a photobioreactor 1800 with a gas diffusion device/system 1801 in accordance with embodiments of the present disclosure. The gas diffusion device/system 1801 is configured to deliver air/gas into the photobioreactor 1800. In some embodiments, the gas diffusion device 1801 can include an external air manifold 1803 configured to deliver air into the photobioreactor 1800 via multiple tubes 1802. In some embodiments, the gas diffusion device 1801 can deliver air into the photobioreactor 1800 via an air chamber or void 1805. In some embodiments, air/gas can be delivered into the photobioreactor 1800 via one or more gas diffusion devices such as air stones 1807, which can be integrated into a core support structure. In some embodiments, an air manifold 1809 can be integrated into an outer vessel wall of the photobioreactor 1800. In some embodiments, air/gas can be deliver into the photobioreactor 1800 via one or more spherical air stones 1811 comprising porous/semi-permeable materials. In some embodiments, the photobioreactor 1800 can include one or more valves 1813 to regulate the flow of air/gas.

The gas addition and/or dispersion system(s) described herein may comprise one or more components for dispersion of gases into the culture, such as air stones. The air stones may be substantially cylindrical, substantially spherical, substantially disc-shaped or substantially ring-shaped. The air stones may be constructed of or coated with a substantially porous or semi-permeable material, or they may be integrated into the reactor housing through additive manufacturing or through some other manufacturing or assembly process. In some embodiments, one or more air stones may be controlled using electronic valves, such that the valves may be opened or closed independently or in groups.

Porosity or permeability of any of the elements disclosed and described herein can be controlled by: Electrical signals sent to or distributed throughout the interior layer (for example, using conductive materials that are integrated into the porous or semi-permeable layer); Controlled variations in air pressure, such as pressure changes that cause one-way valves integrated into the pores to open or close; Constricting, flexing or relaxing of the material in response to temperature, chemical consistency or specific wavelengths of light.

In some embodiments, a plurality of air stones may be arranged in a substantially circular shape to form one or more rings or discs of varying diameter, or individual stones may be substantially circular or disc-shaped with varying diameters. In further embodiments, one or more rings or discs may be connected to an air chamber, such that redirecting the pressure between chambers causes moving or pulsed air introduction.

Figure 19:
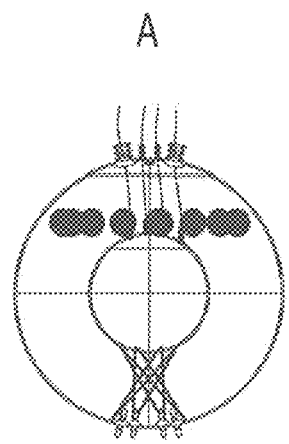
FIG. 19 describes various configurations of a gas diffusion system (using air stones as an example) in accordance with embodiments of the present disclosure.
Figure 19:
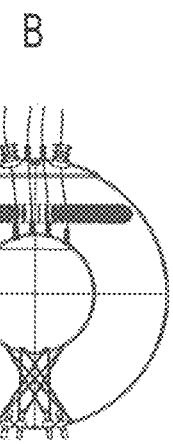
Figure 19:
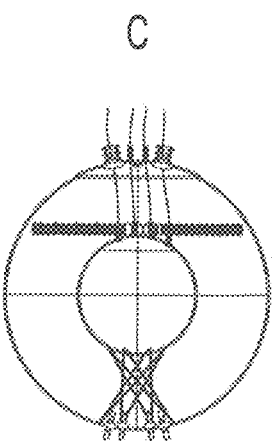
Figure 19:
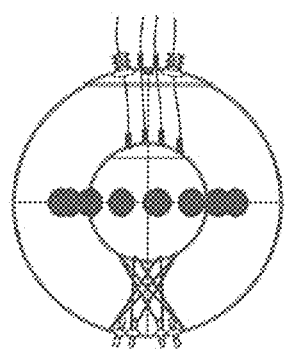
Figure 19:
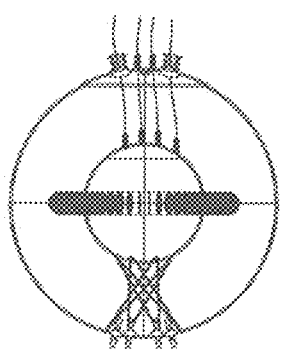
Figure 19:
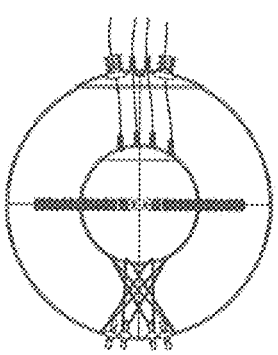
Figure 19:
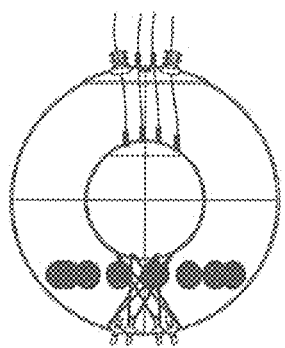
Figure 19:
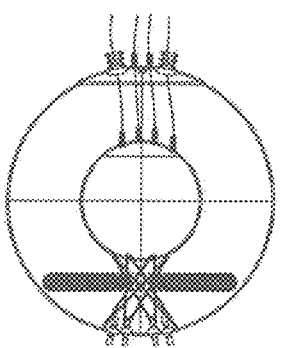
Figure 19:
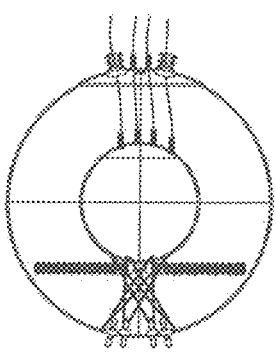

FIG. 19 describes various configurations of a gas diffusion system 1901 (using air stones as an example) in accordance with embodiments of the present disclosure. For example, the gas diffusion system 1901 can include (1) spherical air stones positioned at various heights (shown in column A), (2) disc-shaped air stones positioned at various heights (shown in column B); and/or (3) ring-shaped air stones positioned at various heights (shown in column C).

Figure 20:
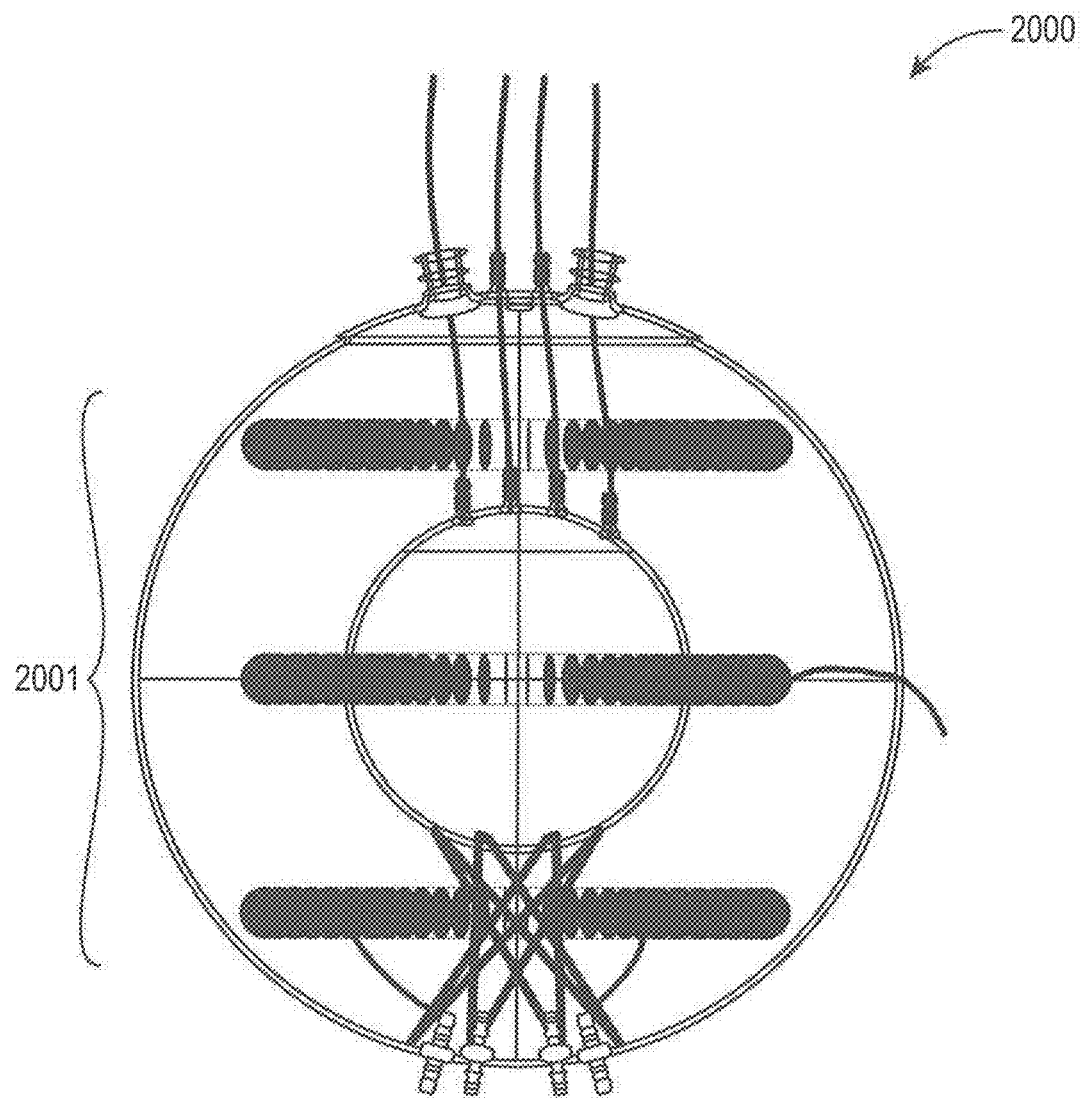
FIG. 20 shows a photobioreactor with a distributed gas diffusion system in accordance with embodiments of the present disclosure.

FIG. 20 shows a photobioreactor 2000 with an air-stone system 2001 in accordance with embodiments of the present disclosure. As shown, the air-stone system 2001 includes multiple layers of ring-shaped or disc-shaped air stones positioned at various heights in the photobioreactor 2000. The air stones are further coupled to an air chamber or air source via various air connections (e.g., ducts, pipes, etc.)

In some embodiments, the method of gas introduction and/or dispersion may comprise the use of one or more support structures or struts, which may also be used to support the water-submersible light source within the photobioreactor volume. The support structures or struts may be constructed with an internal void that may be used to store gases for addition to the culture, and they may comprise one or more air manifolds and/or one or more air stones to facilitate the addition and/or diffusion of gases into the culture.

In some embodiments, the method of gas introduction and/or dispersion may comprise the use of a double-walled outer housing, such that the outer barrier of the substantially spherical vessel comprises a watertight exterior wall, an interior wall, and a void between the exterior and interior walls. The interior wall may be constructed of a porous or semi-permeable material that allows for culture extraction and/or manipulation, including, for example, concentration and filtration of organisms. For example, the porous material may have a pore diameter small enough to keep individual cells on the inside of the reactor while allowing liquid to pass through to the void between the two walls. The void between the two walls may also allow for introduction of gas to the culture. In some embodiments, the permeability of the inner wall may be controlled substantially using air pressure.

The photobioreactor described herein may comprise one or more systems for temperature management. Various methods of temperature management may be utilized, including, for example, ambient temperature control, forced air cooling, or the use of one or more electrical heating elements. In some embodiments, temperature management may be achieved substantially through light source manipulation, for example through the use of controlled variations in frequency, or through controlled variations in power or intensity. In some embodiments, temperature management may be achieved substantially through the use of a cooling device such as a cooling jacket.

In some embodiments, the temperature management system may comprise heat dispersal fluid. The heat dispersal fluid may be optically clear, and it may comprise a non-conductive liquid such as, for example, mineral oil, or a non-conductive gel. In some embodiments, the heat dispersal fluid may comprise quantum dots or reflective particles. In other embodiments, the heat dispersal fluid may be characterized by the ability to emit light when exposed to heat.

Figure 21:
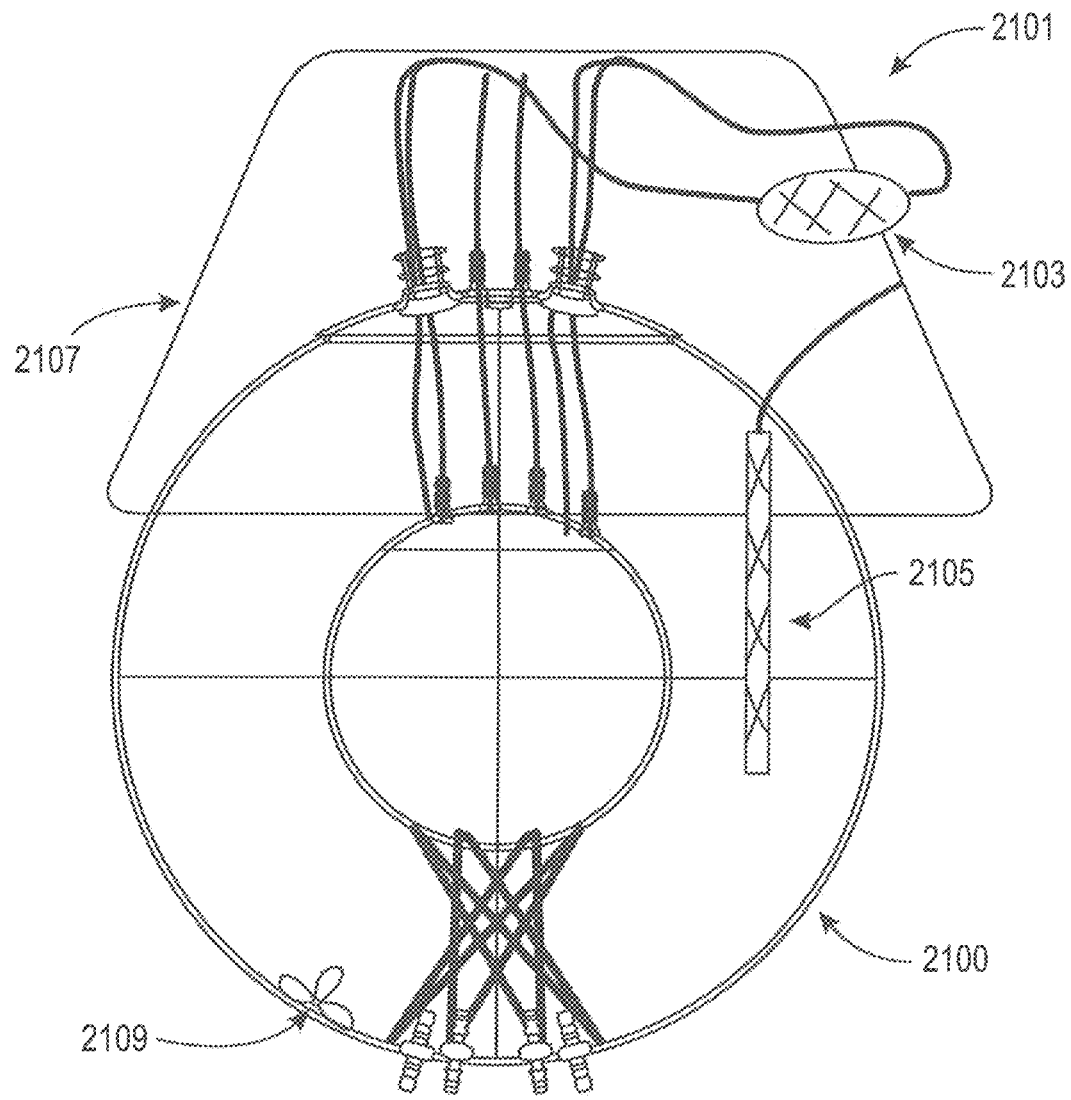
FIG. 21 shows a photobioreactor with a temperature management system in accordance with embodiments of the present disclosure.

FIG. 21 shows a photobioreactor 2100 with a temperature management system 2101 in accordance with embodiments of the present disclosure. The temperature management system 2101 is configured to manage the temperature of the photobioreactor 2100. In some embodiments, the temperature management system 2101 can include an external pump 2103 (e.g., to power and/or direct the circulation of the heat dispersal fluid, or to deliver coolant or refrigerant), and an electrical heating element 2105 positioned inside the photobioreactor 2100 and configured to transfer heat to, or absorb heat from, the working fluid inside the photobioreactor 2100. The temperature management system 2101 can also include a cooling jacket 2107 positioned to reduce the temperature of the photobioreactor 2100. In some embodiments, the temperature management system 2101 can include a fan 2109 (e.g., a gyroscopic fan) configured to enhance flow/circulation/ventilation of fluid inside the photobioreactor 2100.

Figure 22:
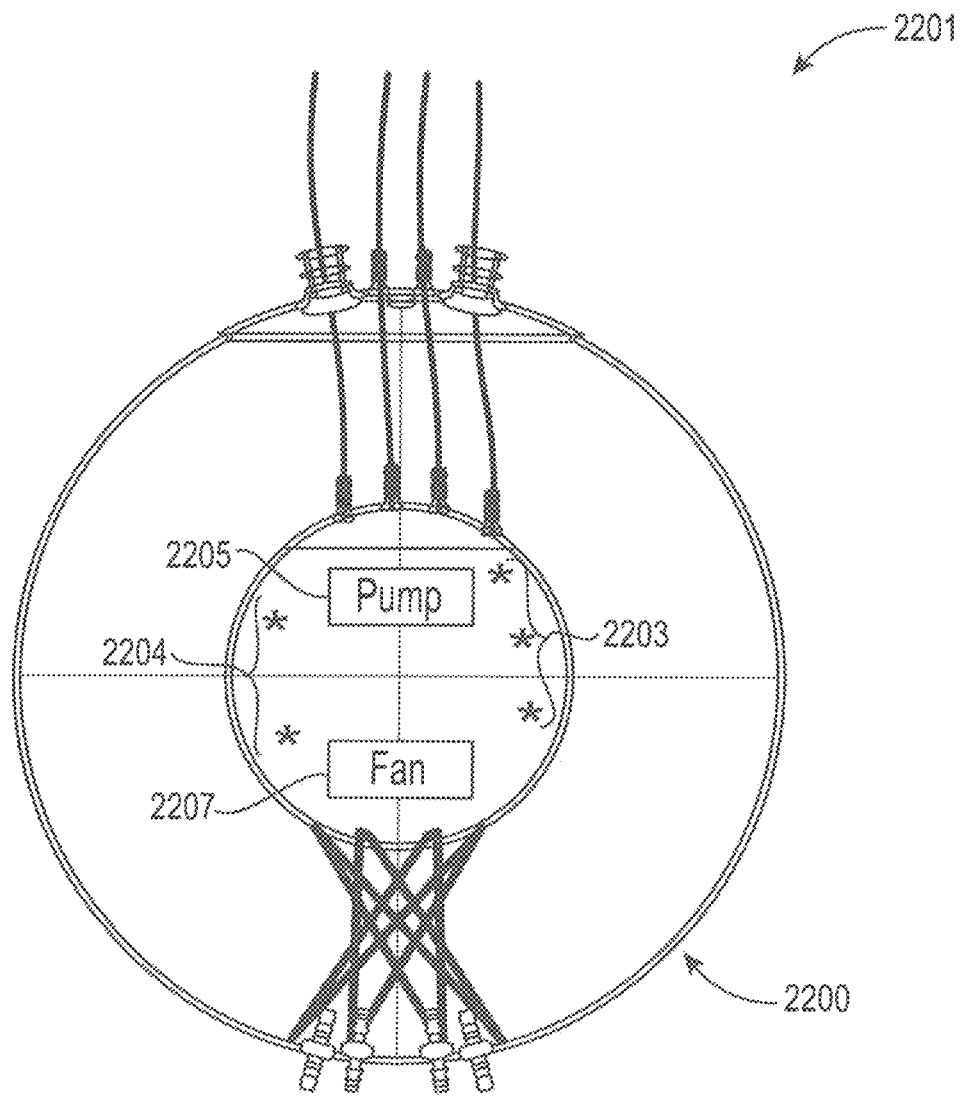
FIG. 22 shows a photobioreactor with a temperature management system in accordance with embodiments of the present disclosure.

FIG. 22 shows a photobioreactor 2200 with a temperature management system 2201 in accordance with embodiments of the present disclosure. The temperature management system 2201 is configured to manage the temperature of the photobioreactor 2200. In some embodiments, the temperature management system 2201 can include a heat dispersal fluid containing quantum dots 2203 or reflective particles 2204 positioned in an inner vessel of the photobioreactor 2200. In some embodiments, the temperature management system 2201 can include a fluid pump 2205 positioned at or incorporated in the inner vessel of the photobioreactor 2200. In some embodiments, the temperature management system 2201 can include a gyroscopic fan 2207 positioned at or incorporated in the inner vessel of the photobioreactor 2200

In some embodiments, temperature management may be achieved substantially through the recirculation of heat dispersal fluid inside the interior vessel volume. Recirculation may be achieved using one or more methods, including, for example, natural convection. Another method for recirculation may be characterized by the use of one or more fluid pumps or micro-pumps, wherein temperature management may be achieved through variations in the flow rates of one or more pumps. In some embodiments, one or more fluid pumps may be positioned outside the reactor vessel and connected to the light source via one or more inlets and/or one or more outlets. In some embodiments, one or more fluid pumps may be incorporated into the core vessel volume. A further method for recirculation may be characterized by the use of one or more gyroscopic fans. In some embodiments, the gyroscopic fan or fans may be incorporated into the core vessel volume.

The photobioreactor described herein may be used to cultivate and/or propagate one or more photosynthetic organisms or microorganisms, or one or more photosensitive organisms or microorganisms, such that one or more photosynthetic or photosensitive organisms comprise a productive culture. In one embodiment, light stimulation is used as a method of control rather than as an energy source or as a driver of reproduction or growth. Organisms that may be used in a productive culture include, but are not limited to, naturally occurring (unmodified) organisms, organisms that are artificially adapted to a suitable environment, organisms that are genetically modified or recombinant, organisms that have been genetically edited using gene editing technologies such as zinc finger nucleases, CRISPR (e.g., CRISPR/Cas9), TALENS, or mega-nucleases, or organisms that may be comprised of synthetic DNA, such that the biological components and systems have been assembled to substantially form an organism that does not exist in any naturally occurring environment. Other organisms that may be cultivated and/or propagated using the disclosed photobioreactor may be capable of producing compounds or biomolecules such as, for example, fatty acids, phycobiliproteins, biofuels and other petrol substitutes, and the like.

The photobioreactor described herein may be manipulated and/or optimized in order to achieve desired organism growth, product expression, and other target outcomes. The manipulations and/or optimizations may comprise the ability to adjust or vary inputs and/or to monitor outputs. In some embodiments, the photobioreactor may be optimized to facilitate high growth and/or density for a particular organism or organisms. In some embodiments, one or more adjustments may comprise the ability to control the rate of expression of biogenic molecules of unique interest or particular value, such as, for example, to alter the final nutritional or product components of the productive culture. In some embodiments, one or more adjustments may comprise the ability to alter organism life cycle. In other embodiments, one or more adjustments may comprise the ability to induce cell destruction or lysis, or to cause the cell to take protective action in order to encourage the production of key molecules.

The photobioreactor described herein may be optimized for one or more specific applications such as, for example, research and development, commercial, and industrial applications. For example, one potential application for the disclosed invention may be cellular agriculture, such as the production of food products, functional ingredients, additives and/or supplements suitable for human consumption and food products, or additives and/or supplements suitable for consumption by pets or livestock. Potential applications for the disclosed photobioreactor may include biomanufacturing. Further potential application for the disclosed photobioreactor may include the storage of energy, photochemistry, photolysis (photo-destruction), the production of biofuels, and the like.

Another potential application for the photobioreactor described herein may comprise the bioremediation of wastewater, excess carbon dioxide, and similar waste products. Such bioremediation may be embodied as a cooperative or symbiotic system between one or more photobioreactors and one or more living animals, such that, for example, waste carbon dioxide and waste nutrients from the animal may be substantially converted in the photobioreactor into oxygen and nutrients for the animal. For example, one or more photobioreactors may provide the bioremediation and conversion of waste products for one or more humans. In some embodiments, one or more photobioreactors may provide the bioremediation and conversion of waste products for one or more humans on a spacecraft or other non-Terran habitat, such as a non-Terran surface habitat.

Figure 23:
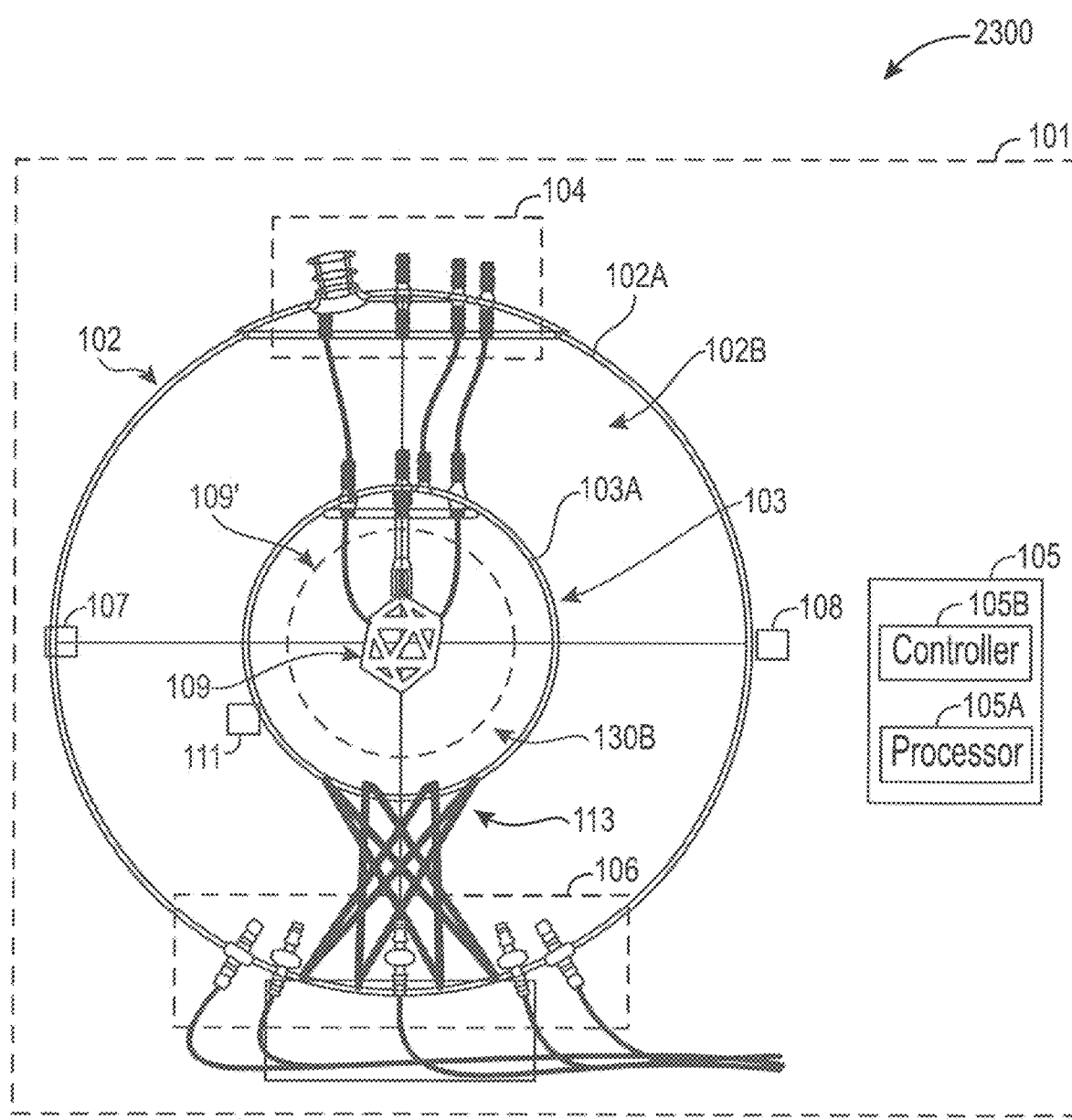
FIG. 23 shows a spherical-shaped photobioreactor in accordance with embodiments of the present disclosure.

FIG. 23 shows a photobioreactor 2300 in accordance with embodiments of the present disclosure. As shown, the photobioreactor 2300 includes a reactor housing or structure 101, a substantially spherical or spherical vessel 102, a water-submersible system 103, a temperature or heat management system 104, a photobioreactor control system 105, a circulation system 106, one or more sensors 107, one or more controlled sources of electromagnetic energy 108, and a cleaning unit 111. The reactor housing 101 is configured to protect or accommodate other components of the photobioreactor 2300. In some embodiments, the reactor housing 101 can have a shape similar to the shape of the spherical vessel 102. In some embodiments, the reactor housing 101 can be shaped or modularized such that the photobioreactor 2300 can be readily coupled to additional or other photobioreactors. In some embodiments, the photobioreactor 2300 can be implemented without the reactor housing 101. The photobioreactor control system 105 includes (1) a processor 105A configured to process instructions regarding other components of the photobioreactor 2300 and (2) a controller 105B configured to communicate with or control other components of the photobioreactor 2300. In some embodiments, the photobioreactor control system 105 can communicate with other components via a wired or wireless connection.

The spherical vessel 102 includes a wall (or an external wall) 102A, defining an interior vessel volume 102B. The water-submersible system 103 includes an inner wall 103A defining an inner space 103B. As shown, a light source 109 is positioned in the inner space 103B. In the illustrated embodiments in FIG. 23, the light source 109 is sized smaller than the inner wall 103A. In other embodiments, however, the light source 109 can be sized/shaped in accordance with the size/shape of the inner wall 103A (e.g., shown as an alternative light source 109' in FIG. 1). The vessel walls (e.g., elements 102A, 103A) may be constructed from a variety of materials that are resistant to leaching, are heat and corrosion resistant, and can withstand moderate pressurization. Appropriate materials include, but are not limited to, plastics (e.g., high-density polyethylene, low-density polyethylene, polypropylene), stainless steel, glass, carbon fiber, silica composites, borosilicate, ceramics and/or bioplastics. In some embodiments, the vessel walls can have a double-layer or dual-layer design. For example, the wall 102A can include (1) an exterior layer facing outwardly toward the housing 101 and (2) an interior layer facing inwardly toward the inner wall 103A. The exterior/interior layer can have different characteristics/coatings/surfaces-treatments suitable for their design purposes. For example, the interior layer can have a water-resistant coating (to prevent the wall 102 from erosion by working fluid positioned in the interior vessel volume 102B), whereas the exterior layer can have a stronger rigidity to prevent damages from accidental, physical impacts from the outside. In some embodiments, the inner wall 103A can also have a double-layer design like the wall 102A.

Figure 32:
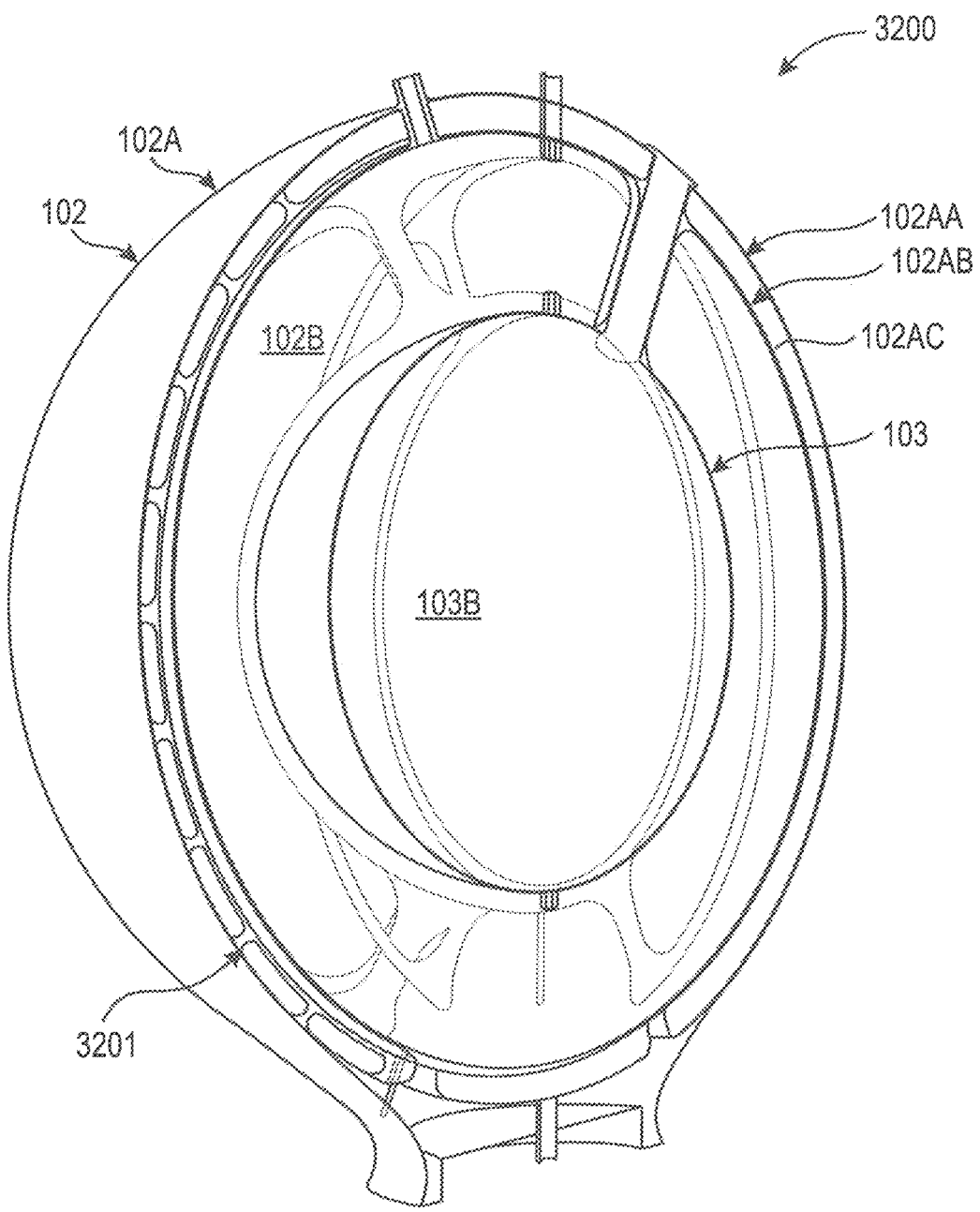
FIG. 32 shows a photobioreactor having a double-wall design in accordance with embodiments of the present disclosure.

FIG. 32 is an isometric, schematic view of a photobioreactor 3200 having a double-wall design in accordance with embodiments of the present disclosure. The photobioreactor 3200 includes an outer vessel 102 having an external wall 102A defining an interior vessel space 102B. The photobioreactor 3200 includes an inner vessel or a water-submersible system 103 inside the outer vessel 102. The inner vessel 103 includes an inner wall 103A defining an inner space 103B. The inner space 103B is configured to accommodate a light source configured to emit light into the working fluid positioned in the interior vessel space 102B. As shown in FIG. 32, the external wall 102A includes an exterior layer 102AA and an interior layer 120AB. The exterior layer 102AA and the interior layer 120AB can be made of different materials. As shown in FIG. 32, the exterior layer 102AA and the interior layer 120AB can together define a space 102AC therebetween. In some embodiments, one or more spacers 3201 can be positioned in the space 102AC to enhance the structural rigidity of the outer vessel 102.

The sensors 107 (one shown in FIG. 23) are configured to measure the status of the working fluid positioned in the interior vessel volume 102B. In the illustrated embodiments shown in FIG. 23, the sensor 107 is positioned on an inner surface of the wall 102A. In other embodiments, the sensor 107 can be positioned in other locations or floats in the interior vessel volume 102B. The controlled source of electromagnetic energy 108 is configured to provide electromagnetic energy (e.g., light, illumination, etc.) to the working fluid (and the organisms or biomass therein). In some embodiments, the controlled sources of electromagnetic energy 108 can be paired with one or more corresponding sensors 107 and are positioned opposite to the corresponding sensors 107 (e.g., one is positioned at one side of the vessel 102, whereas the other is positioned at the opposite side of the vessel 102). By this arrangement, the sensor 107 can sense the status of the biomass therebetween based on how much light/energy is absorbed from the controlled source 108 to the sensor 107. In the illustrated embodiments in FIG. 23, the controlled source 108 is positioned on an outer surface of the vessel 102. In other embodiments, however, the controlled source 108 can be positioned at various locations.

As shown in FIG. 23, the water-submersible system 103 is supported by multiple support structures or struts 113. The support structures 113 couple the water-submersible system 103 to the vessel 102. In some embodiments, the water-submersible system 103 and the vessel 102 can be coupled by other suitable means. In some embodiments, the water-submersible system 103 can float in the interior vessel volume 102B. In some embodiments, the water-submersible system 103 for converting electrical energy into electromagnetic radiation can be surrounded by a substantially spherical barrier, such as a spheroid or toroid barrier, such that the barrier separates the interior water-submersible system 103 from the working fluid (e.g., culture) positioned in the interior vessel volume 102B. The barrier may be constructed from a variety of inert transparent or semi-transparent materials, and/or materials that are tolerant to extreme temperatures. Appropriate materials include, but are not limited to, plastic and glass. The barrier may also be comprised of materials or meta-materials that allow for the manipulation of photons (e.g., photon-sensitive or photon-responsive materials). For example, photons may be manipulated using lensing, variations in attenuation, shifts in wavelength, and the like.

The temperature management system 104 is configured to circulate heat dispersal fluid or coolant/refrigerant into and out of the water-submersible system 103. By this arrangement, the temperature management system 104 can adjust or manage the temperature of the light source 109 as well as the temperature of the working fluid in the interior vessel volume 102B. In some embodiments, the temperature management system 104 is controlled by the photobioreactor control system 105. In some embodiments, the temperature management system 104 can adjust the temperature in the water-submersible system 103 based on environmental conditions such as an environmental temperature, a wind speed, humidity, sun angle, etc. The temperature management system 104 can include one or more inlets and one or more outlets configured to deliver and receive heat dispersal fluid. In some embodiments, the temperature management system 104 includes one or more motors, pumps, valves, propellers, and/or fans. These components can be electronically-controlled or thermodynamic (heat/temperature-controlled). In some embodiments, these motors, pumps, valves, propellers, and/or fans can be integrated into the reactor housing or structure 101 of the photobioreactor 2300. In some embodiments, these motors, pumps, valves, propellers, and/or fans can be integrated into the inner wall 103A or the wall 102A.

The circulation system 106 is configured to manipulate, extract, or circulate fluid, waste or nutrients into and out of the spherical vessel 102. The circulation system 106 is in operable communication with the photobioreactor control system 105. In some embodiments, the circulation system 106 includes one or more motors, pumps, valves, propellers, and/or fans. These components can be electronically-controlled or thermodynamic (heat/temperature-controlled). In some embodiments, these motors, pumps, valves, propellers, and/or fans can be integrated into the reactor housing or structure 101 of the photobioreactor 2300. In some embodiments, these motors, pumps, valves, propellers, and/or fans can be integrated into the wall 102 or the water-submersible system 103. In some embodiments, the circulation system 106 can include a spigot configured to control a flow in the circulation system. The circulation system 106 can include one or more inlets and one or more outlets configured to deliver and receive working fluid in the interior vessel volume 102B.

The cleaning unit 111 can be positioned in the interior vessel volume 102B and is configured to adjust the condition of the working fluid therein. For example, the cleaning unit 111 can be configured to filter or remove undesirable particles from the working fluid. In some embodiments, the cleaning unit 111 can be positioned on an outer surface of the water-submersible system 103. In some embodiments, the cleaning unit 111 can be positioned on an inner surface of the wall 102A. In some embodiments, the cleaning unit 111 can float in the interior vessel volume 102B.

Figure 24:
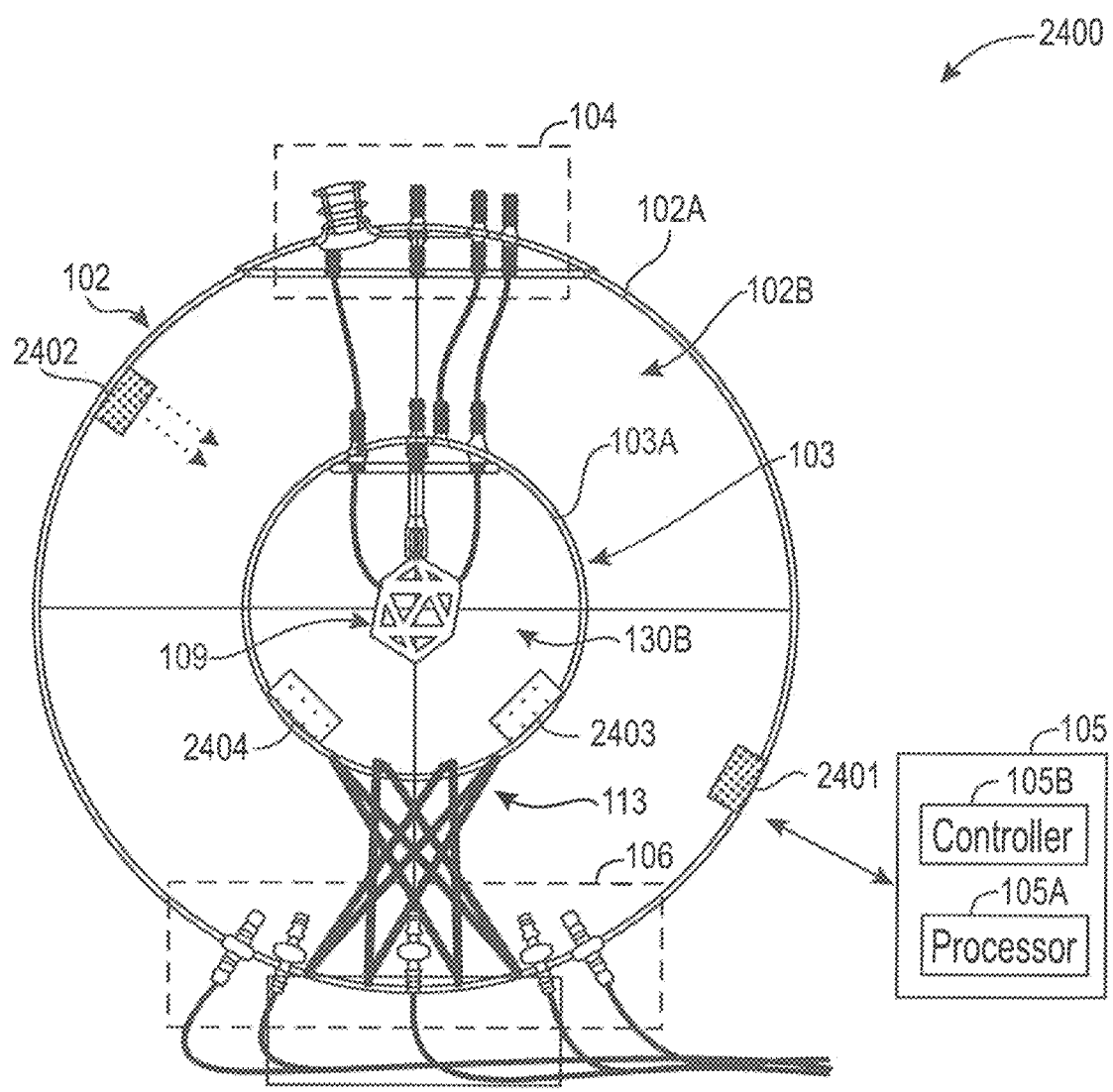
FIG. 24 shows a spherical-shaped photobioreactor in accordance with embodiments of the present disclosure.

FIG. 24 shows another photobioreactor 2400 in accordance with embodiments of the present disclosure. The photobioreactor 2400 has a structure similar to the photobioreactor 2300 (e.g., components with the same reference numbers have the same or similar structural feature and functions). The photobioreactor 2400 includes (1) a working-fluid sensor 2401 positioned on the inner surface of the wall 102A and (2) a source of illumination 2402 positioned on (or embedded in) the inner surface of the wall 102A opposite the working-fluid sensor 2401. The source of illumination 2402 provides light to the working fluid in the interior vessel volume 102B. The working-fluid sensor 2401 receives the light from the source of illumination 2402 passing through the working fluid and accordingly determines a status of the biomass in the working fluid (e.g., whether it is growing as planned). The working-fluid sensor 2401 can communicate with the control system 105 via a wired connection regarding the status. The control system 105 can then send instructions to other systems (e.g., systems 103, 104 and/or 105) based on the status. For example, the status can be indicative that the biomass is not growing due to a low temperature. Then the control system 105 can instruct the light source 109 to increase its light level so as to increase the temperature in the interior vessel volume 102B. In some embodiments, the inner surface of the wall 102A can be hydrophobic so as to prevent or at least mitigate the accumulation of biomass on that surface.

As shown in FIG. 24, the photobioreactor 2400 includes a first sensor 2403 and a second sensor 2404 positioned on the inner surface of the inner wall 103A. The first and second sensors 2403, 2404 are configured to provide two points of detection such that the control system 105 can have a better understanding regarding the distribution of heat-dispersal fluid in the inner space 103B. In some embodiments, the photobioreactor 2400 can include more than two sensors.

Figure 25:
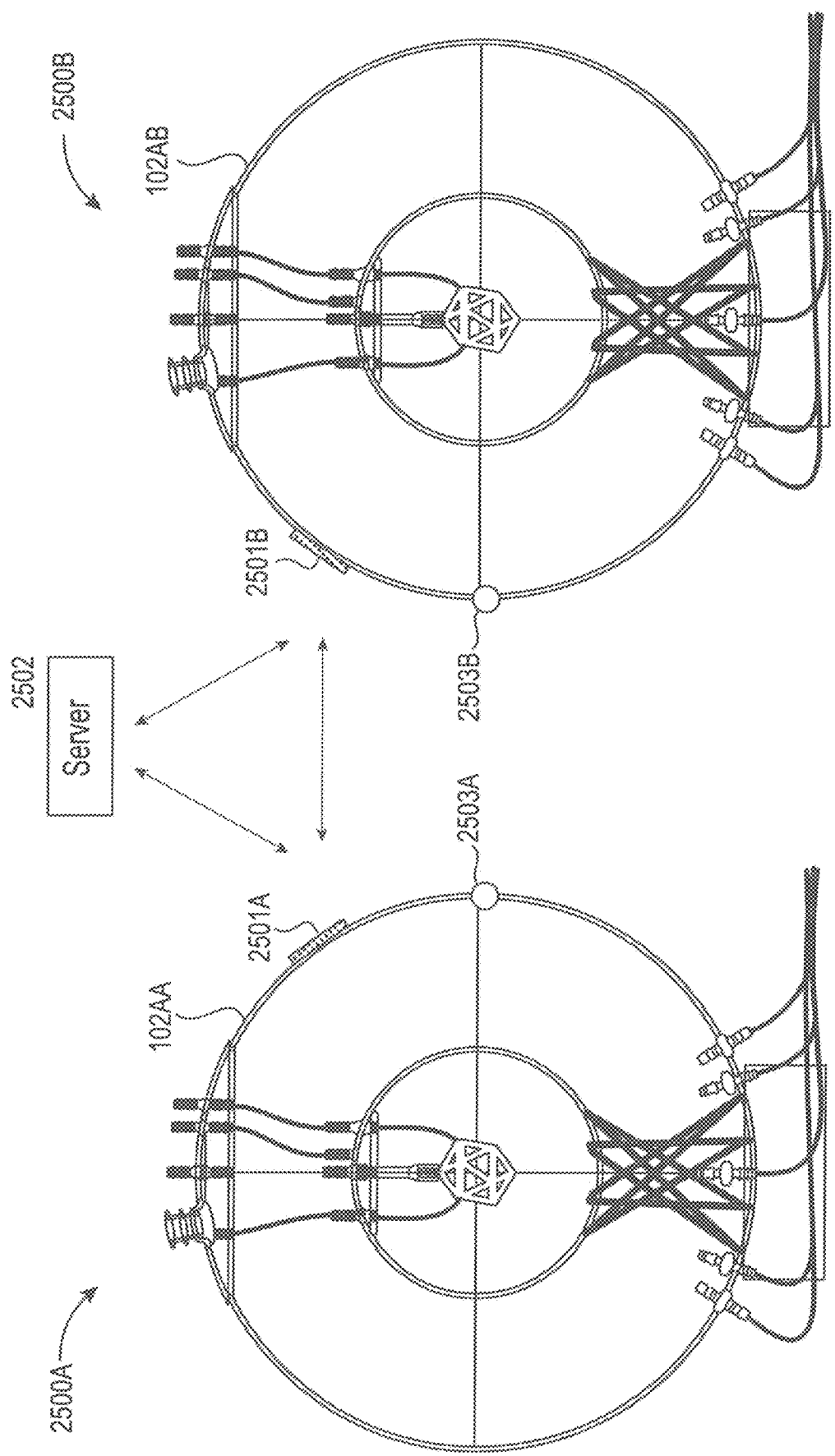
FIG. 25 shows two modular photobioreactors in accordance with embodiments of the present disclosure.

FIG. 25 shows two modular photobioreactors 2500A, 2500B in accordance with embodiments of the present disclosure. The photobioreactors 2500A, 2500B have a structure similar to the photobioreactor described above (e.g., photobioreactor 2300 or 2400). The photobioreactor 2500A includes an antenna 2501A positioned on or embedded in a wall 102AA of the photobioreactor 2500A. Similarly, the photobioreactor 2500B includes an antenna 2501B positioned on or embedded in a wall 102AB of the photobioreactor 2500B. The antennae 2501A and 2501B are configured to communicate with each other and a server 2502. By this configuration, the server 2502 can control or coordinate the biomass production in the photobioreactors 2500A, 2500B. In some embodiments, the antenna 2501A or 2501B can be positioned on or embedded in a housing of the photobioreactor 2500A or 2500B. In some embodiments, there can be more than two modular photobioreactors stacked/positioned in a rigid rack or by scaffolding. In some embodiments, the more than two modular photobioreactors can be positioned as an array. In some embodiments, there can be conduits/pipes or other suitable connectors configured to couple two or more modular photobioreactors. These conduits can be used to convey fluid (e.g., heat dispersal fluid, working fluid, etc.) between/among modular photobioreactors. In some embodiments, the server 2502 can be configured to control the fluid conveyance (e.g., flow direction, rate, etc.) between/among modular photobioreactors.

As shown in FIG. 25, the photobioreactor 2500A includes an acoustic/ultrasound sensor 2503A positioned on or embedded in the wall 102AA, whereas the photobioreactor 2500A includes an acoustic/ultrasound sensor 2500B positioned on or embedded in the wall 102AB. The acoustic sensors 2503A, 2503B can be configured to determine a status of working fluid in the photobioreactor 2500A or 2500B.

Figure 26:
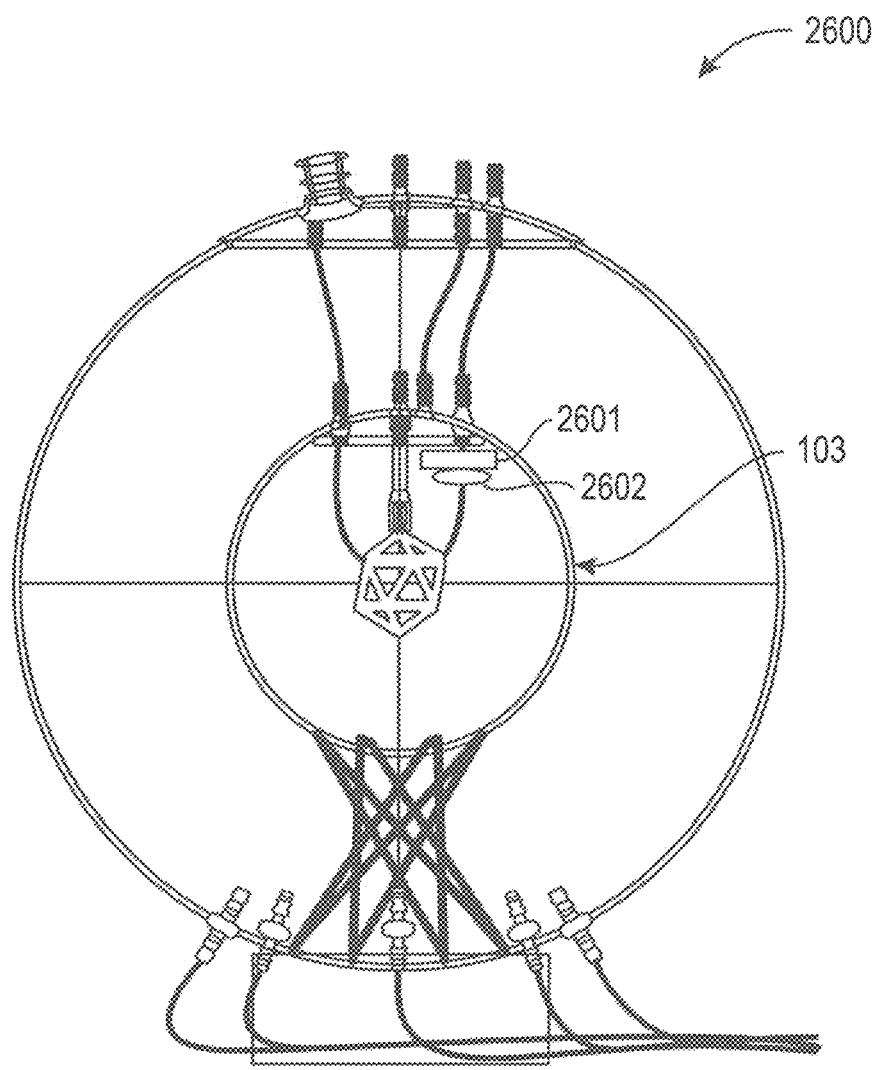
FIG. 26 shows a modular photobioreactor in accordance with embodiments of the present disclosure.

FIG. 26 shows another modular photobioreactor 2600 in accordance with embodiments of the present disclosure. The modular photobioreactor 2600 includes a microprocessor 2601 and a microcontroller 2602 positioned in its water-submersible system 103. The microprocessor 2601 has functions similar to those of the processor 105A, and the microcontroller 2602 has functions similar to those of the controller 105B. By this arrangement, the modular photobioreactor 2600 does not need an external control system and therefore is suitable for modular configurations/arrangements.

Figure 27:
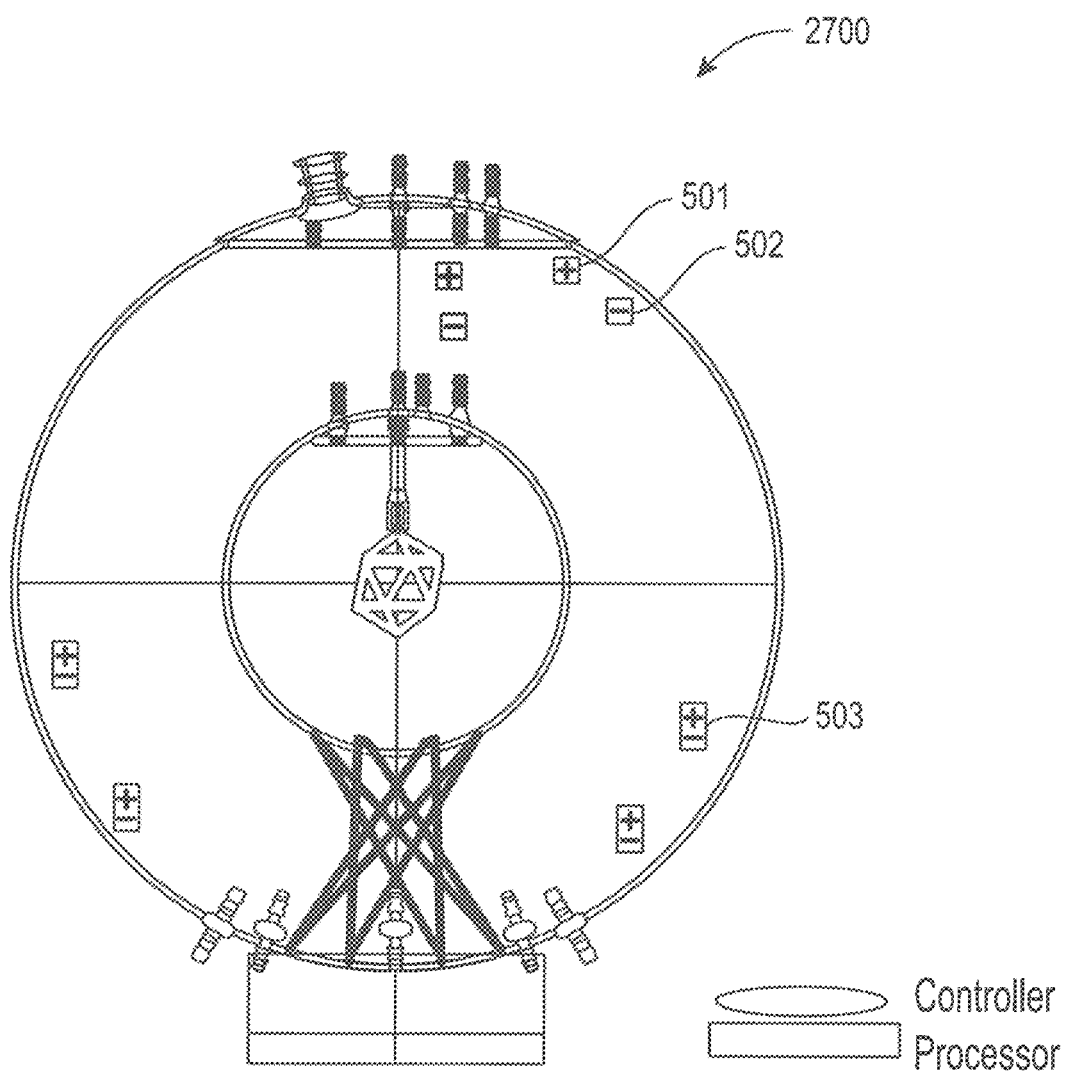
FIG. 27 shows a modular photobioreactor in accordance with embodiments of the present disclosure.

FIG. 27 shows a modular photobioreactor 2700 in accordance with embodiments of the present disclosure. The modular photobioreactor 2700 includes positive conductors 501, negative conductors 502, and a set of distributed electromagnets 503 configured to provide electricity to the photobioreactor 500 from a power supply. For example, the locations of the positive conductors 501, the negative conductors 502, and the distributed electromagnets 503 can vary to accommodate the needs for different types of power supplies. For example, when multiple modular photobioreactors are stacked and positioned, the modular photobioreactor at the bottom can receive power via a conductor located on its lower surface. As another example, the modular photobioreactor at the top can receive power via a conductor located on its upper surface. This arrangement provides flexibility for the modular designs/configurations.

Figure 28:
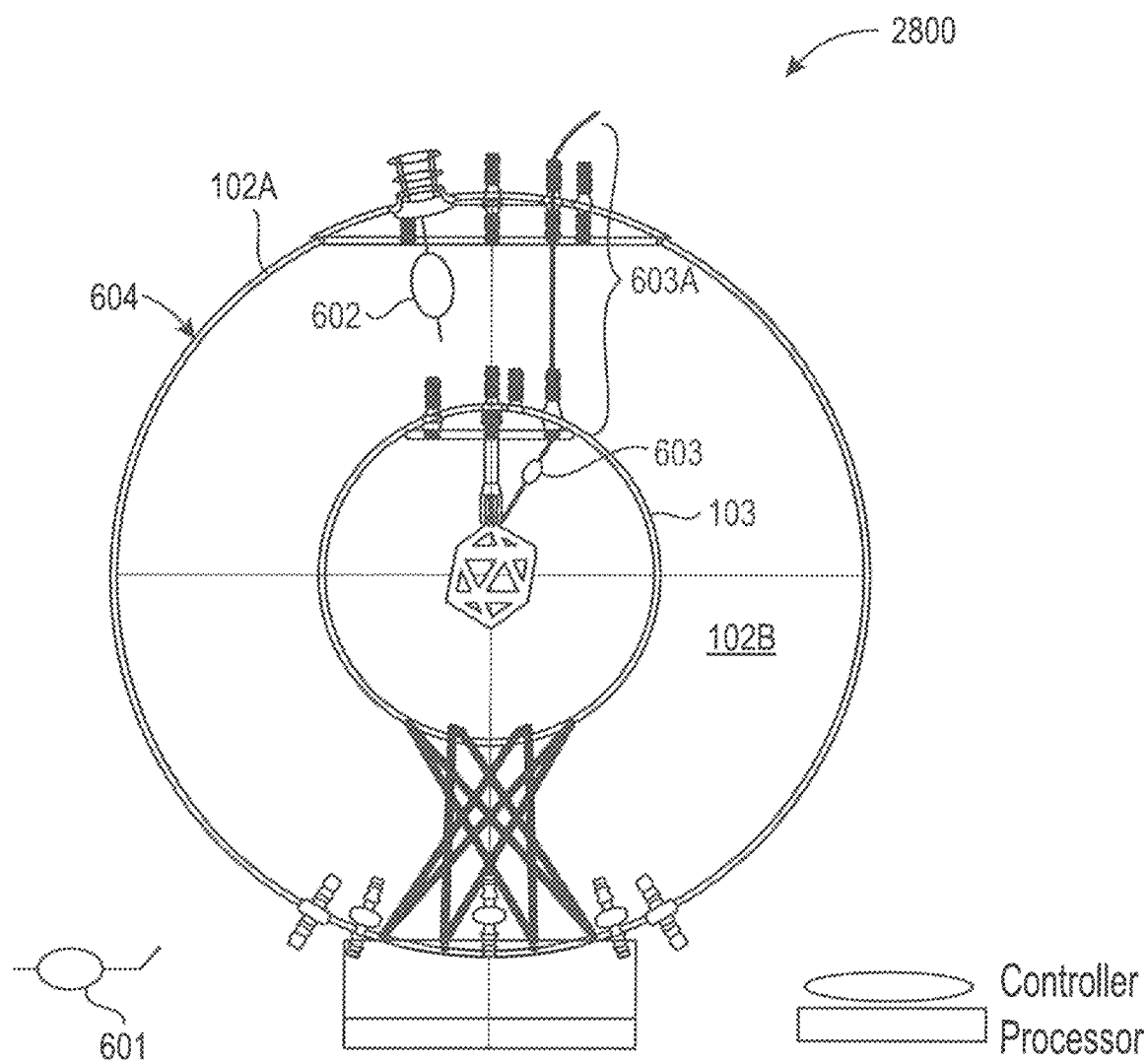
FIG. 28 shows a power supply associated with a photobioreactor in accordance with embodiments of the present disclosure.

FIG. 28 shows a power supply associated with a photobioreactor 2800 in accordance with embodiments of the present disclosure. In some embodiments, a power supply 601 can be located outside the photobioreactor 2800. In some embodiments, a power supply 602 can be positioned within the internal vessel volume 102B (see e.g., FIG. 1). In some embodiments, a power supply 603 can be positioned in the water-submersible system 103 (see e.g., FIG. 1) and coupled to an external power supply via a hard-wired connection 603A. In some embodiments, electricity can be supplied to the photobioreactor 600 via conductive materials 604 embedded/coated/positioned on the wall 102A (see e.g., FIG. 1). In some embodiments, the power supply 603 and the conductive materials 604 can be used together to provide power to the photobioreactor 2800.

Figure 29A:
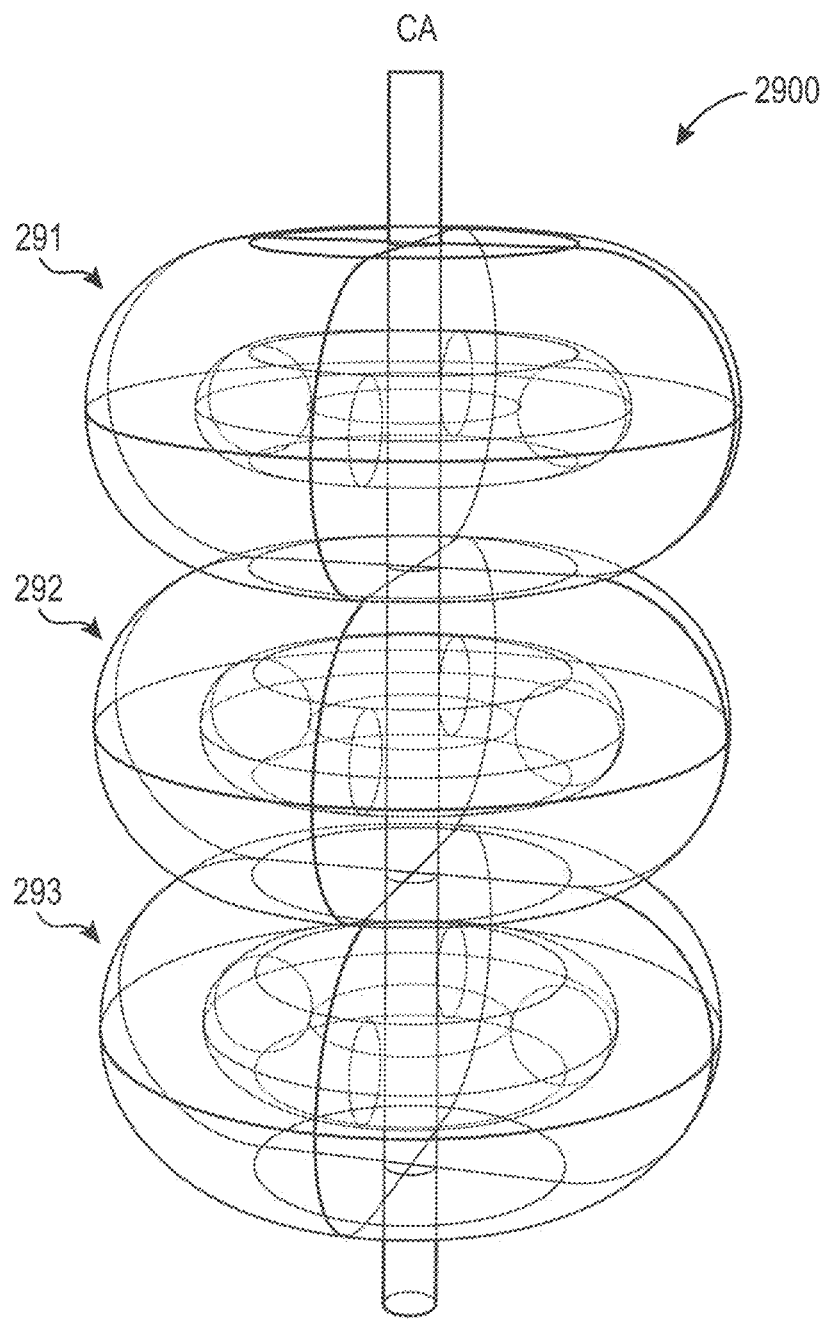
FIG. 29A shows a schematic representation of an exemplary high-density configuration of multiple toroid modular photobioreactors in accordance with embodiments of the present disclosure.

FIG. 29A shows a high-density photobioreactor system 2900. The photobioreactor system includes three ring-shaped photobioreactors, 291, 292, and 293 stacked and positioned about central axis CA. In some embodiments, the high-density photobioreactor system 290 can have a different number of modular photobioreactors and can have different configurations.

Figure 29B:
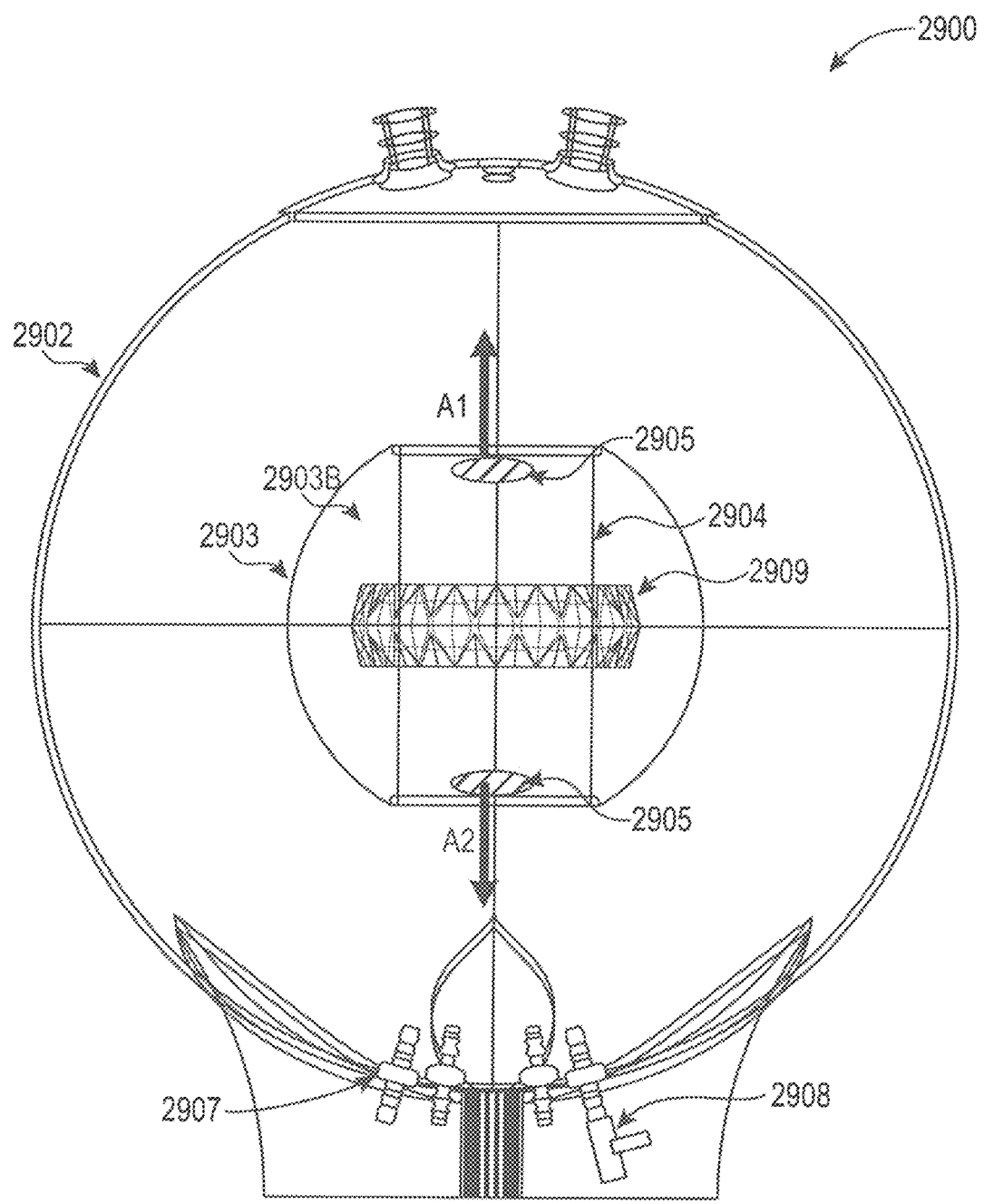
FIG. 29B is a top view of a ring-shaped photobioreactor in accordance with embodiments of the present disclosure.

FIG. 29B is a top view of a ring-shaped photobioreactor 2900 discussed above with reference to FIG. 29A. As shown, the ring-shaped photobioreactor 2900 includes a toroid vessel 2902 and a water-submersible system 2903 defining an inner space 2903B. A toroid light source 2909 is positioned in the inner space 2903B. The water-submersible system 2903 defines a central passage 2904. Working fluid positioned in the toroid vessel 2902 can flow through the central passage 2904 in direction A1 or A2. The water-submersible system 2903 includes pumps 2905A, 2905B integrated therein and configured to facilitate the flow of the working fluid in the toroid vessel 2902. The photobioreactor 2900 also includes a pump 2907 positioned on or embedded in the toroid vessel 2902, so as to facilitate flow-in or flow-out of the working fluid. As shown, the photobioreactor 2900 can include a spigot, tap, or faucet 2908 configured to control the flow of the working fluid.

Figure 30:
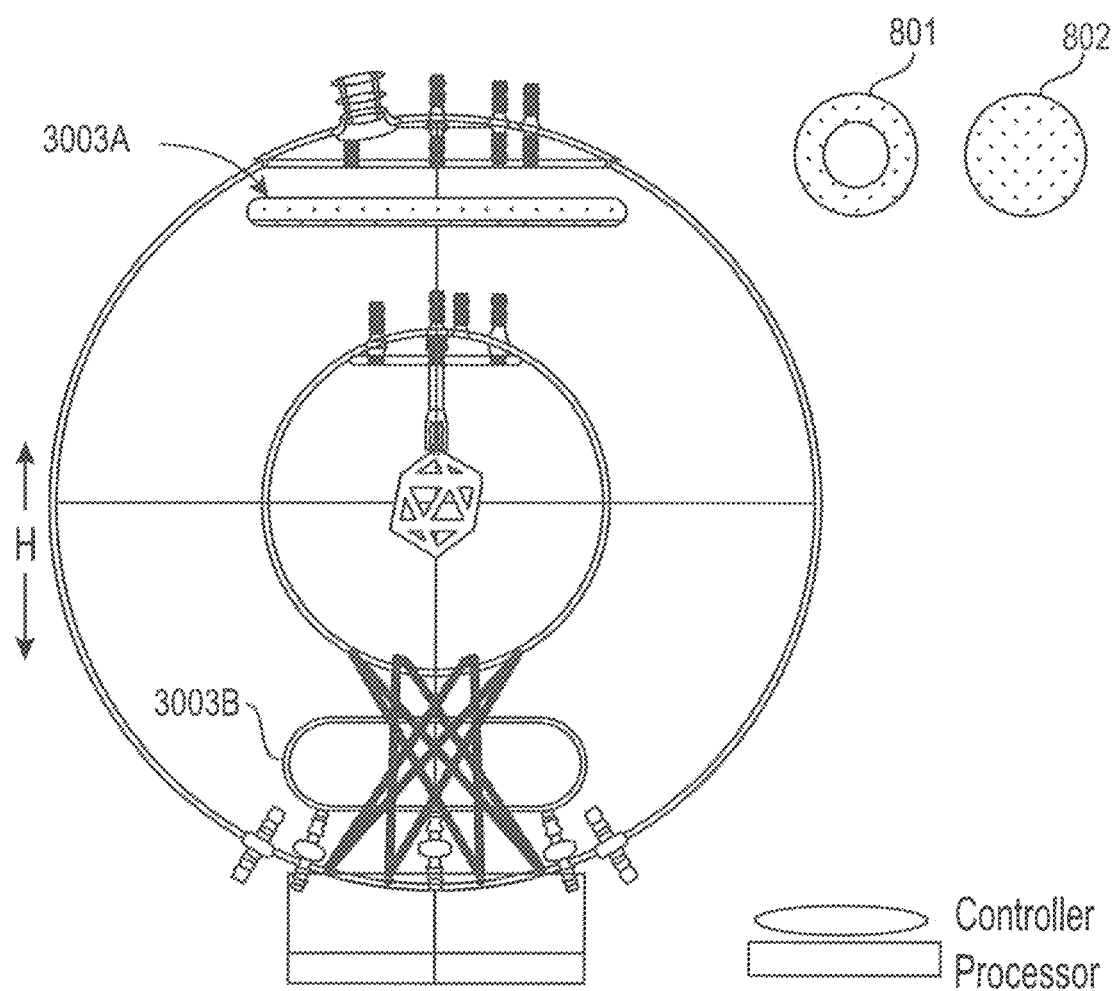
FIGS. 30 and 31 show gas diffusion devices positioned in a photobioreactor in accordance with embodiments of the present disclosure.
Figure 31:
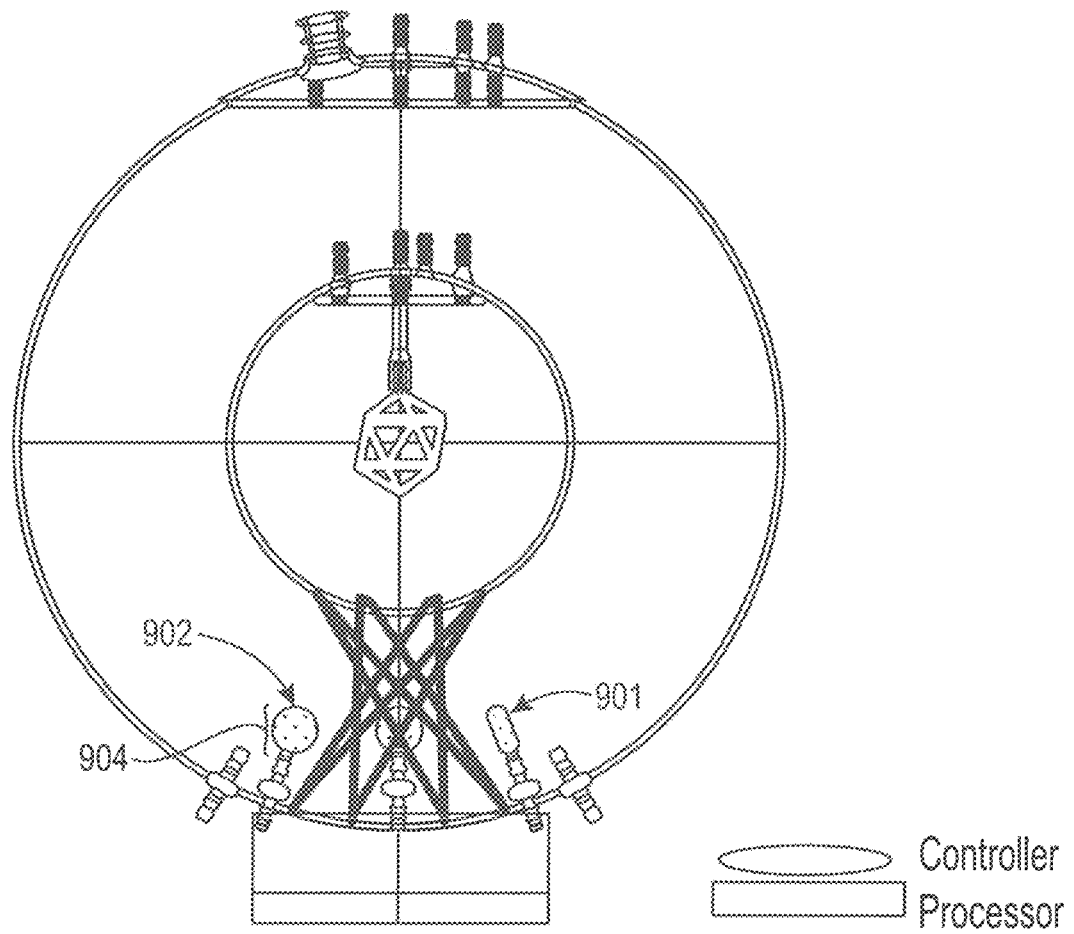

FIGS. 30 and 31 show gas diffusion devices positioned in a photobioreactor in accordance with embodiments of the present disclosure. The gas diffusion device can be included in a ventilation system configured to add or disperse gases into the photobioreactor. The ventilation system can include multiple gas diffusion devices. As shown in FIG. 30, the gas diffusion device can be a ring-shaped gas diffusion device 801. As also shown in FIG. 30, the gas diffusion device can be a disc-shaped gas diffusion device 802. As shown in FIG. 30, two gas diffusion devices 3003A, 3003B can be positioned at different "heights" or locations of the photobioreactor. As shown in FIG. 31, a cylindrical gas diffusion device 901 can be positioned or coupled to a gas inlet of the photobioreactor. As also shown in FIG. 31, a spherical gas diffusion device 902 can be positioned or coupled to another gas inlet of the photobioreactor. As shown in FIG. 31, a plurality of gas diffusion devices can be arranged as a ring or a disc. In some embodiments, the gas diffusion can be porous or include semi-permeable material.

Control Systems

In some embodiments, wherein the control system or systems of the photobioreactor is optimized for one or more parameters, including, for example, optimal environment, target end product or products, production efficiency, bioremediation (uptake of, for example, carbon dioxide), system integrity, and/or system longevity. In some embodiments, one or more of the control systems is interconnected to form a substantially distributed network of photobioreactors, such that the network is monitored and/or controlled, for example, individually or in various combinations. In some embodiments, one or more of the control systems is designed as a top-down artificial intelligence substantially characterized by the use of a machine learning approach including, for example, the use of the photobioreactors as a system for which multiple optimization scenarios are run.

In some embodiments, the photobioreactors are characterized by the capability of the control system or systems to identify a solution, process or path that optimizes for the desired parameter (e.g., growth rate, product expression, overall reactor performance). In some embodiments, one or more of the control systems utilize information obtained through the optimization scenarios to control a massively distributed network of interconnected reactors. In some embodiments, one or more of the control systems comprises the ability to make queries of third-party systems that are suited to the problem at hand, including, for example, quantum computers. In some embodiments, one or more of the control systems of the photobioreactors substantially function using an aggregate swarm control method characterized by, for example, the use of small low-power computers that aggregate sensor input for individual photobioreactors. In some embodiments, the control system or systems are further characterized by the capability to make immediate decisions about how to respond to a given scenario through a fixed number of possible reactions to sensor stimuli or data. In some embodiments, the control system or systems feed the information obtained through the sensors back to one or more central control systems.

In some embodiments, the control system or systems of the photobioreactor permit for the low-power computers to make decisions based on what adjacent photobioreactor control systems are doing and the outcomes of those behaviors, utilizing, for example, a swarm methodology driven by and optimized off of a flocking algorithm in which each system makes decisions solely based on data from its adjacent neighbors and itself. In some embodiments, one or more of the control systems of the photobioreactor comprise top-down artificial intelligence and aggregate swarm control, such that the low-power swarm control make decisions about individual photobioreactor behaviors to maintain normal operation while the top-down artificial intelligence make larger decisions to optimize for particular circumstances or goals, or to react to larger stimuli.

In some embodiments, one or more control systems of the photobioreactor is substantially used for data processing and management. In some embodiments, the system or systems for data processing and management is optimized to control for one or more parameters, including, for example, optimal environment, target end product or products, production efficiency, bioremediation (uptake of, for example, carbon dioxide), system integrity, and/or system longevity. In some embodiments, two or more systems for data processing and management are interconnected to form a substantially distributed network of photobioreactors, such that, for example, data is aggregated from two or more photobioreactors. In some embodiments, the data transfer occurs between one or more photobioreactors or photobioreactor modules, between one or more downstream control systems, between photobioreactors and control systems, or between any combination of the components. In some embodiments, the data is received and/or transferred using substantially hard-wired connections, substantially wireless connections, or a combination of hard-wired and wireless connections. In some embodiments, the system or systems comprise one or more sensor connections. In some embodiments, one or more of the sensor connections is integrated into the reactor housing or structure. In some embodiments, the method of integrating the sensor connection or connections into the reactor structure is characterized by the use of additive manufacturing. In some embodiments, the method of integrating the sensor connection or connections into the reactor structure is further characterized by the use of conductive printing feedstock such as, for example, using selective deposition. In some embodiments, one or more systems for data processing and/or management comprises one or more processing units characterized by the ability to combine incoming data, manage outgoing data, and/or transmit data to later-stage control systems. In some embodiments, one or more of the processing units receive data from one or more sensing or monitoring systems. In some embodiments, one or more of the processing units are further characterized by the capability for autonomous analysis of photobioreactor performance and/or autonomous decision-making regarding photobioreactor performance. In some embodiments, one or more of the processing units is incorporated into the structure of the lighting system, such that, for example, the lighting system is configured to provide additional temperature mediation capability.

Culture and Media

In some embodiments, the photobioreactors comprise one or more systems for extraction and/or manipulation of working fluid such as, for example, culture or media. Non-limiting examples of culture and media include liquids, nutrients, and biological organisms. In some embodiments, one or more of the systems allow for concentration and initial de-watering of culture prior to harvest. In some embodiments, the system or systems comprises one or more electronic motors. In some embodiments, the system or systems allows for the removal and/or addition of liquid or working fluid (e.g., algal culture and suspended nutrients) from the void between the interior vessel and the exterior vessel wall, such that, for example, waste media is removed and/or fresh media is added without impacting culture density. In some embodiments, the system or systems allows for steady-state, continuous or near continuous production.

In some embodiments, the method of working fluid manipulation is characterized by the use of electronically controlled valves. In some embodiments, one or more of the electronically controlled valves is connected to a spigot which comprises an inlet, an outlet, or both. In some embodiments, one or more of the electronically controlled valves is configured to facilitate the removal of liquid and other materials from the vessel, such as, for example, mature culture and/or nutrient-depleted media.

In some embodiments, the method of working fluid manipulation is characterized by the use of a dual-walled outer housing, such that the outer barrier of the photobioreactor comprises a watertight exterior wall, an interior wall, and a void between the exterior and interior walls. In some embodiments, the photobioreactor is comprises porous or semi-permeable materials to construct the interior wall, such that the porous material allows for the extraction and/or manipulation of liquids and other materials, such as, for example, culture or media.

In some embodiments, the system or systems facilitates the mixing or agitation of the working fluid. In some embodiments, the method of working fluid is characterized by the ability to mix independently of gas introduction. In some embodiments, the mixing system or systems comprises one or more inlets and one or more outlets. In some embodiments, the mixing system or systems comprises one or more pumps. In some embodiments, the one or more pumps is embedded into the vessel housing. In some embodiments, the one or more pumps is characterized by the use of light integration. In some embodiments, the one or more pumps is thermodynamic.

In some embodiments, electricity is introduced into the working fluid. In some embodiments, the introduction of electricity is substantially achieved using a system of distributed positive and negative conductors (anode/cathode). In some embodiments, the introduction of electricity is substantially achieved using a system of distributed electro-magnets.

In some embodiments, one or more systems provide for the addition and/or distribution of media and chemicals to the working fluid. In some embodiments, the media is pre-mixed. In some embodiments, the media is added as individual components. In some embodiments, the system or systems use data provided by one or more sensing or monitoring systems to infer the quality and/or nutrient value of incoming media. In some embodiments, the media and/or chemical additions occurs at a single point of introduction, at two points of introduction, or at three or more points of introduction. In some embodiments, two or more points of introduction substantially form a network of micro-channels. In some embodiments, the network of micro-channels are embedded into the reactor housing and/or into internal support structures within the vessel interior. In some embodiments, the method of media addition or distribution is substantially characterized by the use of electronically controlled valves.

In some embodiments, the photobioreactor further comprises one or more systems to facilitate media sterilization. In some embodiments, the method of media sterilization utilizes in-line irradiation, ultraviolet or near-ultraviolet radiation, microwave radiation, thermal sterilization, membrane or porous filtration methods, diatomic (diatomaceous) earth, or any combination thereof.

In some embodiments, the photobioreactor further comprises one or more systems for the purpose of removing or cleaning the outer surface of the lamp assembly. In some embodiments, the system or systems comprise one or more cleaning units. In some embodiments, the one or more cleaning units are mounted within the interior vessel volume. In some embodiments, one or more cleaning units is mounted on the outside surface of the lamp assembly. In some embodiments, the cleaning unit or units comprise one or more robotic devices such that, for example, one or more cleaning units is controlled using radio, electronic or other methods of communication. In some embodiments, the cleaning units provide for suction, expulsion, or both suction and expulsion, such as, for example, to recirculate culture through the robotic device. In some embodiments, one or more robotic cleaning units comprise a substantially flexible or pliable body. In some embodiments, the robotic cleaning units comprise one or more movable connections, such as hinges or sockets. In some embodiments, the robotic cleaning units comprise soft or flexible materials. In some embodiments, the one or more robotic cleaning units operate with gas. In some embodiments, the system or systems comprise one or more cleaning unit actuators.

Gas

In some embodiments, the photobioreactor comprise one or more gas addition and/or dispersion systems. In some embodiments, the gas or gases comprise one or more of oxygen, carbon dioxide, methane, biogas, syngas, human or animal exhalant, and the like. In some embodiments, the gas or gases are sourced or substantially sourced from ambient atmosphere. In some embodiments, the gas or gases comprise ratio-adjusted gases, such as, for example, a mix of oxygen and carbon dioxide with a smaller proportion of oxygen relative to the proportion of carbon dioxide. In some embodiments, one or more systems for gas addition and/or dispersion comprise one or more air manifolds. In some embodiments, one or more of the manifolds is located outside of the reactor vessel. In some embodiments, one or more of the manifolds is integrated into the reactor housing, such as, for example, through a manufacturing process, for example, an additive manufacturing processes. In some embodiments, the manifolds provide a method for gas exchange, such as, for example, allowing oxygen to exit the working fluid and allowing carbon dioxide to enter the working fluid. In some embodiments, one or more gases is exchanged simultaneously.

In some embodiments, the one or more systems for gas addition and/or dispersion comprise one or more gas diffusion systems. A non-limiting example of a gas diffusion system is an air stone. In some embodiments, the one or more gas diffusion systems (e.g., air stones) is cylindrical, substantially cylindrical, disc-shaped, substantially disc-shaped, ring-shaped, substantially ring-shaped, or any combination thereof. In some embodiments, the gas diffusion systems (e.g., air stones) are constructed and/or coated with a porous, substantially porous or semi-permeable material. In some embodiments, the gas diffusion systems (e.g., air stones) are integrated into the reactor housing, for example, through a manufacturing or assembly process. In some embodiments, the manufacturing process is an additive manufacturing processes. In some embodiments, the gas diffusion systems (e.g., air stones) is controlled through the use of one or more valves, such as, for example, electronic valves. In some embodiments, the one or more valves is controlled independently. In some embodiments, the one or more values valves are controlled in groups of two or more.

In some embodiments, a plurality of gas diffusion systems (e.g., air stones) are arranged in a circular or substantially circular shape to form one or more rings or discs of varying diameter. In some embodiments, two or more rings, discs and/or circular gas diffusion systems (e.g., air stones) are arranged at varying heights relative to the bioreactor vessel. In some embodiments wherein one or more rings, discs and/or circular gas diffusion systems (e.g., air stones) are connected to one or more air chambers. In some embodiments, pressure between two or more chambers is controlled, such that, for example, redirecting pressure between chambers provides for moving or pulsed gas addition and/or dispersion.

In some embodiments, one or more systems for gas addition and/or dispersion is characterized substantially by the direct introduction of gases into the working fluid. In some embodiments, the method of direct gas introduction comprises one or more bioreactor support structures, whose additional purpose includes providing support to the water-submersible core within the vessel volume. In some embodiments, the support structures comprise a void that provides for the ability to store gases. In some embodiments, the support structures comprise one or more air manifolds that, for example, facilitate the addition and/or diffusion of gas into the working fluid. In some embodiments, the support structures comprise one or more gas diffusion systems (e.g., air stones) that, for example, facilitate the addition and/or diffusion of gas into the working fluid. In some embodiments, the one or more systems for gas addition and/or dispersion comprise a dual-walled outer housing, such that, for example, the outer barrier of the photobioreactor comprises a watertight exterior wall, an interior wall, and a void between the exterior and interior walls. In some embodiments, the void between the exterior and interior vessel walls provides for the introduction of gas to the working fluid. In some embodiments, the interior wall comprises a porous and/or semi-permeable material. In some embodiments, the porous and/or semi-permeable material has a pore diameter small enough to prevent individual cells on the inside of the reactor from passing through the interior wall to the void, while allowing media and other working fluid to pass between the void and the vessel interior. In some embodiments, the porous and/or semi-permeable material allows for the extraction and/or manipulation of working fluid, including, for example, concentration and/or filtration of organisms. In some embodiments, the permeability of the inner wall is controlled or substantially controlled, such as, for example, using air pressure.

Materials and Manufacturing

In some embodiments, the photobioreactor is constructed from one or more of a variety of food grade or highly inert materials that do not leach, are corrosion resistant, are heat resistant, and/or can withstand light pressurization, including, for example, plastics such as high-density polyethylene, low-density polyethylene, and polypropylene, stainless steel, glass, carbon fiber, silica composites, borosilicate, ceramics, bioplastics and the like. In some embodiments, the water-submersible light source is surrounded by a spherical or substantially spherical barrier. In some embodiments, the spherical or substantially spherical barrier is a toroid barrier. In some embodiments, the spherical or substantially spherical barrier surrounds the light source and comprises a variety of inert materials, such as transparent materials and materials that are tolerant to extreme temperatures, including, for example, plastic and glass; or materials or meta-materials that allow for the manipulation of photons. In some embodiments, the one or more surfaces comprise hydrophobic, superhydrophobic, hydrophilic and/or oleophobic properties. In some embodiments, the hydrophobic, superhydrophobic, hydrophilic and/or oleophobic properties is achieved or substantially achieved through one or more methods achievable to one of skill in the art, including, for example, the addition of surface coatings, mechanical or thermal etching, the use of inherently hydrophobic materials, high-resolution additive manufacturing, and the like. In some embodiments, the photobioreactor comprises multiple separate and interconnected components including, for example, a water-submersible substantially spherical method of converting electrical energy into electromagnetic radiation (light source), a system for circulating heat dispersal fluid into and out of the light source, pumps, air addition and dispersion components, and the like. In some embodiments, the one or more components functions as stand-alone components in relation to the photobioreactor. In some embodiments, the one or more components is integrated into the water-submersible interior vessel, positioned in the void between the interior vessel and the exterior wall, or positioned outside to the exterior vessel of the photobioreactor. In some embodiments, the two or more components are positioned in two or more of these locations relative to the photobioreactor.

In some embodiments, one or more components of the photobioreactor are produced using additive manufacturing processes including, for example, binder jetting, directed energy deposition, material extrusion, material jetting, powder bed fusion, sheet lamination, vat photopolymerization, or any combination thereof. In some embodiments, the materials for additive manufacturing comprise porous of semipermeable materials, glass, plastics, bioplastics or recycled plastics, or any combination thereof. In some embodiments, the materials for additive manufacturing comprise conductive materials. In some embodiments, the conductive materials are embedded into the vessel walls or other photobioreactor structure. In some embodiments, the conductive materials transmit power and/or data, for example, to supply power to one or more photobioreactor components, to relay electronic control signals, and/or to return sensor data. In some embodiments, the materials for additive manufacturing comprise a polymer feedstock with a relatively low melting point. It is contemplated that these materials act as a carrier for silica nanoparticles, the biogenic silica remains of a microorganism, and the like. In some embodiments, a printed component is exposed to a sufficient temperature, such as a temperature greater than 1400 degrees Celsius, and for a sufficient time such that the polymer feedstock burns off and the silica nanoparticles fuse to form a fused or substantially fused glass structure.

In some embodiments, two or more photobioreactors are combined, attached, stacked or otherwise physically interconnected to form a large-scale or industrial photobioreactor, such that the aggregate of photobioreactor vessels operates substantially as a single high-density photobioreactor. In some embodiments, the geometrical configuration of the vessels is such that utilization of available space is maximized. In some embodiments, the two or more vessels are of uniform volume and dimensions or of varying volume and dimensions. In some embodiments, an area provided between two or more photobioreactors for connectivity of one vessel to another, such as, for example, air and water lines that connect a photobioreactors with one or more adjacent photobioreactors. In some embodiments, a set or series of valves between the interconnected vessels directs the flow of air and/or water in a substantially predetermined manner. In some embodiments, a high-density photobioreactor configuration comprises a central column or columns such as, for example, for light distribution, electrical connectivity, manipulation of air and/or liquid between vessels, and the like. In some embodiments, the two or more vessels are assembled using a rigid rack or scaffolding. In some embodiments, the two or more vessels are assembled to occupy an existing structure such as, for example, a silo. In some embodiments, the two or more photobioreactor are assembled to occupy a dedicated structure built to house the photobioreactors. In some embodiments, the two or more photobioreactor are assembled using infrastructure built or additively manufactured into the photobioreactor themselves. In some embodiments, the two or more photobioreactors is printed or substantially printed in place using additive manufacturing processes. In some embodiments, two or more photobioreactors or high-density photobioreactor systems are arranged in a ring around a central axis. In some embodiments, two or more photobioreactors or photobioreactor systems are rotated around the central axis with a sufficient rate of rotation to generate centrifugal force. In some embodiments, the centrifugal force generated is sufficient to simulate gravitational pull within the reactor vessel Monitoring In some embodiments, the photobioreactor comprises one or more monitoring systems. In some embodiments, the monitoring system or systems comprise of one or more sensors. In some embodiments, the one or more of the sensors are positioned on a side of the photobioreactor, such as, for example, on the interior wall of the photobioreactor. In some embodiments, one or more controlled light sources are positioned on the opposite side of the photobioreactor, such that, for example, a given light source faces a sensor or sensors across the interior of the photobioreactor. In some embodiments, the controlled light source or sources interact with one or more sensors, such as, for example, sending fixed numbers of photons across the photobioreactor in the direction of the one or more sensors. In some embodiments, the controlled light source or sources interact with one or more sensors, such as, for example, sending fixed numbers of photons across the photobioreactor in the direction of the one or more sensors. In some embodiments, one or more sensors are configured to detect the number of photons that cross the working fluid from one side of the photobioreactor to the other. In some embodiments, one or more sensors detect the fluorescent response of one or more organisms suspended in the working fluid. In some embodiments, one or more sensors are configured to differentiate reactive protein from total protein. In some embodiments, data collected from the sensors infer characteristics of the working fluid such as, for example, the type, quantity and/or density of free components in the working fluid. In some embodiments, data collected from the sensors is used by one or more systems with the ability to detect harmful algal blooms (HABs) such as, for example, solid-phase adsorption toxin tracking (SPATT), ELISA-based methods for algal toxin screening, liquid chromatography-mass spectrometry, in vivo or in vitro bioassays, real-time quantitative polymerase chain reaction (qPCR) and other molecular probing techniques, or similar chemical or biological sensors. In some embodiments, data collected from the sensors is used to infer the growth and/or health of the culture, such as, for example, the presence of photosynthetic invaders and the presence of cell lysis. In some embodiments, data collected from the sensors is used to infer a measurement of light performance. In some embodiments, the photobioreactor comprise acoustic and/or ultrasonic sensing components.

In some embodiments, the one or more monitoring and/or awareness systems comprise an integrated photometer, such as, for example, an integrated photometer for detecting the actual quantity of photons emitted compared to their expected performance over time. In some embodiments, the integrated photometer comprises two or more points of detection, such that the differential between the two or more points can be used to infer measurements of reactor performance. In some embodiments, the measured parameter is physical air flow, such that the differential between measurements of physical airflow at two or more points infers, for example, energy added to the system for mixing and natural convection. In some embodiments, the measured parameter is carbon dioxide ($CO_2$) uptake, such that the differential between measurements of $CO_2$ uptake at two or more points infers, for example, organism growth rate. In some embodiments, the measured parameter is oxygen ($O_2$) uptake, such that the differential between measurements of $O_2$ uptake at two or more points infers, for example, organism growth rate.

In some embodiments, one or more monitoring and/or awareness systems comprise radar sensing and/or magnetic field detection technology. In some embodiments, the radar sensing and/or magnetic field detection technology comprises one, two or more antennae embedded in the wall of the reactor housing. In some embodiments, data collected from the radar sensing and/or magnetic field detection technology infers, for example, cellular growth, protein content, carbohydrate content, presence of an infection or contaminant, total dissolved solids, fluid flow, system integrity, and the like. In some embodiments, the method for sensing and/or detection comprises use of specific transmission frequencies. In some embodiments, the method for sensing and/or detection comprises deformation of wave forms at two or more frequencies. In some embodiments, the method for sensing and/or detection comprises signal deflection between transmission and reception points on two or more poles of the reactor, such as, for example, the X, Y and Z poles.

In some embodiments, one or more sensors collects data from the interior of the light source photobioreactor. In some embodiments, the photobioreactor comprises one or more microprocessors located in or connected to the interior vessel volume. In some embodiments, one or more of the microprocessors provide for control of one or more light sources. In some embodiments, one or more of the microprocessors provide for feedback monitoring.

In some embodiments, one or more monitoring and/or awareness systems perform a function of culture monitoring characterized by, for example, the use of image analysis, genetic analysis, or protein detection. In some embodiments, the parameter or parameters measured comprise, for example, Nitrogen content, Phosphorous content, Potassium content, gas composition (e.g., dissolved $O_2$, dissolved $CO_2$), presence of sugars, presence of waste products, and the like. In some embodiments, one or more systems perform the function of monitoring culture temperature, monitoring interior vessel volume temperature, monitoring gas flow rates, monitoring liquid flow rates and/or liquid levels, or any combination thereof.

Radiation

In some embodiments, photobioreactor converts electrical energy into electromagnetic radiation and comprises a spherical or substantially spherical light source (e.g., of the water-submersible system) such that light is directed to substantially any location within the photobioreactor. In some embodiments, the light source comprises a water-tight barrier that is spherical shape, such that the barrier separates the interior vessel void from the working fluid and/or culture. In some embodiments, the light source barrier is substantially toroid shape. In some embodiments, the light source barrier is substantially constructed from a variety of inert materials, such as, for example, transparent materials, materials that are tolerant to extreme temperatures, materials that allow for the manipulation of photons, and the like.

In some embodiments, the light source (e.g., of the water-submersible system) comprises a plurality of circuit boards, each comprising at least three edges, arranged in a substantially spherical shape defining an interior light source volume, further characterized by the plurality of circuit boards comprising a first surface in contact with the interior light source volume and an opposing second surface comprising the source of illumination, such as, for example, light emitting diodes (LEDs). In some embodiments, one or more circuit boards comprise flexible qualities that are optionally bent, rounded or otherwise manipulated. In some embodiments, one or more circuit boards is assembled with the assistance of a support structure or framework, such as, for example, a plastic scaffolding. In some embodiments, support structure is assembled from two or more sections of the whole. In some embodiments, support structure is substantially produced using additive manufacturing processes.

In some embodiments, the light source (e.g., of the water-submersible system) comprises organic light emitting diodes (OLEDs). In some embodiments, the light source comprises carbon nanotubes.

In some embodiments, the electromagnetic radiation is inside the visible spectrum, such as, for example, photosynthetically active radiation (PAR). In other embodiments, the electromagnetic radiation is outside the visible spectrum, such as, for example, ultra-violet (UV) or infra-red (IR) light. In some embodiments, the UV and/or IR radiation sterilizes the liquid media in the photobioreactor. In some embodiments, the UV and/or IR radiation, in part or in whole, sterilizes the internal components of the photobioreactor. In some embodiments, the UV and/or IR radiation heats liquid media in the photobioreactor.

In some embodiments, the photobioreactor comprises one or more components supplied by one or more power sources. In some embodiments, one or more of the power sources is positioned externally outside of the photobioreactor. In some embodiments, one or more external power supplies provides power substantially with wireless technology. In some embodiments, one or more external power supplies provide power substantially through f conductive materials, for example, conductive materials that have been incorporated physically into the reactor housing. In some embodiments, the conductive materials are interconnected in such a way as to provide for parallel redundancies in power supply. In some embodiments, one or more power sources are positioned within the interior vessel volume. In some embodiments, one or more components are powered through direct introduction of power, for example, electricity, into the working fluid.

In some embodiments, the light source comprises one or more sensors. In some embodiments, the light source comprises one or more microprocessors. In some embodiments, one or more of the microprocessors is positioned within the interior vessel volume. In some embodiments, one or more of the microprocessors provides control of one or more light sources. In some embodiments, one or more of the microprocessors provides for feedback monitoring. In some embodiments, the light source comprises a connection to one or more control systems, for example, a digital control system. In some embodiments, the controls are incorporated into the light source core vessel volume.

In some embodiments, the radiation manipulated to optimize and/or control for one or more parameters. In some embodiments, the radiation is optimized to increase the likelihood of photon absorption by the organism or organisms in the working fluid. In some embodiments, the method of radiation manipulation is substantially by the use of pulse-width modulation. In some embodiments, the method of radiation manipulation is substantially by the incorporation of materials and/or meta-materials with the ability to manipulate and/or influence the behavior of light. In some embodiments, the materials and/or meta-materials provide for the manipulation of light at, for example, a macroscopic, particle or quantum level. In some embodiments, the bioreactor component into which the materials and/or meta-materials are incorporated into the external surface of a light source. In some embodiments, the materials and/or meta-materials provide for the manipulation of light by bouncing or reflecting one or more photons into the working fluid. In some embodiments, one or more photons is directed into the working fluid at oblique angles to the direct angle of light source emission. In some embodiments, materials and/or meta-materials comprise reflective and/or refractive surface coatings. In some embodiments, materials and/or meta-materials comprise inherently reflective and/or refractive materials. In some embodiments, materials and/or meta-materials comprise embedded particulates such as, for example, nanoparticles, quantum dots and the like. In some embodiments, the particulates are embedded into the materials and/or meta-materials through additive manufacturing processes. In some embodiments, materials and/or meta-materials provide for the discrete manipulation of photons. In some embodiments, materials and/or meta-materials are applied to one or more culture-facing surfaces. In some embodiments, materials and/or meta-materials are incorporated into one or more culture-facing surfaces through additive manufacturing processes. In some embodiments, the method of radiation manipulation is characterized by the use of optical structures having the ability to distort and/or bend light, such as, for example, the ability to twist light. In some embodiments, optical structures are constructed substantially using additive manufacturing processes. In some embodiments, one more lenses have the ability to distort, bend and/or twist light. In some embodiments, one or more reflective surfaces with the ability to distort, bend and/or twist light Temperature In some embodiments, the photobioreactor comprises a temperature controlling and/or managing system. In some embodiments, one or more systems manage temperature substantially through the use of ambient temperature control. In some embodiments, one or more systems achieve temperature management substantially through light source manipulation. In some embodiments, light source manipulation comprises controlled variations in light frequency. In some embodiments, light source manipulation comprises controlled variations in power, intensity, or both power and intensity.

In some embodiments, one or more systems achieve temperature management substantially through electrical elements, such as, for example, electrical heating elements. In some embodiments, one or more systems achieve temperature management through the use of forced cooling. In some embodiments, one or more systems achieve temperature management through the use of a cooling device. In some embodiments, the cooling device comprises a cooling jacket.

In some embodiments, one or more systems for temperature management and/or control comprise one or more pumps, such as, for example, fluid pumps. In some embodiments, one or more systems achieve temperature management substantially through the use of heat dispersal fluid. In some embodiments, heat dispersal fluid is optically clear or substantially optically clear. In some embodiments, the heat dispersal fluid is a non-conductive liquid or a substantially non-conductive liquid, such as, for example, mineral oil. In some embodiments, the heat dispersal fluid is a non-conductive gel or a substantially non-conductive gel. In some embodiments, the heat dispersal fluid comprises quantum dots, reflective particles, or the like. In some embodiments, the heat dispersal fluid emits light when exposed to heat. In some embodiments, the heat dispersal fluid is recirculated inside the interior vessel volume. In some embodiments, the circulation is achieved using or substantially using natural convection or variations in the flow rate of one or more pumps. In some embodiments, one or more of the pumps are positioned outside of the reactor vessel. In some embodiments, one or more of the pumps is connected to the light source via one or more inlets and/or one or more outlets. In some embodiments, one or more of the pumps is substantially incorporated into the light source vessel volume. In some embodiments, one or more of the pumps is substantially characterized as micro-pumps. In some embodiments, the system or system for circulating heat dispersal fluid comprises one or more fans, such as, for example, gyroscopic fans. In some embodiments, one or more of the fans is incorporated into the light source vessel volume.

Applications

In some embodiments, the photobioreactor is suitable for the culture of photosynthetic and/or photosensitive microorganisms. In some embodiments, one or more photosynthetic and/or photosensitive organisms comprise a productive culture. In some embodiments, one or more of the organisms is substantially unmodified or naturally occurring. In some embodiments, one or more of the organisms is substantially adapted to a suitable environment. In some embodiments, one or more of the organisms is characterized as substantially genetically modified or recombinant. In some embodiments, one or more of the organisms comprise synthetic DNA, such that, for example, the DNA has been assembled to substantially form an organism that does not exist in any naturally occurring environment. In some embodiments, one or more of the organisms is photosensitive rather than photosynthetic, such that, for example, light stimulation may be used as a method of control over one or more parameters, rather than or in addition to utilization as an energy source, a driver of reproduction or growth, and the like.

In some embodiments, one or more of the organisms produce compounds or biomolecules including, for example, fatty acids, phycobiliproteins, biofuels and other petrol substitutes, and the like. In some embodiments, the photobioreactors is further characterized by the ability to manipulate and/or optimize one or more controls, components or other reactor parameters, such as, for example, adjustments to optimize an environment for individual organisms. In some embodiments, the manipulation and/or optimization adjusts or varies one or more inputs, monitors one or more outputs, facilitates high growth and/or high density for a particular organism or organisms, controls the rate of expression of biogenic molecules, such as, for example, molecules of unique interest or particular value, alters organism life cycle, alters final nutritional or product components, induces cell destruction or lysis, causes the cell to take protective action, such that, for example, the destruction, lysis or protective action encourages the production of one or more key molecules, or any combination thereof. In some embodiments, the manipulation and/or optimization is targeted for a specific application or applications, such as, for example, research and development applications, commercial applications, and industrial applications. In some embodiments, applications include cellular agriculture, such as, for example, the production of food products, functional ingredients, additives and/or supplements for human consumption; food products, functional ingredients, additives and/or supplements for pet, livestock and other animal consumption; phycobiliproteins; biofuels; feedstocks for medical, biomedical and/or pharmaceutical applications; and the like. In some embodiments, applications are biomanufacturing, the storage of energy, photochemistry, photolysis or photo-destruction, production of compounds or molecules such as, for example, biofuels, bioremediation of wastewater, excess carbon dioxide, and the like, or any combination thereof. In some embodiments, bioremediation may comprise a cooperative or symbiotic system between the one or more photobioreactors and one or more living animals such that, for example, waste carbon dioxide and waste nutrients from the animal or animals may be substantially converted through the photobioreactor bioremediation process into oxygen and nutrients for the animal or animals. In some embodiments, one or more photobioreactors provide the bioremediation and conversion of waste products for one or more humans. In some embodiments, one or more photobioreactors provide for the bioremediation and conversion of waste products on a spacecraft or other non-Terran habitat, such as a non-Terran surface habitat.

Para. A. A photobioreactor for cultivation and/or propagation of a photosynthetic organism comprising: a substantially spherical vessel having a wall defining an interior vessel volume; a water-submersible system for converting electrical energy into electromagnetic radiation; a temperature management system for circulating heat dispersal fluid into and out of the water-submersible system; and a photobioreactor control system comprising a processor and a controller.

Para. B. The photobioreactor of Para. A, further comprising one or more sensors in operable communication with the photobioreactor control system.

Para. C. The photobioreactor of any one of Para. A-B, wherein the one or more sensors comprise either a hardwired or wireless connection.

Para. D. The photobioreactor of any one of Para. A-C, wherein the one or more sensors comprise a temperature sensor, a gas sensor, an acid or a pH sensor, a protein differentiation detector, a spectrophotometer, or a cytometer.

Para. E. The photobioreactor of any one of Paras. A-D, wherein the one or more sensors is positioned on an interior surface of the wall of the substantially spherical vessel.

Para. F. The photobioreactor of any one of Paras. A-E, wherein one or more controlled sources of electromagnetic energy is positioned on the opposite side of the substantially spherical vessel relative to the one or more sensors.

Para. G. The photobioreactor of any one of Paras. A-F, wherein the one or more sensors are positioned within the water-submersible system.

Para. H. The photobioreactor of any one of Paras. A-G, wherein the one or more sensors comprise a component sensitive to photons, fluorescence or reactive protein.

Para. I. The photobioreactor of any one of Paras. A-H, wherein the one or more sensors comprise an integrated photometer.

Para. J. The photobioreactor of any one of Paras. A-I, wherein the integrated photometer comprises two or more points of detection.

Para. K. The photobioreactor of any one of Paras. A-J, wherein the one or more sensors comprise radar or magnetic field detection sensors.

Para. L. The photobioreactor of any one of Paras. A-K, wherein the radar or magnetic field detection sensor comprises one or more antennae.

Para. M. The photobioreactor of any one of Paras. A-L, wherein the one or more antennae are integrated into a reactor housing or structure of the photobioreactor.

Para. N. The photobioreactor of any one of Paras. A-M, wherein the one or more sensors comprise an acoustic or ultrasonic sensor.

Para. O. The photobioreactor of any one of Paras. A-N, wherein at least one of the one or more sensors are integrated into a reactor housing or structure of the photobioreactor.

Para. P. The photobioreactor of any one of Paras. A-O, wherein additive manufacturing is used to integrate at least one of the one or more sensors into the reactor housing or structure.

Para. Q. The photobioreactor of any one of Paras. A-P, wherein the additive manufacturing comprises a process using conductive printing feedstock.

Para. R. The photobioreactor of any one of Paras. A-Q, wherein the processor comprises a microprocessor.

Para. S. The photobioreactor of any one of Paras. A-R, wherein the microprocessor is positioned within the water-submersible system.

Para. T. The photobioreactor of any one of Paras. A-S, wherein the controller comprises a microcontroller.

Para. U. The photobioreactor of any one of Paras. A-T, wherein the microcontroller is positioned within the water-submersible system.

Para. V. The photobioreactor of any one of Paras. A-U, wherein the photobioreactor control system is configured to manage the water-submersible system.

Para. W. The photobioreactor of any one of Paras. A-V, wherein the water-submersible system is managed substantially through light source manipulation.

Para. X. The photobioreactor of any one of Paras. A-W, wherein the light source manipulation comprises controlled variations in light frequency.

Para. Y. The photobioreactor of any one of Paras. A-X, wherein the light source manipulation comprises controlled variations in power, light intensity, or both.

Para. Z. The photobioreactor of any one of Paras. A-Y, wherein said light source manipulation comprises pulsed width modulation.

Para. AA. The photobioreactor of any one of Paras. A-Z, further comprising: a system of distributed positive (anode) and negative (cathode) conductors configured to provide electricity to the photobioreactor; or a system of distributed electromagnets configured to provide electricity to the photobioreactor.

Para. AB. The photobioreactor of any one of Paras. A-AA, further comprising one or more power supplies.

Para. AC. The photobioreactor of any one of Paras. A-AB, wherein at least one of the one or more power supplies is positioned outside of the substantially spherical vessel.

Para. AD. The photobioreactor of any one of Paras. A-AC, wherein at least one of the one or more power supplies is positioned within the interior vessel volume.

Para. AE. The photobioreactor of any one of Paras. A-AD, wherein at least one of the one or more power supplies is positioned within the water-submersible system.

Para. AF. The photobioreactor of any one of Paras. A-AE, wherein at least one of the one or more power supplies comprises either a hard-wired or wireless connection.

Para. AG. The photobioreactor of any one of Paras. A-AF, wherein the hard-wired or wireless connection comprises a conductive material that has been integrated into the reactor housing or structure of the photobioreactor through additive manufacturing.

Para. AH. The photobioreactor of any one of Paras. A-AG, wherein at least one of the one or more power supplies directly introduces electricity into a working fluid positioned in the interior vessel volume.

Para. AI. The photobioreactor of any one of Paras. A-AH, further comprising a circulation system for manipulating, extracting or circulating fluid, waste or nutrients into and out of the substantially spherical vessel, wherein the circulation system is in operable communication with the photobioreactor control system.

Para. AJ. The photobioreactor of any one of Paras. A-AI, wherein the circulation system comprises one or more motors, pumps, valves or fans.

Para. AK. The photobioreactor of any one of Paras. A-AJ, wherein the one or more valves comprise an electronically controlled valve.

Para. AL. The photobioreactor of any one of Paras. A-AK, wherein the one or more motors comprise an electronically controlled motor.

Para. AM. The photobioreactor of any one of Paras. A-AL, wherein the one or more pumps comprise an electronically controlled pump.

Para. AN. The photobioreactor of any one of Paras. A-AM, wherein at least one of the one or more pumps is thermodynamic.

Para. AO. The photobioreactor of any one of Paras. A-AN, wherein at least one of the one or more motors, pumps, valves or fans is integrated into the reactor housing or structure of the photobioreactor.

Para. AP. The photobioreactor of any one of Paras. A-AO, wherein at least one of the one or more motors, pumps, valves or fans is integrated into the water-submersible system.

Para. AQ. The photobioreactor of any one of Paras. A-AP, wherein the circulation system comprises one or more inlets and one or more outlets.

Para. AR. The photobioreactor of any one of Paras. A-AQ, wherein the circulation system comprises a spigot configured to control a flow in the circulation system.

Para. AS. The photobioreactor of any one of Paras. A-AR, wherein the one or more inlets and outlets are integrated into the reactor housing or structure of the photobioreactor.

Para. AT. The photobioreactor of any one of Paras. A-AS, further comprising a ventilation system for the addition or dispersion of gases into the substantially spherical vessel, wherein the ventilation system comprises one or more gas diffusion devices.

Para. AU. The photobioreactor of any one of Paras. A-AT, wherein at least one of the one or more gas diffusion devices is substantially ring-shaped or disc-shaped.

Para. AV. The photobioreactor of any one of Paras. A-AU, wherein the ventilation system comprises two or more ring-shaped or disc-shaped gas diffusion devices positioned at different heights within the interior vessel volume.

Para. AW. The photobioreactor of any one of Paras. A-AV, wherein at least one of the one or more gas diffusion devices is substantially cylindrical or spherical.

Para. AX. The photobioreactor of any one of Paras. A-AW, wherein the ventilation system comprises a plurality of gas diffusion devices arranged in a substantially circular shape within the interior vessel volume to form one or more rings or discs.

Para. AY. The photobioreactor of any one of Paras. A-AX, wherein at least two of the plurality of gas diffusion devices are positioned at different heights within the interior vessel volume.

Para. AZ. The photobioreactor of any one of Paras. A-AY, wherein at least one of the one or more gas diffusion devices comprises a porous or semi-permeable material.

Para. BA. The photobioreactor of any one of Paras. A-AZ, wherein at least one of the one or more gas diffusion devices is integrated into the reactor housing or structure of the photobioreactor.

Para. BB. The photobioreactor of any one of Paras. A-BA, wherein additive manufacturing is used to integrate at least one of the one or more gas diffusion devices into the reactor housing or structure.

Para. BC. The photobioreactor of any one of Paras. A-BB, wherein the ventilation system comprises one or more gas chambers.

Para. BD. The photobioreactor of any one of Paras. A-BC, wherein at least one of the one or more gas chambers comprises a void or internal volume integrated into the reactor housing or structure of the photobioreactor.

Para. BE. The photobioreactor of any one of Paras. A-BD, wherein additive manufacturing is used to integrate at least one of the one or more gas chambers into the reactor housing or structure.

Para. BF. The photobioreactor of any one of Paras. A-BE, wherein the ventilation system comprises a manifold or network of two or more channels or tubes connecting at least one of the one or more gas chambers to at least one of the one or more gas diffusion devices.

Para. BG. The photobioreactor of any one of Paras. A-BF, wherein the manifold or network is integrated into the reactor housing or structure of the photobioreactor.

Para. BH. The photobioreactor of any one of Paras. A-BG, wherein additive manufacturing is used to integrate at least one of the manifolds or networks into the reactor housing or structure.

Para. BI. The photobioreactor of any one of Paras. A-BH, wherein the ventilation system comprises one or more valves, pumps, motors or fans.

Para. BJ. The photobioreactor of any one of Paras. A-BI, wherein the one or more valves comprise electronically controlled valves.

Para. BK. The photobioreactor of any one of Paras. A-BJ, wherein the one or more motors comprise electronically controlled motors.

Para. BL. The photobioreactor of any one of Paras. A-BK, wherein the one or more pumps comprise electronically controlled pumps.

Para. BM. The photobioreactor of any one of Paras. A-BL, wherein the ventilation system is in operable communication with the photobioreactor control system.

Para. BN. The photobioreactor of any one of Paras. A-BM, wherein a gas addition or dispersion rate is managed substantially using controlled variations in gas or air pressure.

Para. BO. The photobioreactor of any one of Paras. A-BN, wherein the wall defining the interior vessel volume comprises a dual-layered wall having an interior layer and an exterior layer.

Para. BP. The photobioreactor of any one of Paras. A-BO, wherein the wall comprises a void between the interior layer and the exterior layer.

Para. BQ. The photobioreactor of any one of Paras. A-BP, wherein the exterior layer is water impermeable.

Para. BR. The photobioreactor of any one of Paras. A-BQ, wherein the interior layer is porous or semi-permeable.

Para. BS. The photobioreactor of any one of Paras. A-BR, wherein porosity or permeability of the interior layer is variable.

Para. BT. The photobioreactor of any one of Paras. A-BS, wherein the porosity or permeability of the interior layer varies in response to a signal from the photobioreactor control system or in response to environmental conditions such as temperature, pH or specific types or wavelengths or radiation.

Para. BU. The photobioreactor of any one of Paras. A-BT, wherein the substantially spherical vessel is constructed from one or more of a variety of food grade or highly inert materials that do not leach, are corrosion-resistant, are heat-resistant, and/or withstand light pressurization.

Para. BV. The photobioreactor of any one of Paras. A-BU, wherein the substantially spherical vessel comprises high-density polyethylene, low-density polyethylene, polypropylene, or bioplastics.

Para. BW. The photobioreactor of any one of Paras. A-BV, wherein the substantially spherical vessel comprises glass, silica composites, borosilicate, or ceramics.

Para. BX. The photobioreactor of any one of Paras. A-BW, wherein the substantially spherical vessel comprises stainless steel.

Para. BY. The photobioreactor of any one of Paras. A-BX, wherein the substantially spherical vessel comprises carbon fiber.

Para. BZ. The photobioreactor of any one of Paras. A-BY, wherein the water-submersible system comprises a spherical or substantially spherical inner vessel having an inner wall defining an inner space.

Para. CA. The photobioreactor of any one of Paras. A-BZ, wherein the spherical or substantially inner vessel is torus-shaped.

Para. CB. The photobioreactor of any one of Paras. A-CA, wherein the spherical or substantially spherical inner vessel comprises one or more of a variety of inert materials that are tolerant to extreme temperatures.

Para. CC. The photobioreactor of any one of Paras. A-CB, wherein the spherical or substantially spherical inner vessel comprises plastic or glass.

Para. CD. The photobioreactor of any one of Paras. A-CC, wherein the spherical or substantially spherical inner vessel is substantially transparent.

Para. CE. The photobioreactor of any one of Paras. A-CD, wherein the spherical or substantially spherical inner vessel comprises materials or meta-materials that allow for manipulation of photons.

Para. CF. The photobioreactor of any one of Paras. A-CE, comprising materials or meta-materials with properties that enable the manipulation and/or influence the behavior of electromagnetic radiation.

Para. CG. The photobioreactor of any one of Paras. A-CF, wherein the materials or meta-materials are present on one or more working-liquid-facing surfaces.

Para. CH. The photobioreactor of any one of Paras. A-CG, wherein the materials or meta-materials comprise reflective or refractive surface coatings.

Para. CI. The photobioreactor of any one of Paras. A-CH, wherein the materials or meta-materials comprise inherently reflective or refractive materials.

Para. CJ. The photobioreactor of any one of Paras. A-CI, wherein the materials or meta-materials comprise nanoparticles, quantum dots or similar embedded particulates.

Para. CK. The photobioreactor of any one of Paras. A-CJ, wherein the materials or meta-materials comprise optical lenses or similar structures with ability to distort, bend or twist light.

Para. CL. The photobioreactor of any one of Paras. A-CK, wherein the materials or meta-materials are incorporated into the water-submersible system using additive manufacturing.

Para. CM. The photobioreactor of any one of Paras. A-CL, comprising one or more surfaces with hydrophobic, superhydrophobic, hydrophilic or oleophobic properties.

Para. CN. The photobioreactor of any one of Paras. A-CM, wherein the properties are substantially achieved through surface coating.

Para. CO. The photobioreactor of any one of Paras. A-CN, wherein the properties are substantially achieved through mechanical or thermal etching.

Para. CP. The photobioreactor of any one of Paras. A-CO, wherein the properties are substantially achieved through using materials with the inherently hydrophobic, superhydrophobic, hydrophilic and/or oleophobic properties.

Para. CQ. The photobioreactor of any one of Paras. A-CP, wherein the properties are substantially achieved through high-resolution additive manufacturing.

Para. CR. The photobioreactor of any one of Paras. A-CQ, wherein the reactor housing and/or structure is produced using additive manufacturing processes including, for example, binder jetting, directed energy deposition, material extrusion, material jetting, powder bed fusion, sheet lamination, or vat photopolymerization.

Para. CS. The photobioreactor of any one of Paras. A-CR, wherein the reactor housing and/or structure comprises porous or semipermeable materials.

Para. CT. The photobioreactor of any one of Paras. A-CS, wherein the reactor housing and/or structure comprises glass Para. CU. The photobioreactor of any one of Paras. A-CT, wherein the reactor housing and/or structure comprises plastics, bioplastics, or recycled plastics.

Para. CV. The photobioreactor of any one of Paras. A-CU, wherein the reactor housing and/or structure comprises two or more materials assembled using additive manufacturing processes, such that the two or more materials fuse during the additive manufacturing process to form a watertight or substantially watertight barrier.

Para. CW. The photobioreactor of any one of Paras. A-CV, wherein the substantially spherical outer vessel comprises two or more materials assembled using additive manufacturing processes, such that the two or more materials fuse during the additive manufacturing process to form a watertight or substantially watertight barrier.

Para. CX. The photobioreactor of any one of Paras. A-CW, wherein the substantially spherical inner vessel comprises two or more materials assembled using additive manufacturing processes, such that the two or more materials fuse during the additive manufacturing process to form a watertight or substantially watertight barrier.

Para. CY. The photobioreactor of any one of Paras. A-CX, wherein one or more inlets, outlets, pumps, valves, motors, or fans is substantially integrated into the reactor housing or structure.

Para. CZ. The photobioreactor of any one of Paras. A-CY, wherein power, data or control paths are substantially integrated into the reactor housing or structure.

Para. DA. The photobioreactor of any one of Paras. A-CZ, wherein the power, data or control paths comprise conductive feedstock.

Para. DB. The photobioreactor of any one of Paras. A-DA, wherein the reactor housing and/or structure comprises polymer feedstock and silica particles, wherein the polymer feedstock and silica particles comprise silica nanoparticles or biogenic silica remains of a microorganism.

Para. DC. The photobioreactor of any one of Paras. A-DB, wherein the polymer feedstock is at least partially eliminated and the silica particles form a substantially fused glass structure.

Para. DD. The photobioreactor of any one of Paras. A-DC, wherein converting electrical energy to electromagnetic radiation comprises one or more sources of illumination.

Para. DE. The photobioreactor of any one of Paras. A-DD, wherein the one or more sources of illumination comprise one or more light-emitting diodes (LEDs), and/or one or more organic light-emitting diodes (OLEDs).

Para. DF. The photobioreactor of any one of Paras. A-DE, further comprising a scaffold or framework.

Para. DG. The photobioreactor of any one of Paras. A-DF, wherein the one or more sources of illumination are connected to the scaffold or framework.

Para. DH. The photobioreactor of any one of Paras. A-DG, wherein the scaffold comprises one or more of a variety of inert materials that are tolerant to extreme temperatures.

Para. DI. The photobioreactor of any one of Paras. A-DH, wherein the scaffold is integrated into the reactor housing or structure of the photobioreactor.

Para. DJ. The photobioreactor of any one of Paras. A-DI, wherein the one or more sources of illumination comprise carbon nanotubes.

Para. DK. The photobioreactor of any one of Paras. A-DJ, wherein the one or more sources of illumination comprise biologically based sources of illumination.

Para. DL. The photobioreactor of any one of Paras. A-DK, wherein the biologically based sources of illumination comprise modified diatoms.

Para. DM. The photobioreactor of any one of Paras. A-DL, wherein the one or more sources of illumination comprise sources of radiation within a visible spectrum.

Para. DN. The photobioreactor of any one of Paras. A-DM, wherein the one or more sources of illumination comprise sources of photosynthetically active radiation.

Para. DO. The photobioreactor of any one of Paras. A-DN, wherein the one or more sources of illumination comprise sources of radiation outside a visible spectrum.

Para. DP. The photobioreactor of any one of Paras. A-DO, wherein the one or more sources of illumination comprise sources of ultraviolet or near-ultraviolet radiation.

Para. DQ. The photobioreactor of any one of Paras. A-DP, wherein the one or more sources of illumination comprise sources of microwave radiation.

Para. DR. The photobioreactor of any one of Paras. A-DQ, wherein the photobioreactor control system is configured to manage the temperature of the interior vessel volume.

Para. DS. The photobioreactor of any one of Paras. A-DR, wherein the temperature is managed substantially through light source manipulation.

Para. DT. The photobioreactor of any one of Paras. A-DS, wherein the light source manipulation comprises controlled variations in light frequency.

Para. DU. The photobioreactor of any one of Paras. A-DT, wherein the light source manipulation comprises controlled variations in power, light intensity, or both.

Para. DV. The photobioreactor of any one of Paras. A-DU, wherein the temperature management system in operable communication with the photobioreactor control system.

Para. DW. The photobioreactor of any one of Paras. A-DV, wherein the temperature management system comprises one or more electrical heating elements.

Para. DX. The photobioreactor of any one of Paras. A-DW, wherein the temperature management system further comprises a cooling device.

Para. DY. The photobioreactor of any one of Paras. A-DX, wherein the cooling device comprises a cooling jacket.

Para. DZ. The photobioreactor of any one of Paras. A-DY, wherein the temperature management system comprises controlled variations in ambient temperature.

Para. EA. The photobioreactor of any one of Paras. A-DZ, wherein the temperature management system is configured to circulate the heat dispersal fluid into and out of the water-submersible system via a conduit, such as a pipe or tube.

Para. EB. The photobioreactor of any one of Paras. A-EA, wherein the heat dispersal fluid is substantially optically clear.

Para. EC. The photobioreactor of any one of Paras. A-EB, wherein the heat dispersal fluid is a non-conductive liquid or gel.

Para. ED. The photobioreactor of any one of Paras. A-EC, wherein the heat dispersal fluid comprises quantum dots or reflective particles Para. EE. The photobioreactor of any one of Paras. A-ED, wherein the heat dispersal fluid emits light when exposed to heat Para. EF. The photobioreactor of any one of Paras. A-EE, wherein the heat dispersal fluid is circulated by natural convection.

Para. EG. The photobioreactor of any one of Paras. A-EF, wherein the temperature management system comprises one or more motors, pumps, valves or fans.

Para. EH. The photobioreactor of any one of Paras. A-EG, wherein the photobioreactor control system is configured to cause variations in flow rates of the one or more pumps.

Para. EI. The photobioreactor of any one of Paras. A-EH, wherein the one or more pumps is positioned outside of the substantially spherical vessel.

Para. EJ. The photobioreactor of any one of Paras. A-EI, wherein the one or more pumps is connected to the water-submersible system via one or more inlets and one or more outlets.

Para. EK. The photobioreactor of any one of Paras. A-EJ, wherein at least one of the one or more pumps is present in the water-submersible system.

Para. EL. The photobioreactor of any one of Paras. A-EK, wherein the one or more pumps comprise micro-pumps.

Para. EM. The photobioreactor of any one of Paras. A-EL, wherein at least one of the one or more fans is present in the water-submersible system.

Para. EN. The photobioreactor of any one of Paras. A-EM, wherein the one or more fans comprise gyroscopic or electronically controlled fans.

Para. EO. The photobioreactor of any one of Paras. A-EN, wherein the one or more valves comprise electrically controlled valves.

Para. EP. The photobioreactor of any one of Paras. A-EO, wherein the one or more motors comprise electronically controlled motors.

Para. EQ. The photobioreactor of any one of Paras. A-EP, further comprising one or more cleaning units.

Para. ER. The photobioreactor of any one of Paras. A-EQ, wherein one or more of the cleaning units are positioned within the interior vessel volume.

Para. ES. The photobioreactor of any one of Paras. A-ER, wherein one or more of the cleaning units are positioned on an outer surface of the water-submersible system.

Para. ET. The photobioreactor of any one of Paras. A-ES, wherein one or more of the cleaning units are free-floating in the interior vessel volume.

Para. EU. The photobioreactor of any one of Paras. A-ET, wherein the cleaning units comprise one or more robotic devices.

Para. EV. The photobioreactor of any one of Paras. A-EU, wherein the cleaning units comprise a vacuum or suction component.

Para. EW. The photobioreactor of any one of Paras. A-EV, wherein the cleaning units comprise a filter component.

Para. EX. The photobioreactor of any one of Paras. A-EW, wherein the cleaning units comprise one or more pumps, motors, valves or fans Para. EY. The photobioreactor of any one of Paras. A-EX, wherein the cleaning units are substantially flexible or pliable.

Para. EZ. The photobioreactor of any one of Paras. A-EY, wherein the cleaning units are gas-operated.

Para. FA. The photobioreactor of any one of Paras. A-EZ, further comprising one or more cleaning unit actuators.

Para. FB. The photobioreactor of any one of Paras. A-FA, comprising a physical connection to one or more additional photobioreactors.

Para. FC. The photobioreactor of any one of Paras. A-FB, wherein the one or more additional photobioreactors are of similar dimensions or volume.

Para. FD. The photobioreactor of any one of Paras. A-FC, wherein the one or more additional photobioreactors are of varied dimensions or volume.

Para. FE. The photobioreactor of any one of Paras. A-FD, wherein the physical connection comprises a rigid rack or scaffolding.

Para. FF. The photobioreactor of any one of Paras. A-FE, wherein the physical connection comprises a pre-existing structure, wherein the pre-existing structure comprises a silo.

Para. FG. The photobioreactor of any one of Paras. A-FF, wherein the physical connection comprises a structure designed and built for housing a plurality of photobioreactors.

Para. FH. The photobioreactor of any one of Paras. A-FG, wherein the structure further comprises areas and/or equipment dedicated to media preparation.

Para. FI. The photobioreactor of any one of Paras. A-FH, wherein the structure further comprises areas and/or equipment dedicated to biomass processing.

Para. FJ. The photobioreactor of any one of Paras. A-FI, wherein the physical connection comprises a substantially additively manufactured structure.

Para. FK. The photobioreactor of any one of Paras. A-FJ, wherein the physical connection comprises one or more conduits, tubes or pipes.

Para. FL. The photobioreactor of any one of Paras. A-FK, wherein the conduits comprise gas lines Para. FM. The photobioreactor of any one of Paras. A-FL, wherein the conduits comprise water, media or culture lines.

Para. FN. The photobioreactor of any one of Paras. A-FM, wherein the conduits comprise power, electrical or data lines.

Para. FO. The photobioreactor of any one of Paras. A-FN, further comprising one or more valves, pumps, motors or fans.

Para. FP. The photobioreactor of any one of Paras. A-FO, wherein a set or series of valves between two or more interconnected vessels directs a flow of gas or liquid in a substantially predetermined manner.

Para. FQ. The photobioreactor of any one of Paras. A-FP, wherein the photobioreactor control system is configured to manage a flow of gas or liquid between connected photobioreactors.

Para. FR. The photobioreactor of any one of Paras. A-FQ, comprising a connection to a central column, pipe, tube, scaffold or similar pole.

Para. FS. The photobioreactor of any one of Paras. A-FR, wherein the central column comprises connections to one or more additional photobioreactors.

Para. FT. The photobioreactor of any one of Paras. A-FS, wherein the central column comprises a central axis around which a plurality of photobioreactors are arranged.

Para. FU. The photobioreactor of any one of Paras. A-FT, wherein the plurality of photobioreactors are arranged in a substantially circular or ring shape.

Para. FV. The photobioreactor of any one of Paras. A-FU, wherein the plurality of photobioreactors is rotatably positioned around said central axis.

Para. FW. The photobioreactor of any one of Paras. A-FV, wherein the central column comprises one or more shared gas, liquid, power, data or electrical lines.

Para. FX. The photobioreactor of any one of Paras. A-FW, wherein the photobioreactor control system is in operable communication with an additional photobioreactor control system or systems of the one or more additional photobioreactors.

Para. FY. The photobioreactor of any one of Paras. A-FX, further comprising a connection to a centralized control system that is in operable communication with one or more additional photobioreactors.

Para. FZ. The photobioreactor of any one of Paras. A-FY, wherein two or more connected photobioreactors and photobioreactor control systems form a substantially distributed network, wherein data may be aggregated from the two or more photobioreactors.

Para. GA. The photobioreactor of any one of Paras. A-FZ, wherein the centralized control system is substantially configured to operate based on a traditional decisional artificial intelligence structure, wherein the structure is a top-down artificial intelligence algorithm.

Para. GB. The photobioreactor of any one of Paras. A-GA, further comprising one or more low-power computers in operable communication with one or more sensors.

Para. GC. The photobioreactor of any one of Paras. A-GB, wherein the low-power computers are configured to control a given function of an associated photobioreactor in response to data from one or more connected photobioreactors.

Para. GD. The photobioreactor of any one of Paras. A-GC, wherein the centralized control system is substantially configured to operate based on a situated or behavioral decisional artificial intelligence structure, wherein the structure is a multi-heuristic algorithm such as a flocking algorithm.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein can be further limited in the claims using, consisting of, or and consisting essentially, of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

It is to be understood that the embodiments of the disclosure disclosed herein are illustrative of the principles of the present disclosure. Other modifications that can be employed are within the scope of the disclosure. Thus, by way of example, but not of limitation, alternative configurations of the present disclosure can be utilized in accordance with the teachings herein. Accordingly, the present disclosure is not limited to that precisely as shown and described.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety, including, WO2013138690A1.

The invention claimed is:

1. A photobioreactor for cultivation and/or propagation of a photosynthetic organism, the photobioreactor comprising:
   a vessel having a wall defining an interior vessel volume and configured to hold a working fluid including biomass;
   a water-submersible system comprising an inner vessel having an inner wall defining an inner space, wherein the water-submersible system is configured to convert electrical energy into light;
   a temperature management system comprising one or more conduits and a first sensor at the inner wall within the inner space of the water-submersible system, the temperature management system being configured to circulate fluid into and out of the water-submersible system via the one or more conduits to provide forced cooling of the water-submersible system based at least in part on a first signal provided from the first sensor;
   a light source positioned to emit light toward the interior vessel volume;
   a second sensor at or within the wall defining the interior vessel volume and positioned to receive the emitted light from the light source, the second sensor being configured to generate a second signal corresponding to the received light and indicative of a status of growth of the biomass within the vessel; and
   a photobioreactor control system comprising a processor and a controller, the photobioreactor control system being operably coupled to the second sensor and the light source such that the photobioreactor control system is configured to adjust the light emitted via the light source based at least in part on the second signal.

2. The photobioreactor of claim 1, further comprising one or more third sensors in operable communication with the photobioreactor control system, wherein the one or more third sensors comprise a temperature sensor, a gas sensor, an acid or pH sensor, a protein differentiation detector, a spectrophotometer, or a cytometer.

3. The photobioreactor of claim 2, wherein at least one of the one or more third sensors is positioned within the interior vessel volume.

4. The photobioreactor of claim 1, wherein the photobioreactor control system is configured to manage the water-submersible system.

5. The photobioreactor of claim 1, further comprising one or more power supplies positioned external to the interior vessel volume.

6. The photobioreactor of claim 1, further comprising a ventilation system for the addition or dispersion of gases into the vessel, wherein the ventilation system comprises one or more gas diffusion devices.

7. The photobioreactor of claim 6, wherein the ventilation system comprises a plurality of gas diffusion devices arranged in a substantially circular shape within the interior vessel volume.

8. The photobioreactor of claim 6, wherein at least one of the one or more gas diffusion devices is integrated into the interior vessel volume.

9. The photobioreactor of claim 6, wherein the one or more gas diffusion devices are cylindrical or substantially cylindrical.

10. The photobioreactor of claim 1, wherein the wall defining the interior vessel volume comprises a dual-layered wall having an interior layer and an exterior layer.

11. The photobioreactor of claim 1, wherein the temperature is managed substantially through light source manipulation and is in operable communication with the photobioreactor control system.

12. The photobioreactor of claim 1, wherein the temperature management system comprises a fan configured to provide the forced air cooling of said system.

13. The photobioreactor of claim 1, wherein the light source is positioned on an inner surface of the wall defining the interior vessel volume, and where the light source faces toward the water-submersible system.

14. A photobioreactor comprising:
   a vessel having a wall defining an interior vessel volume and configured to hold a working fluid including biomass;
   a water-submersible system comprising an inner vessel having an inner wall defining an inner space, wherein the water-submersible system is configured to convert electrical energy into light;
   a first sensor within the inner space of the water-submersible system and facing inwardly;
   one or more conduits positioned to circulate fluid into and out of the water-submersible system to provide cooling thereof based at least in part on a first signal provided from the first sensor;
   a light source positioned to emit light toward the interior vessel volume;
   a second sensor at or within the wall defining the interior vessel volume and positioned to receive the emitted light from the light source, the second sensor being configured to generate a second signal corresponding to the received light and indicative of a status of growth of the biomass within the vessel; and
   a photobioreactor control system comprising a processor and a controller, the photobioreactor control system being operably coupled to the second sensor and the light source such that the photobioreactor control system is configured to adjust the light emitted via the light source based at least in part on the second signal.

* * * * *